(12) United States Patent
Acker et al.

(10) Patent No.: US 7,780,673 B2
(45) Date of Patent: Aug. 24, 2010

(54) METHOD AND APPARATUS FOR PERFORMING A MINIMALLY INVASIVE TOTAL HIP ARTHROPLASTY

(75) Inventors: Dean M. J. Acker, Warsaw, IN (US); Robert D Krebs, Warsaw, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 1308 days.

(21) Appl. No.: 11/105,080

(22) Filed: Apr. 13, 2005

(65) Prior Publication Data

US 2005/0177172 A1 Aug. 11, 2005

Related U.S. Application Data

(60) Division of application No. 10/357,948, filed on Feb. 4, 2003, now Pat. No. 6,991,656, which is a continuation-in-part of application No. 10/053,931, filed on Jan. 22, 2002, now Pat. No. 6,953,480, which is a continuation-in-part of application No. 09/558,044, filed on Apr. 26, 2000, now Pat. No. 6,676,706.

(51) Int. Cl.
*A61B 17/58* (2006.01)
(52) U.S. Cl. .................. 606/91; 606/99; 623/22.12
(58) Field of Classification Search ............ 606/79–81, 606/91, 96, 99; 623/18.11, 20.35, 20.36, 623/22.11, 22.12, 22.15, 22.21, 22.23, 22.24–22.39, 623/22.4, 22.41–22.47, 23.11, 23.15, 23.16–23.39, 623/908
See application file for complete search history.

(56) References Cited

U.S. PATENT DOCUMENTS

| | | | |
|---|---|---|---|
| 3,585,994 A | 6/1971 | Huggler et al. |
| 3,829,904 A | 8/1974 | Ling et al. |
| 3,955,568 A | 5/1976 | Neufeld |
| 4,135,517 A | 1/1979 | Reale |
| 4,177,813 A | 12/1979 | Miller et al. |
| 4,341,220 A | 7/1982 | Perry |
| 4,410,295 A | 10/1983 | Ersoy et al. |
| 4,552,136 A | 11/1985 | Kenna |
| 4,716,894 A | 1/1988 | Lazzeri et al. |
| 4,765,328 A | 8/1988 | Keller et al. |

(Continued)

FOREIGN PATENT DOCUMENTS

DE 20021494 U1 3/2001

(Continued)

OTHER PUBLICATIONS

Zimmer, Trilogy Acetabular System: Surgical Technique, 97-6200-102, 2002.

(Continued)

*Primary Examiner*—Eduardo C Robert
*Assistant Examiner*—Lynnsy Schneider
(74) *Attorney, Agent, or Firm*—Baker & Daniels LLP

(57) ABSTRACT

A method and apparatus for performing a minimally invasive total hip arthroplasty including an acetabular cup inserter is provided. The cup inserter is utilized for securing a prosthetic acetabular component thereto for implantation into a hip joint. The acetabular cup inserter includes a frame having an offset frame leg to allow for placement of an acetabular cup in the correct anteversion and abduction without interference from soft tissue.

13 Claims, 46 Drawing Sheets

U.S. PATENT DOCUMENTS

| | | | |
|---|---|---|---|
| 4,903,692 A | 2/1990 | Reese | |
| 4,905,148 A | 2/1990 | Crawford | |
| 5,007,936 A | 4/1991 | Woolson | |
| 5,037,424 A | 8/1991 | Aboczsky | |
| 5,047,034 A | 9/1991 | Sohngen | |
| 5,061,270 A | 10/1991 | Aboczky | |
| 5,064,427 A | 11/1991 | Burkinshaw | |
| 5,086,401 A | 2/1992 | Glassman et al. | |
| 5,089,003 A | 2/1992 | Fallin et al. | |
| 5,089,004 A | 2/1992 | Averill et al. | |
| 5,147,366 A | 9/1992 | Arroyo et al. | |
| 5,152,792 A | 10/1992 | Watkins et al. | |
| 5,156,626 A | 10/1992 | Broderick et al. | |
| 5,190,550 A | 3/1993 | Miller et al. | |
| 5,242,455 A | 9/1993 | Skeens et al. | |
| 5,251,127 A | 10/1993 | Raab | |
| 5,284,483 A | 2/1994 | Johnson | |
| 5,299,288 A | 3/1994 | Glassman et al. | |
| 5,305,203 A | 4/1994 | Raab | |
| 5,320,625 A | 6/1994 | Bertin | |
| 5,324,366 A | 6/1994 | Kiel et al. | |
| 5,339,803 A | 8/1994 | Mayzels et al. | |
| 5,342,363 A | 8/1994 | Richelsoph | |
| 5,360,446 A | 11/1994 | Kennedy | |
| 5,364,403 A | 11/1994 | Petersen et al. | |
| 5,383,454 A | 1/1995 | Bucholz | |
| 5,389,101 A | 2/1995 | Heilbrun et al. | |
| 5,408,409 A | 4/1995 | Glassman et al. | |
| 5,474,560 A | 12/1995 | Rohr, Jr. | |
| 5,490,852 A | 2/1996 | Azer et al. | |
| 5,507,814 A | 4/1996 | Gilbert et al. | |
| 5,507,830 A | 4/1996 | DeMane et al. | |
| 5,517,990 A | 5/1996 | Kalfas et al. | |
| 5,534,006 A * | 7/1996 | Szabo et al. | 606/100 |
| 5,540,692 A | 7/1996 | Tidwell | |
| 5,571,111 A | 11/1996 | Aboczky | |
| 5,578,037 A | 11/1996 | Sanders et al. | |
| 5,584,837 A * | 12/1996 | Petersen | 606/91 |
| 5,607,431 A | 3/1997 | Dudasik et al. | |
| 5,616,147 A | 4/1997 | Gadelius | |
| 5,624,447 A | 4/1997 | Myers | |
| 5,658,294 A * | 8/1997 | Sederholm | 606/91 |
| 5,676,673 A | 10/1997 | Ferre et al. | |
| 5,682,886 A | 11/1997 | Delp et al. | |
| 5,683,395 A | 11/1997 | Mikhail | |
| 5,690,635 A | 11/1997 | Matsen, III et al. | |
| 5,720,750 A | 2/1998 | Koller et al. | |
| 5,738,586 A * | 4/1998 | Arriaga | 464/106 |
| 5,741,215 A | 4/1998 | D'Urso | |
| 5,748,767 A | 5/1998 | Raab | |
| 5,769,092 A | 6/1998 | Williamson, Jr. | |
| 5,776,064 A | 7/1998 | Kalfas et al. | |
| 5,788,704 A | 8/1998 | Timperly | |
| 5,800,352 A | 9/1998 | Ferre et al. | |
| 5,803,089 A | 9/1998 | Ferre et al. | |
| 5,806,518 A | 9/1998 | Mittelstadt | |
| 5,814,050 A | 9/1998 | Benson | |
| 5,817,105 A | 10/1998 | VanDerBrug | |
| 5,824,083 A | 10/1998 | Draenert | |
| 5,824,085 A | 10/1998 | Sahay et al. | |
| 5,829,444 A | 11/1998 | Ferre et al. | |
| 5,834,759 A | 11/1998 | Glossop | |
| 5,871,018 A | 2/1999 | Delp et al. | |
| 5,871,445 A | 2/1999 | Bucholz | |
| 5,879,353 A | 3/1999 | Terry | |
| 5,879,406 A | 3/1999 | Lilley | |
| 5,885,295 A | 3/1999 | McDaniel et al. | |
| 5,921,992 A | 7/1999 | Costales | |
| 5,935,141 A | 8/1999 | Weldon | |
| 5,950,629 A | 9/1999 | Taylor et al. | |
| 5,951,561 A | 9/1999 | Pepper et al. | |
| 5,954,727 A | 9/1999 | Collazo | |
| 5,997,582 A | 12/1999 | Weiss | |
| 6,010,535 A | 1/2000 | Shah | |
| 6,027,505 A | 2/2000 | Peter et al. | |
| 6,050,266 A | 4/2000 | Benetti et al. | |
| 6,063,088 A | 5/2000 | Winslow | |
| 6,113,605 A | 9/2000 | Storer | |
| 6,120,508 A | 9/2000 | Grunig et al. | |
| 6,187,006 B1 | 2/2001 | Keller | |
| 6,264,698 B1 | 7/2001 | Lawes et al. | |
| 6,338,716 B1 | 1/2002 | Hossack | |
| 6,395,005 B1 | 5/2002 | Lovell | |
| 6,488,715 B1 | 12/2002 | Clayton | |
| 6,490,475 B1 | 12/2002 | Seeley | |
| 6,497,134 B1 | 12/2002 | Faul et al. | |
| 6,626,913 B1 * | 9/2003 | McKinnon et al. | 606/99 |
| 6,991,656 B2 | 1/2006 | Mears | |
| 7,166,114 B2 | 1/2007 | De La Barrera et al. | |
| 7,326,215 B2 * | 2/2008 | Myers et al. | 606/80 |
| 2001/0014828 A1 | 8/2001 | Yoon | |
| 2001/0014829 A1 | 8/2001 | Yoon | |
| 2001/0016780 A1 | 8/2001 | San | |
| 2002/0128659 A1 | 9/2002 | Michelson | |
| 2003/0050645 A1 * | 3/2003 | Parker et al. | 606/99 |
| 2003/0153829 A1 | 8/2003 | Sarin et al. | |
| 2003/0158559 A1 | 8/2003 | Diaz | |
| 2003/0195517 A1 | 10/2003 | Michelson | |
| 2003/0220698 A1 | 11/2003 | Mears et al. | |
| 2003/0229356 A1 * | 12/2003 | Dye | 606/99 |
| 2004/0034358 A1 | 2/2004 | Michelson | |
| 2004/0172036 A1 | 9/2004 | Dye | |
| 2005/0038443 A1 * | 2/2005 | Hedley et al. | 606/91 |
| 2005/0085823 A1 | 4/2005 | Murphy | |
| 2005/0154296 A1 | 7/2005 | Lechner et al. | |
| 2005/0177172 A1 | 8/2005 | Acker | |
| 2005/0187562 A1 | 8/2005 | Grimm | |
| 2005/0203535 A1 | 9/2005 | Parry et al. | |
| 2006/0030947 A1 | 2/2006 | Mears | |

FOREIGN PATENT DOCUMENTS

| | | |
|---|---|---|
| EP | 0207873 | 12/1989 |
| EP | 0380309 | 8/1990 |
| EP | 0558203 | 1/1993 |
| EP | 0558203 | 9/1993 |
| EP | 0940127 A | 9/1999 |
| EP | 0940128 A | 9/1999 |
| EP | 0956824 | 11/1999 |
| EP | 1149562 | 10/2001 |
| EP | 1258233 | 11/2002 |
| EP | 0956824 | 3/2004 |
| EP | 1149562 | 2/2006 |
| EP | 1149562 | 8/2006 |
| FR | 1041311 | 8/1951 |
| FR | 1041311 | 10/1953 |
| FR | 2721192 | 12/1995 |
| FR | 2742038 | 6/1997 |
| FR | 2775889 | 6/1999 |
| FR | 2775889 | 9/1999 |
| JP | 59-200643 A | 11/1984 |
| JP | 04-044758 A | 2/1992 |
| JP | 04-044758 A | 2/1992 |
| JP | 10-328205 A | 12/1998 |
| WO | WO01/67979 A1 | 9/2001 |
| WO | 03065906 | 8/2003 |
| WO | WO03/065906 | 8/2003 |

OTHER PUBLICATIONS

Zimmer, Trilogy Acetabular System: Evolution Through Proven Clinical Experience, 97-6200-101, 1998.

Zimmer VerSys Hip System: VerSys Cemented, Cemented Plus, and Cemented CT Hip Prostheses: Surgical Technique for Primary Hip Arthroplasty, 97-7852-02, 1997.

The Office Action mailed May 12, 2009 in related Japanese application No. 2004-028295.
The Office Action mailed Aug. 18, 2009 in related Japanese application No. 2001-129998.
The Office Action mailed Aug. 19, 2008 in related Japanese application No. 2001-129998.
The European Office Action mailed Feb. 28, 2006 in related European application No. 04000194.3.
The Response filed Jun. 22, 2006 to the European Office Action mailed Feb. 28, 2006 in related European application No. 04000194.3.
The European Office Action mailed Aug. 30, 2005 in related European application No. 04000194.3.
The Response filed Jan. 6, 2006 to the European Office Action mailed Aug. 30, 2005 in related European application No. 04000194.3.
The European Search published Apr. 14, 2004 in related European application No. 04000194.3.
The Canadian Office Action mailed Jun. 18, 2009 in related Canadian application No. 2,343,926.
The Response filed Feb. 19, 2009 to the Canadian Office Action mailed Aug. 22, 2008 in related Canadian application No. 2,343,926.
The Canadian Office Action mailed Aug. 22, 2008 in related Canadian application No. 2,343,926.
The European Office Action mailed Feb. 16, 2009 in related European application No. 04250522.2.
The Response filed Aug. 16, 2009 to the European Office Action mailed Feb. 16, 2009 in related European application No. 04250522.2.
The Elevated-Rim Acetabular Liner in Total Hip Arthroplasty: Relationship to Postoperative Dislocation by T.K. Cobb, M.D. et al., Jan. 1996.
Displacement after Total Hip-Replacement Arthroplasties by George E. Lewinnek, M.D. et al., Mar. 1978.
Range of Motion in Contemporary Total Hip Arthroplasty by Robert J. Krushell, M.D. et al., Jun. 1991.
Elevated-Rim Acetabular Components by Robert J. Krushell, M.D. et al., Oct. 1991.
Range of Motion Studies for Total Hip Replacements by Harlan C. Amstutz, M.D. et al., Sep. 1975.
Dislocation After Total Hip Arthroplasty by Donald E. McCollum, M.D. et al., Dec. 1990.
Finite Element Modeling of Dislocation Propensity in Total Hip Arthroplasty by T.A. Maxian et al., Feb. 19-22, 1996.
Femoral Head Containment in Total Hip Arthroplasty, Standard v. Extended Lip Liners by T.D. Brown et al., Feb. 19-22, 1996.
An Image-Directed Robotic System for Precise Orthopaedic Surgery by Russell H. Taylor et al., Jun. 1994.
Techniques for Fast and Accurate Intrasurgical Registration by David A. Simon et al., 1995.
Computer-Assisted Knee Anterior Cruciate Ligament Reconstruction: First Clinical Tests by Vincent Dessenne et al., 1995.
Comparison of Relative Accuracy Between a Mechanical and an Optical Postion Tracker for Image-Guided Neurosurgery by Robert Rohling et al., 1995.
Computer-Assisted Spine Surgery: A Technique for Accurate Transpedicular Screw Fixation Using CT Data and a 3-D Optical Localizer by S. Lavallee et al., 1995.
Etude Du Cotyle Non Scelle De Bousquet Dans Cent Protheses Totales De Hanche Hybrides by J.H. Aubriot et al., 1993.
La Tige Vissee De Bousquet Dans L'Arthroplastie Totale De Hanche En Premiere Intention by M.H. Fessy et al., 1993.
Anatomy-based Registration for Computer-Integrated Surgery by Ali Hamadeh et al., Apr. 3-6, 1995.
BIAS Total Hip System Surgical Technique for Premary Hip Arthroplasty and Revision of Hip Arthroplasty with Bone Grafting by Ramon B. Gustilo, M.D. et al.
Kenneth A. Krackow, M.D. et al.: "Clinical Experience with a Triradiate Exposure of the Hip for Difficult Total Hip Arthroplasty", pp. 267-278, The Journal of Arthroplasty, Sep. 1988.
Pasquale Petrera, M.D. et al.: "Revision Total Hip Arthroplasty with a Retroperitoneal Approach to the Iliac Vessels", The Journal of Arthroplasty, 1996, pp. 704-708.

G. Lang et al.: "Arthroplasty of the hip by cemented coupled cups", 1978, Masson, Paris, Nouv. Presse Med., pp. 3925-3928.
J.C. Bos et al.: "The surgcal anatomy of the superior gluteal nerve and anatomical radiologic bases of the direct lateral approach to the hip" Surgical Radiologic Anatomy, 1994, pp. 253-258.
Mansho Itokazu et al.: "Exposure of the Hip by Anterior Osteotomy of the Greater Trochanter", Hospital for Joint Diseases Bulletin, 1998, pp. 159-161.
John J. Joyce, III et al.: "The Anatomical Basis of the Hip Joint Exposures", No. 98, Jan.-Feb. 1974, pp. 27-31.
"Surgery of the Hip Joint", Edited by Raymond G. Tronzo, M.D., Copyright 1873, Lea & Febiger, Philadelphia.
Journal of the Japanese Orthopedic Association 75 (2), 2001: Kazuo Kaneko et al., "Total Hip Arthroplasty and Femoral Head Prosthetic Replacement Using Mini Incisions" and Shoichi Shinoda et al., "Joint Use of Acetabular Abduction Osteotomy and Anterior Trochantic Slide for Osteoarthritis of the Hip Joint".
Ralph Lusskin et al. "Combined Anterior and Posterior Approach to the Hip Joint in Reconstructive and Complex Arthroplasty", Department of Orthopedic Surgery, New York University Medical Center, New York, NY Dec. 1988, pp. 313-322.
James B. Stiehl et al.: "Extensile Triradiate Approach for Complex Acetabular Reconstruction in Total Hip Arthroplasty", Clinical Orthopaedics and Related Research, 1993, pp. 162-169.
Richard H. Walker, M.D.: "Pelvic Reconstruction/Total Hip Arthroplasty for Metastatic Acetabular Insufficiency", Clinical Orthopaedics and Related Research, 1993, pp. 170-175.
Joel M. Matta, M.D.: "Operative Treatment of Acetabular Fractures Through the Ilioinguinal Approach, a 10=year Perspective", Clinical Orthopaedics and Related Research, 1994, pp. 10-19.
http://www.orthoteers.co.uk, "Pelvis & Acetabulun-Surgical Approaches", 3 pages, Jan. 2001.
http://www.orthoteers.co.uk, "Hip-Surgical Approaches", 9 pages, Jan. 2001.
Video Tape—Cementless Ceramic Hip Replacement: The Anterior Approach, Kristaps Keggi, M.D., Jun. 1, 1985.
Curriculum Vitae of Dr. Kristaps Juris Keggi, Jul. 8, 2003.
Article—Anterior Approach to Hip Arthroplasty, Terry R. Light, M.D., et al., Clinical Orthopaedics and Related Research, pp. 225-260.
Reference—"The Yale Journal of Biology and Medicine", vol. 66, No. 3, May-Jun. 1993, pp. 243-256.
Article—"Superior Mesenteric Vein Tear with Total Hip Arthroplasty", Jonathan N. Grauer, M.D., et al., The Journal of Arthroplasty vol. 16, No. 5, 2001, pp. 671-673.
Article—"Total Hip Arthroplasty Using the Sweymuller Stem Implanted Without Cement", Michael H. Huo, M.D., et al., The Journal of Arthroplasty vol. 10, No. 6, 1995, pp. 793-799.
Article—"Total Hip Replacement Update: Cement v Cementless Arthroplasty", Ronald W. Lindsey, M.D., et al., Connecticut Medicine, vol. 52, No. 7, Jul. 1988, pp. 399-401.
Article—"Primary Ceramic Hip replacement: A Prospective Study of 119 Hips", Scott A. Hoffinger, M.D., et al., Orthopedics, May 1991, vol. 14, pp. 523-531.
Article—"Anatomy and Osteotomy of the Greater Trochanter", John P. Fulkerson, M.D., et al., Archives of Surgery, vol. 114, Jan. 1979, pp. 19-21.
Article—"One-Stage Bilateral Total Hip Arthroplasty in Patients > 75 Years", Marc A. Weinstein, M.D., et al., Orthopedics, vol. 25, No. 2, Feb. 2002, pp. 153-156.
Article—"A Comparison of the Cost Effectiveness of One-Stage Versus Two-Stage Bilateral Total Hip Replacement", Mark Lorenze, M.D., et al., Orthopedics, vol. 21, No. 12, Dec. 1998, pp. 1249-1252.
Surgical Exposure and Cement Removal in Revision Total Hip Arthroplasty, Thomas H. Mallory, Seminars in Arthroplasty, col. 3, No. 4, Oct. 1992, pp. 257-263.
Mini-Incision for Total Hip Arthroplasty, John M. Wright, M.D., et al., Orthopedic Special Edition, vol. 7, No. 2 of 2, 2001, pp. 18-20.
Robotics for Surgery, Robert D. Howe et al., Annual Rev. Biomed. Eng. 1999, pp. 211-240.
Minimally Invasive Total Hip Arthroplasty, George F. Chimento, M.D., et al., Operative Techniques in Orthopaedics, vol. 11, No. 4, Oct. 2001, pp. 270-273.

Application of Arthroplasty Principles to Canine Cemented Total Hip Replacement, Kurt S. Schultz, Veterinary Surgery, 2000, pp. 578-593.

Anterior Approach to Resurfacing Arthroplasty of the Hip: a Preliminary Experience, Robert P. Hendrikson, M.D., et al., Connecticut Medicine, Mar. 1983, vol. 47, No. 3, pp. 131-135.

A New Era of Minimally Invasive Surgical Approaches for THA, Timothy McTighe, Ph.D., Joint Implant Surgery and Research Foundatino, Dec. 2002, pp. 2-7.

* cited by examiner

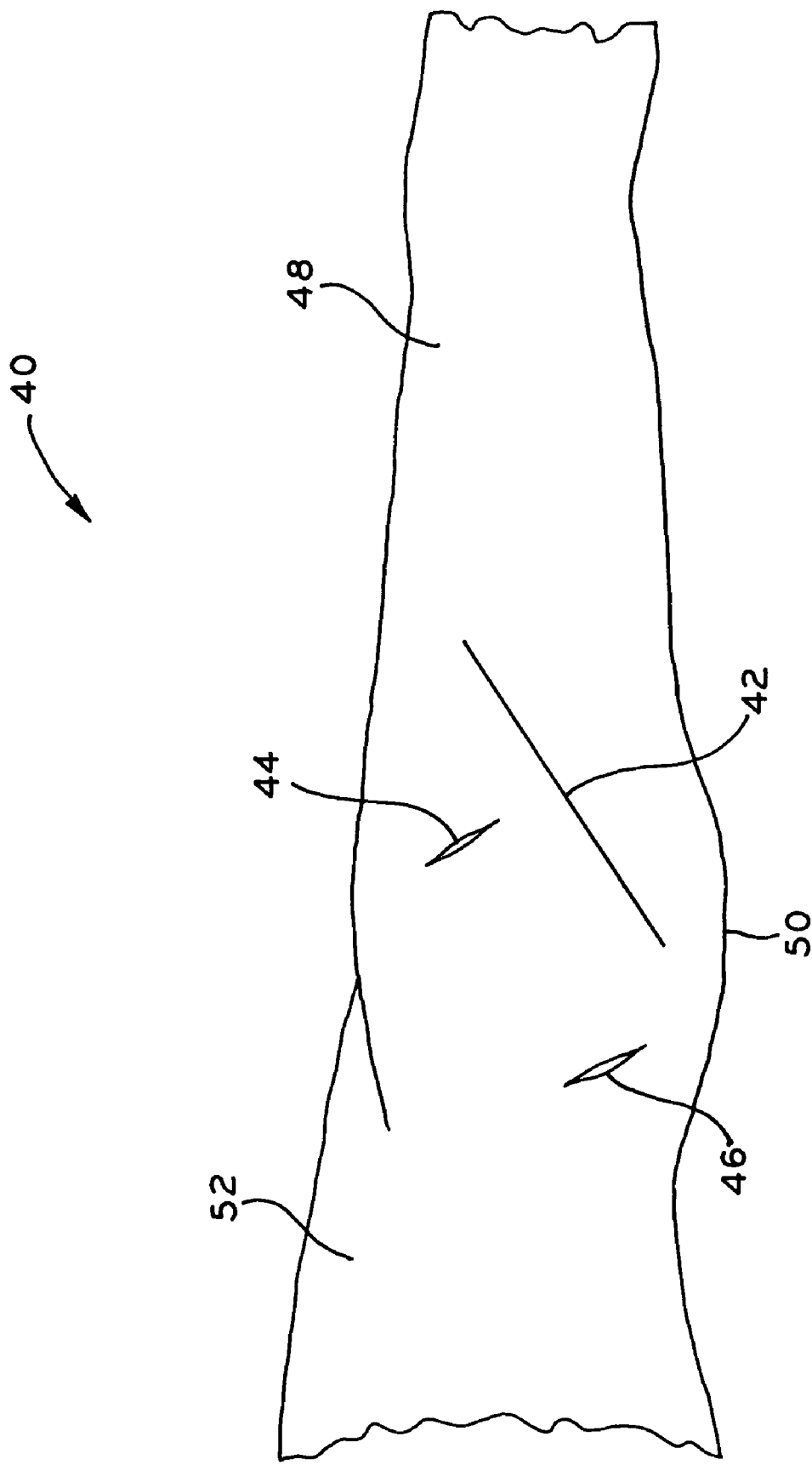
FIG_1A

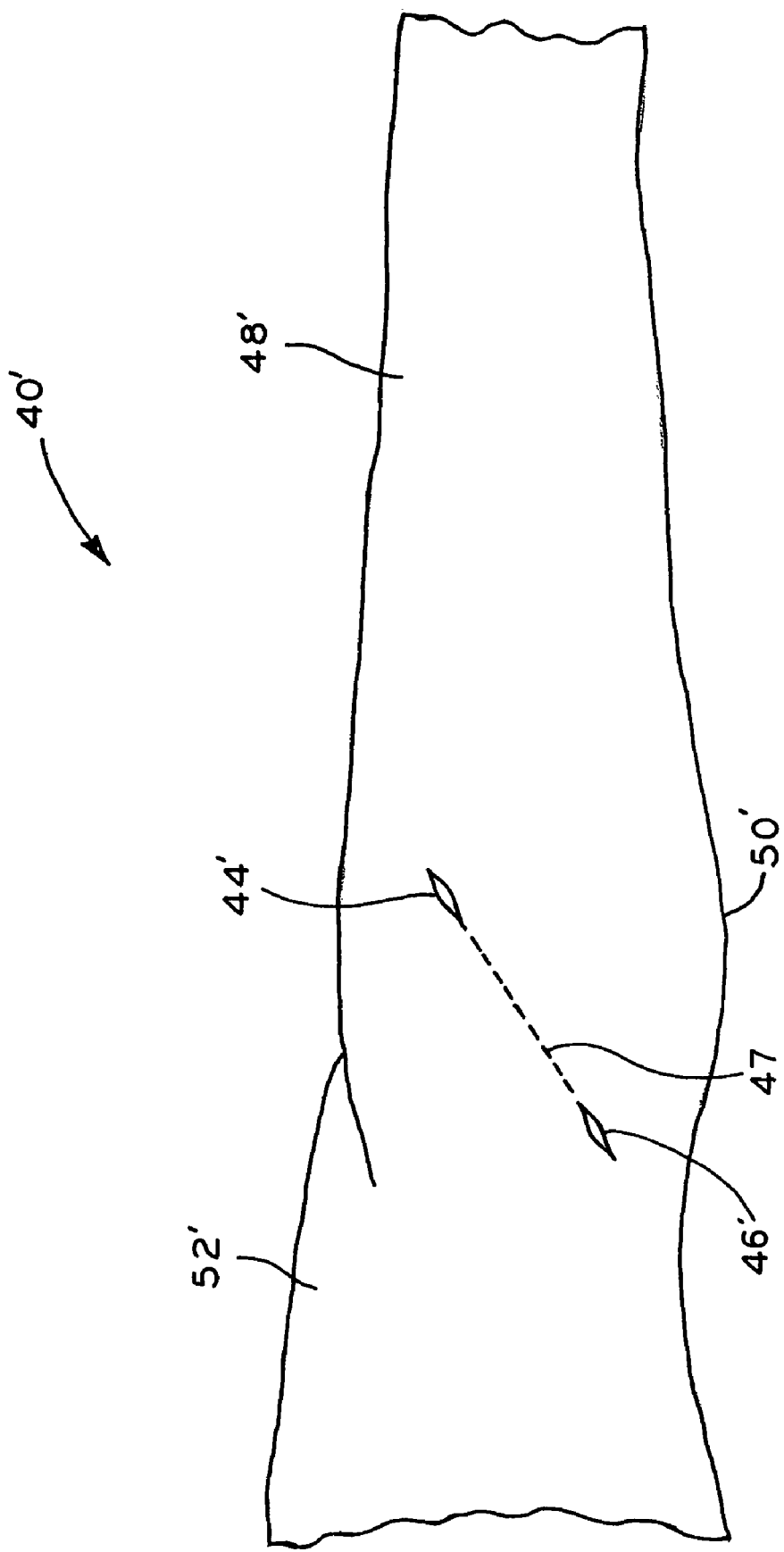

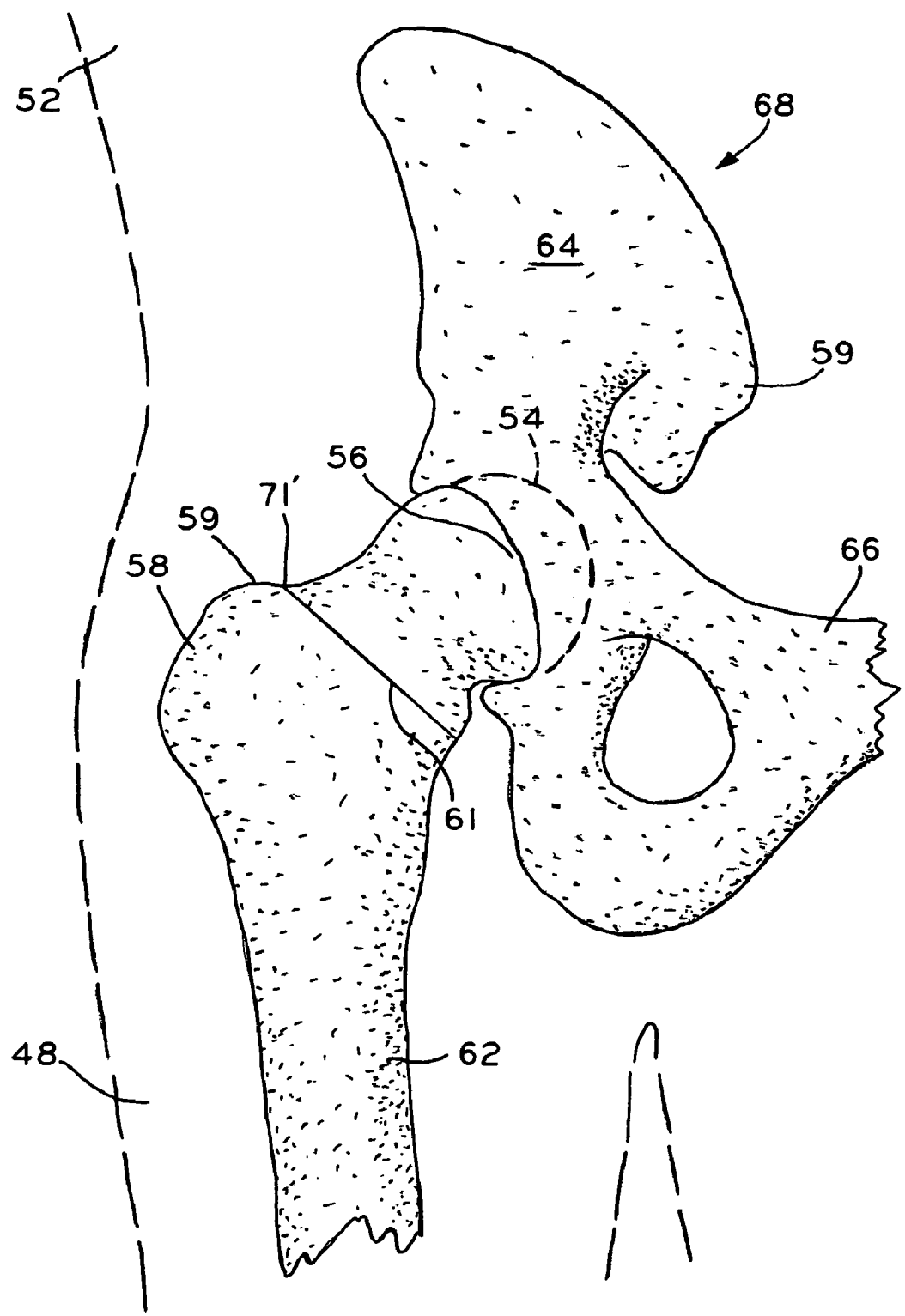
FIG_2B

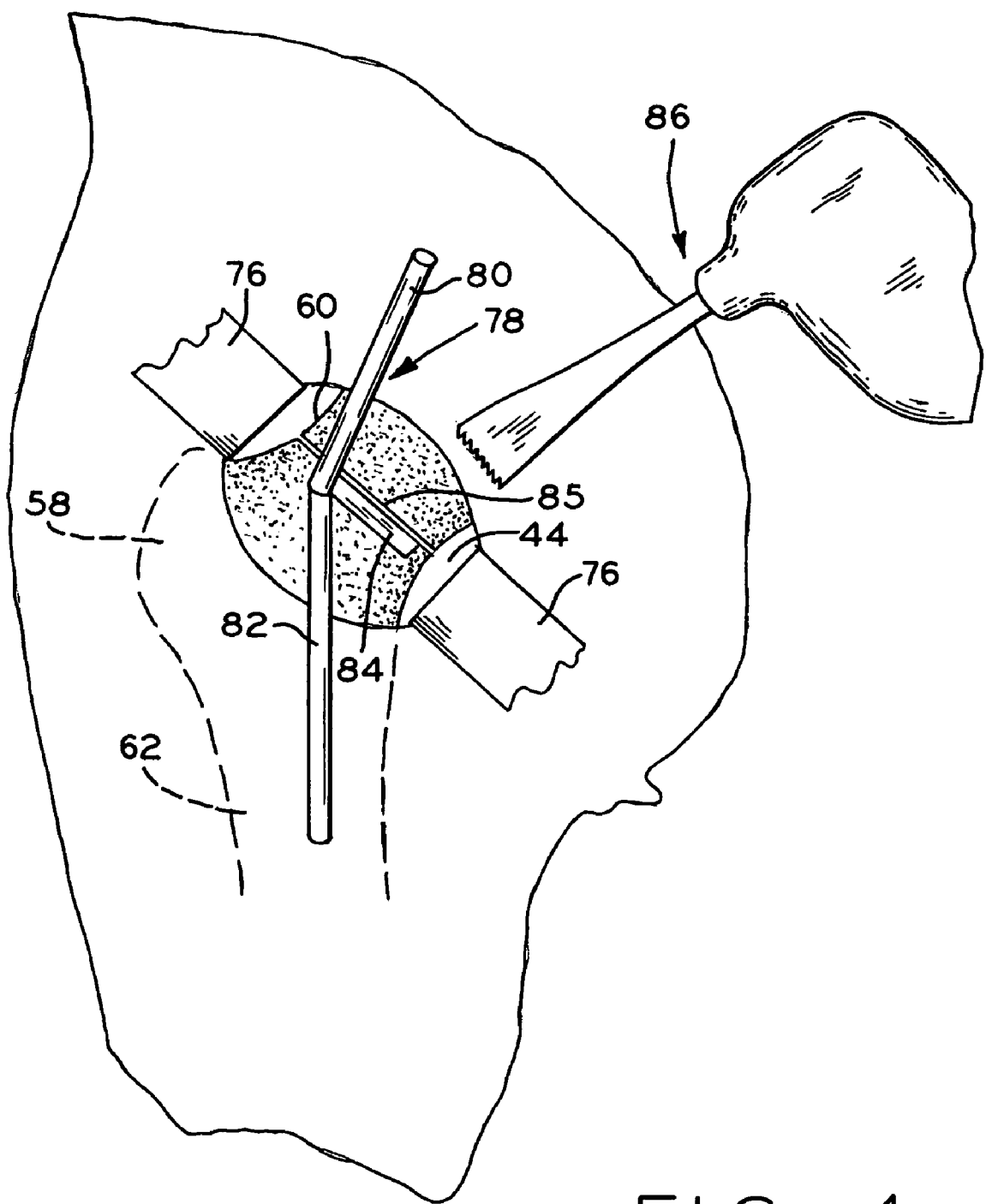
FIG_4

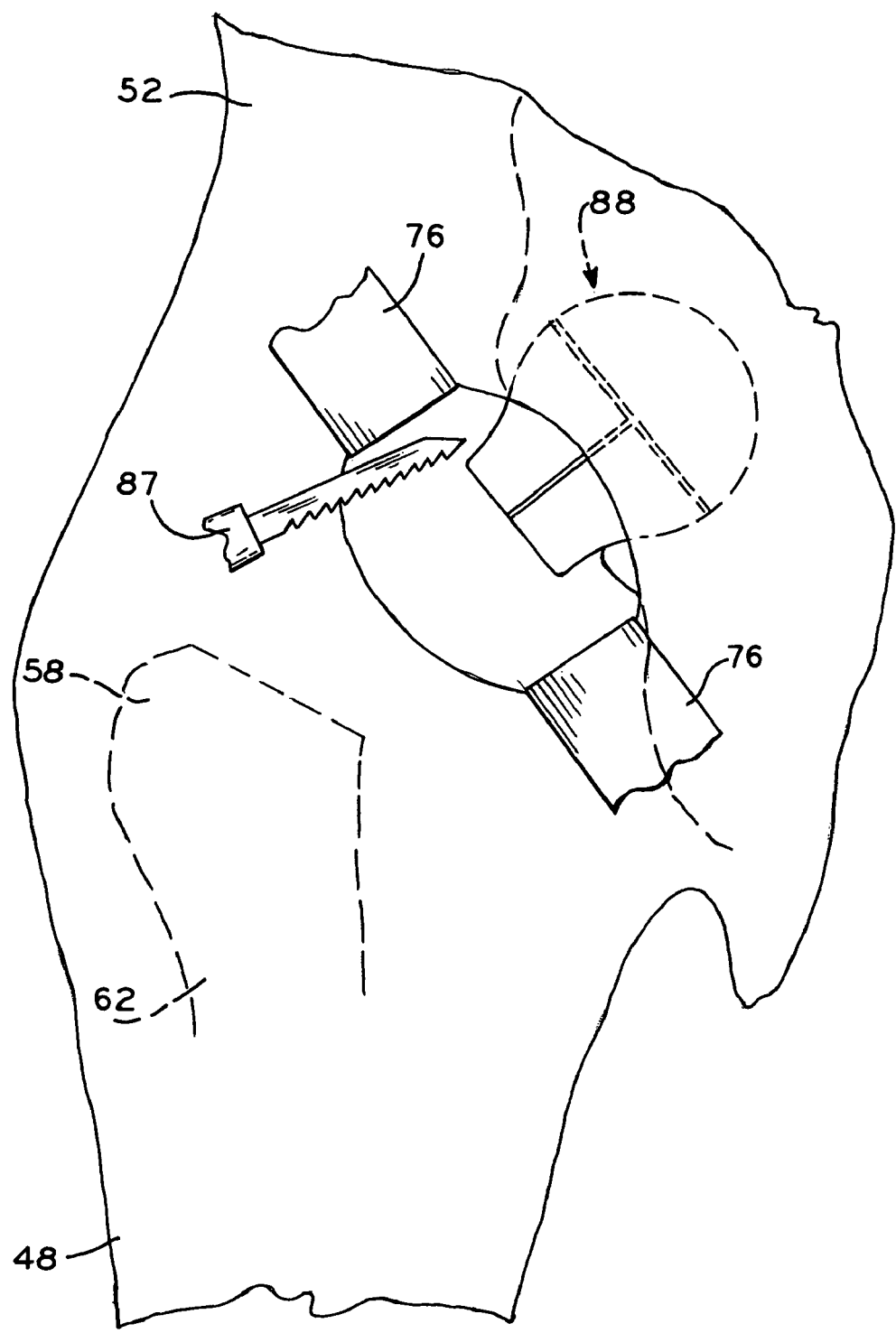
FIG_6A

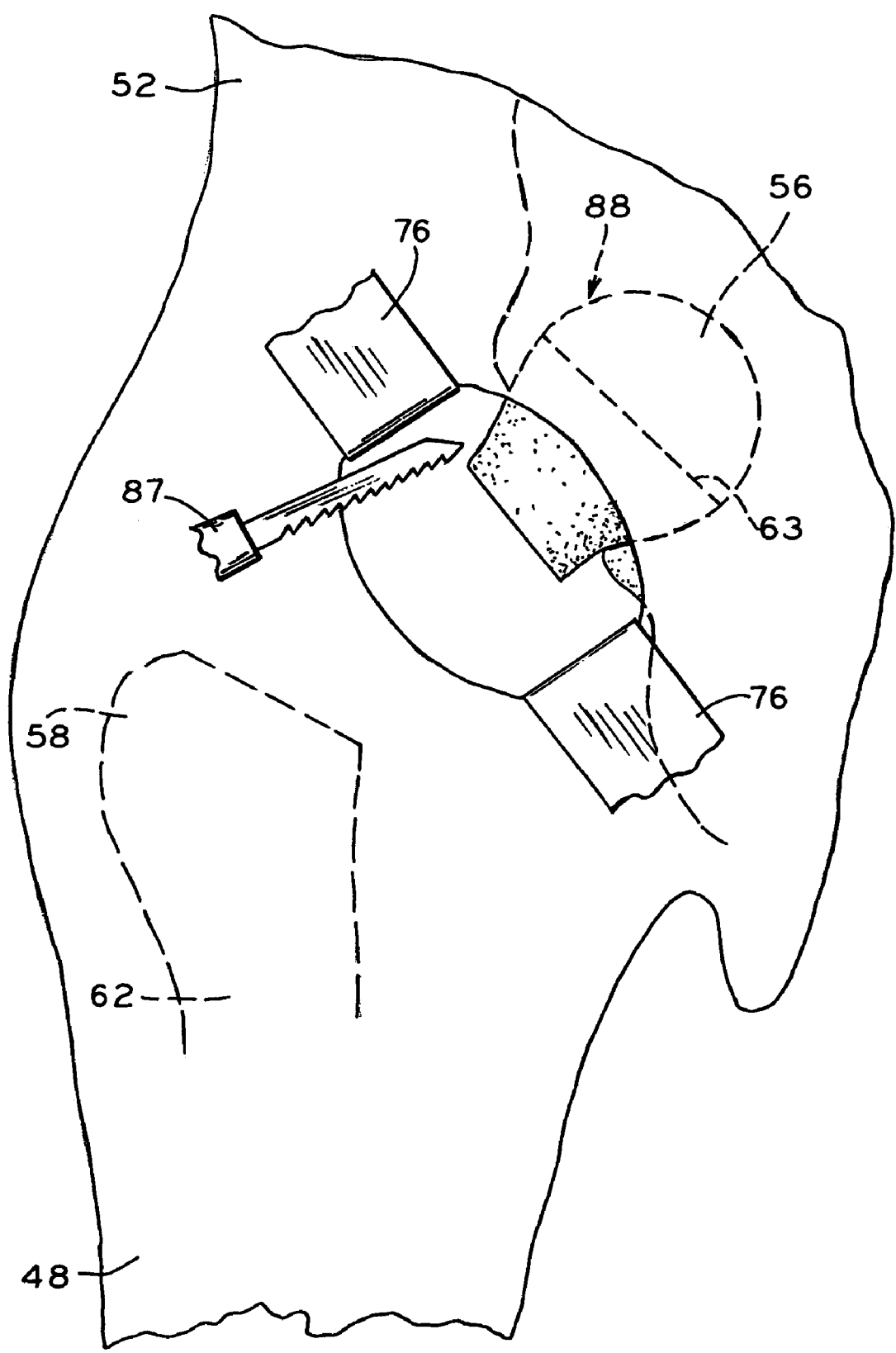
FIG_6B

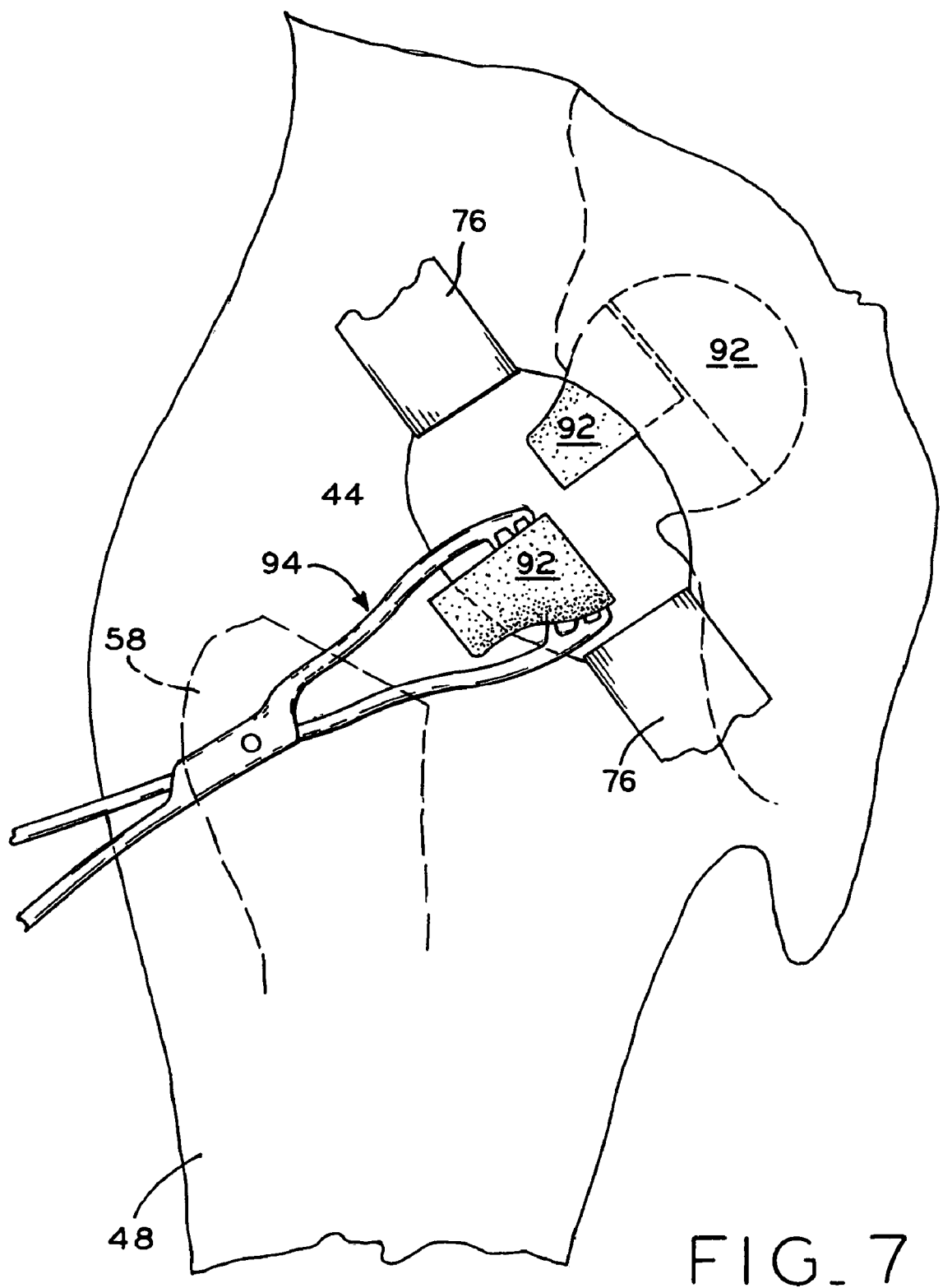
FIG_7

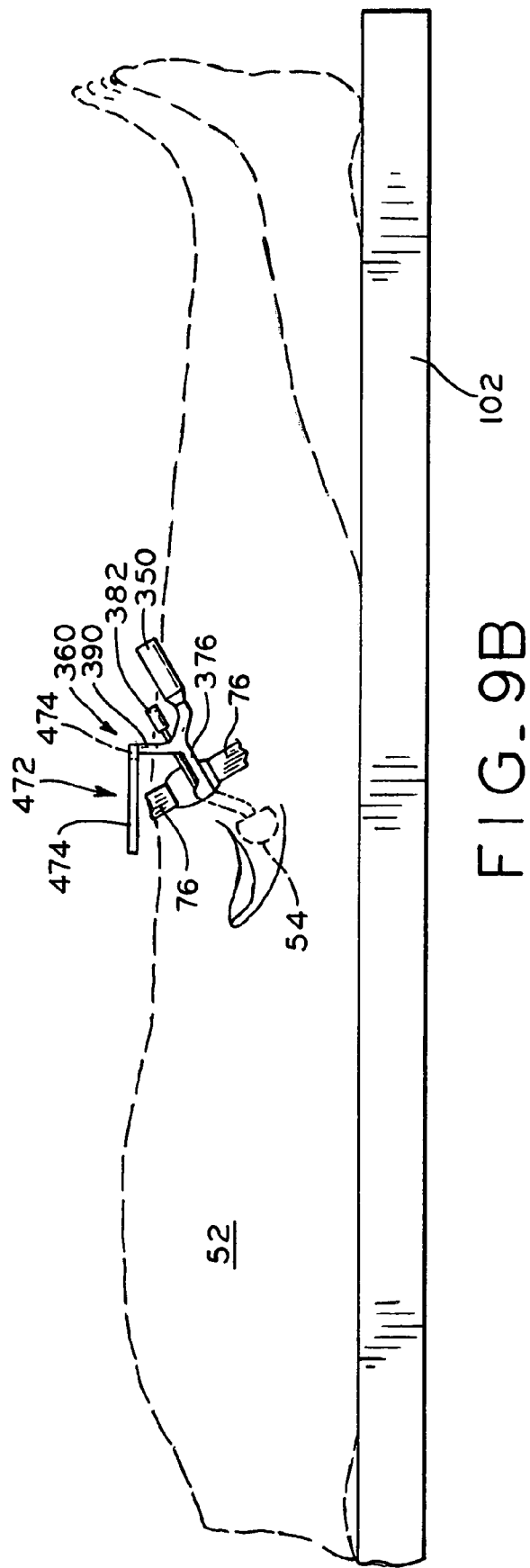

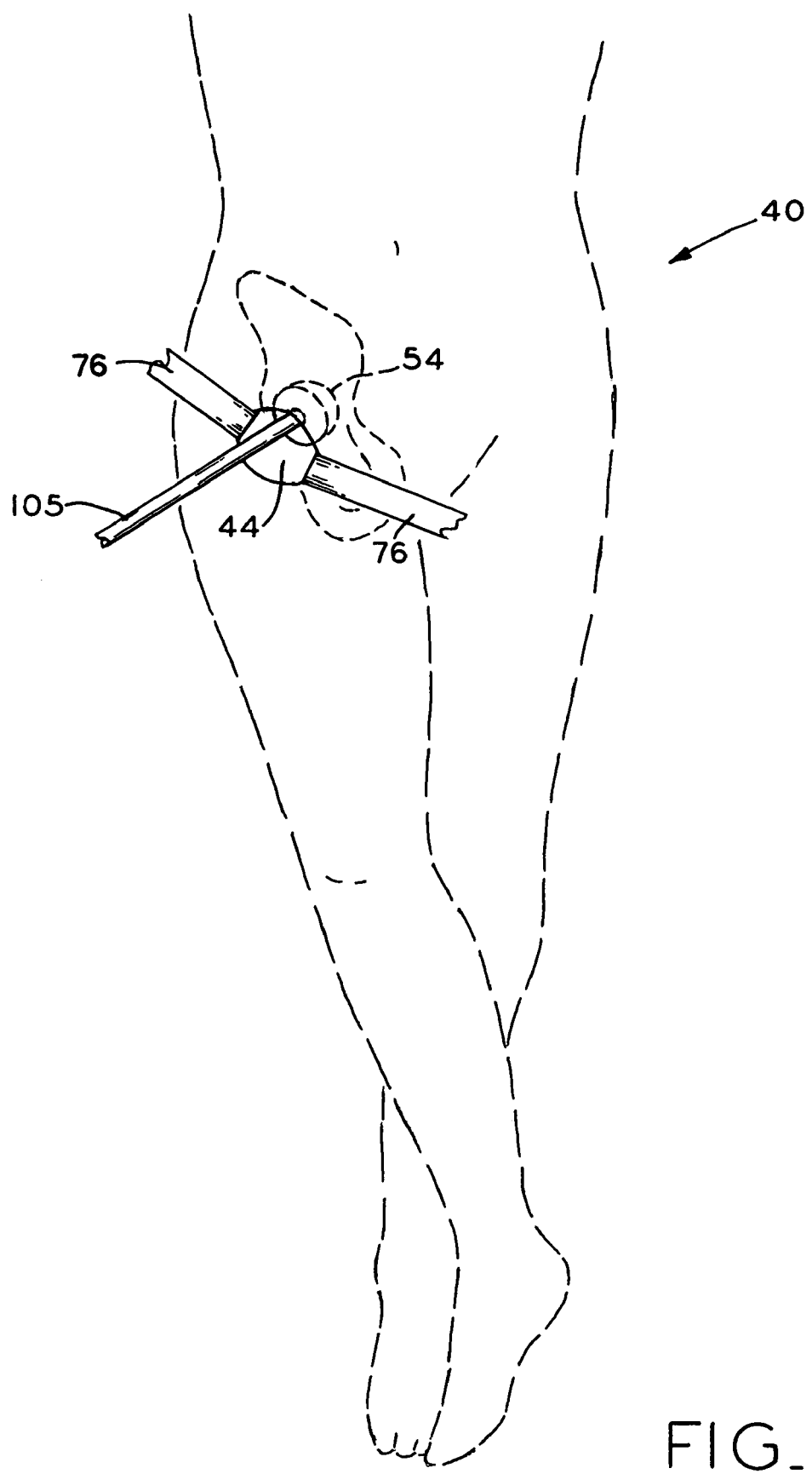
FIG_10

FIG._15

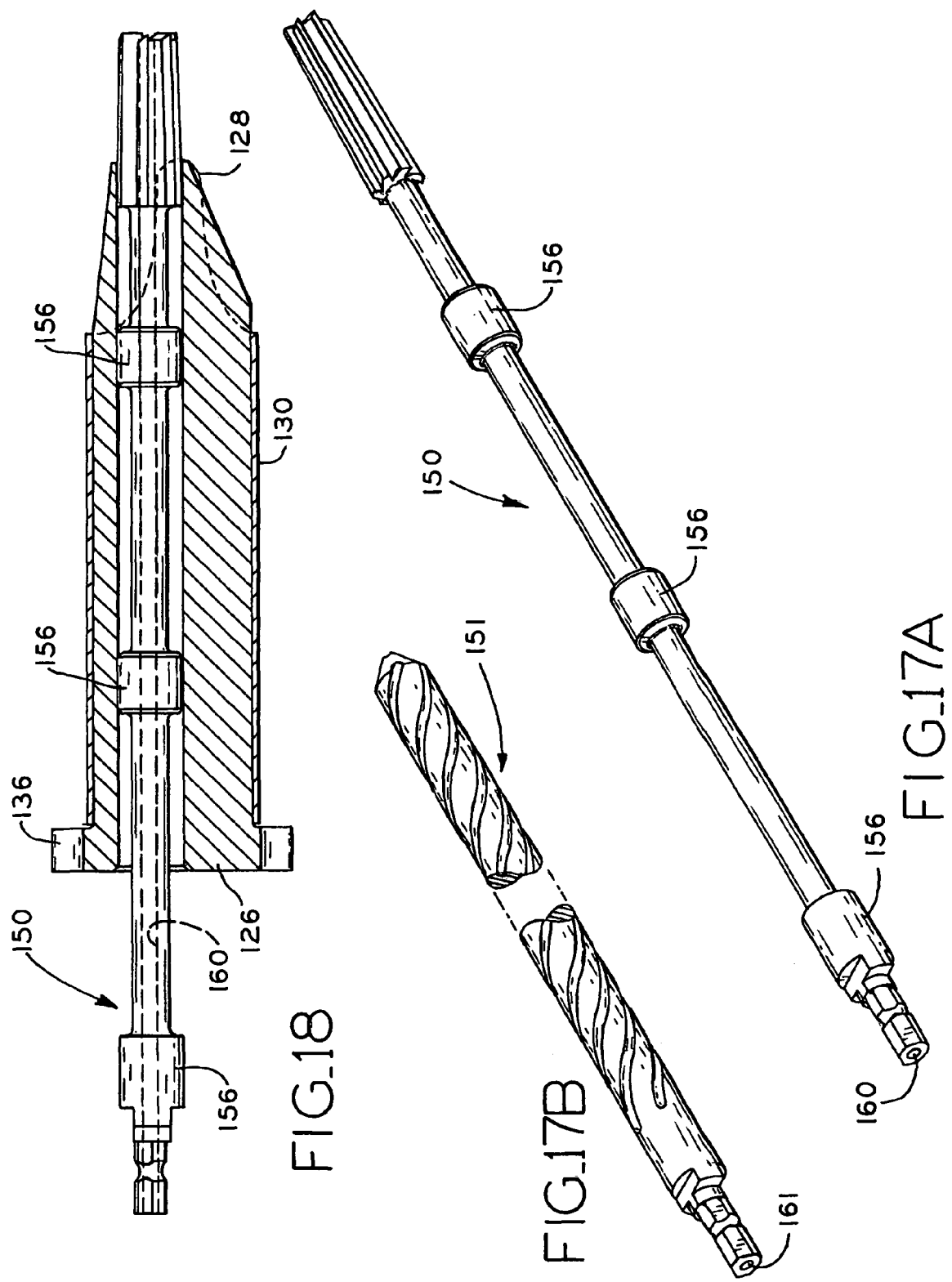

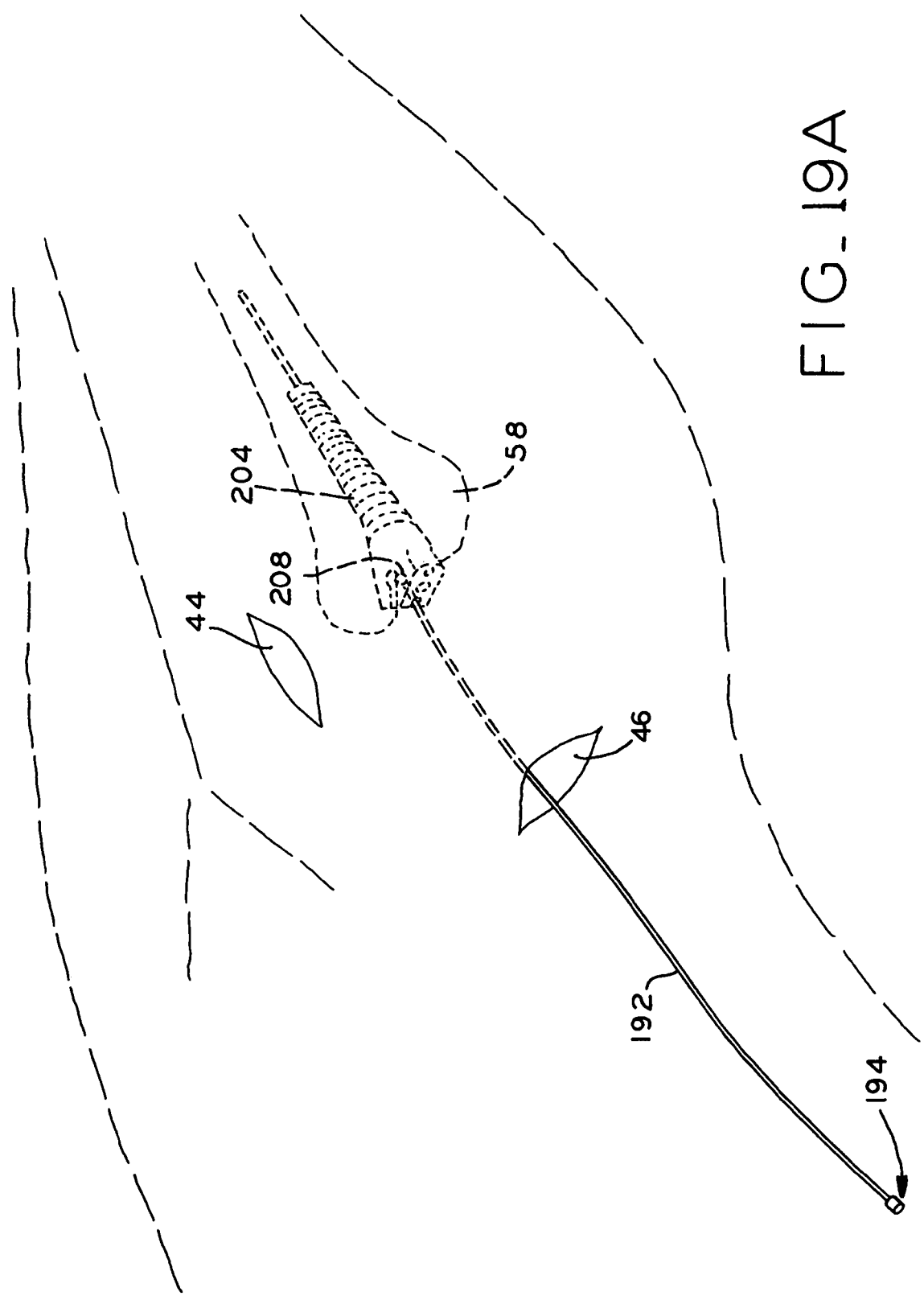
FIG_19A

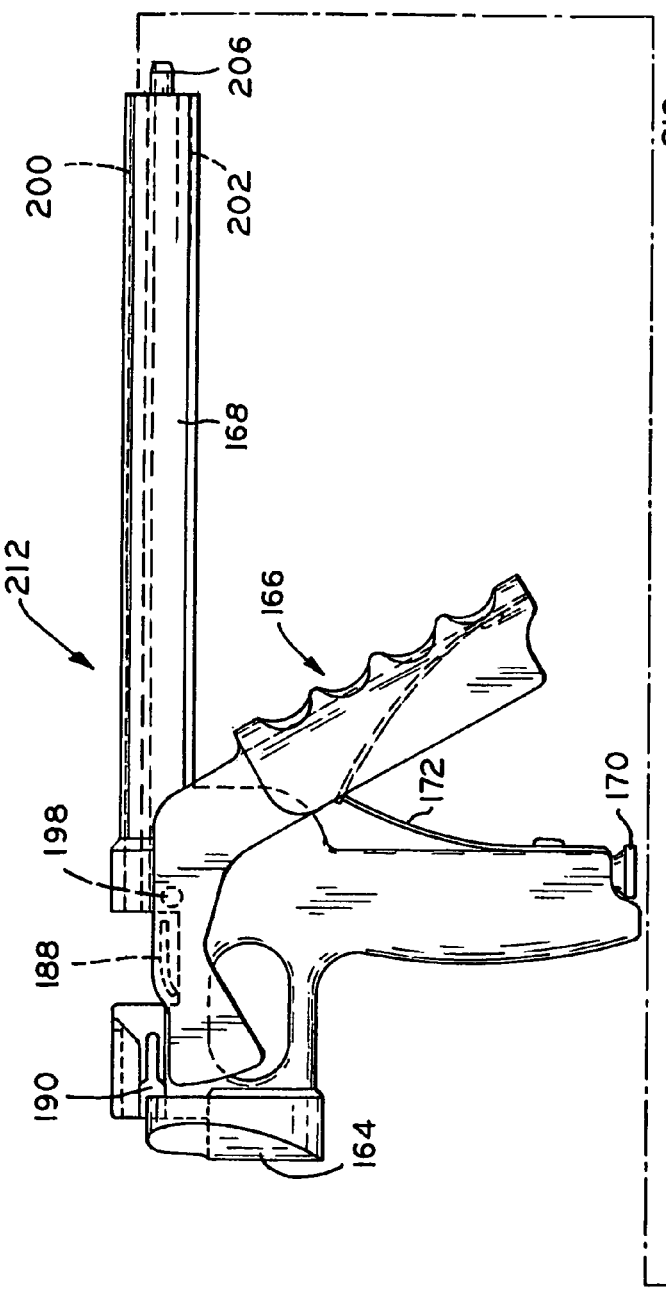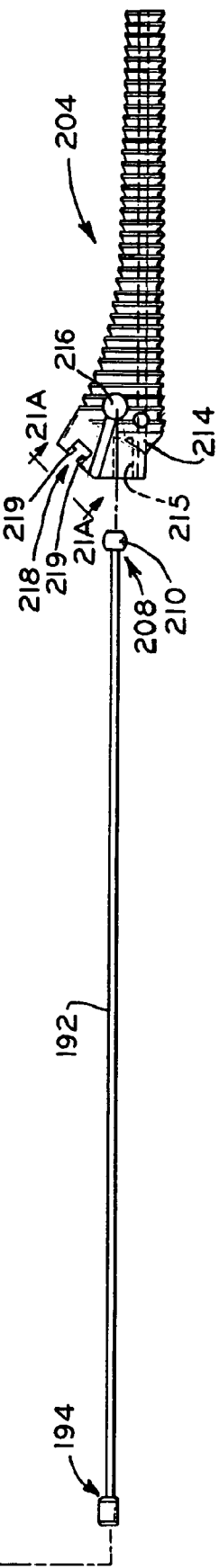

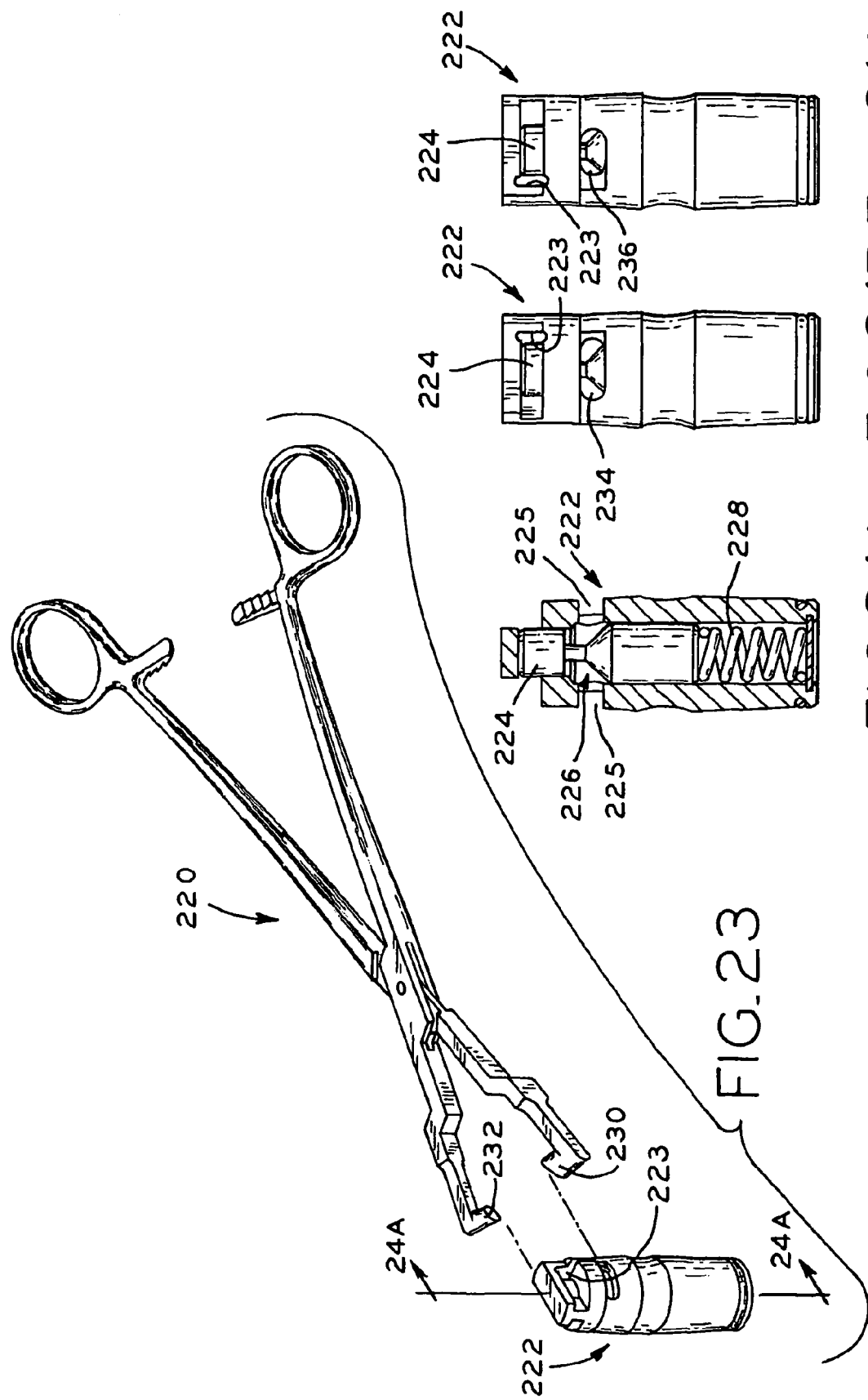

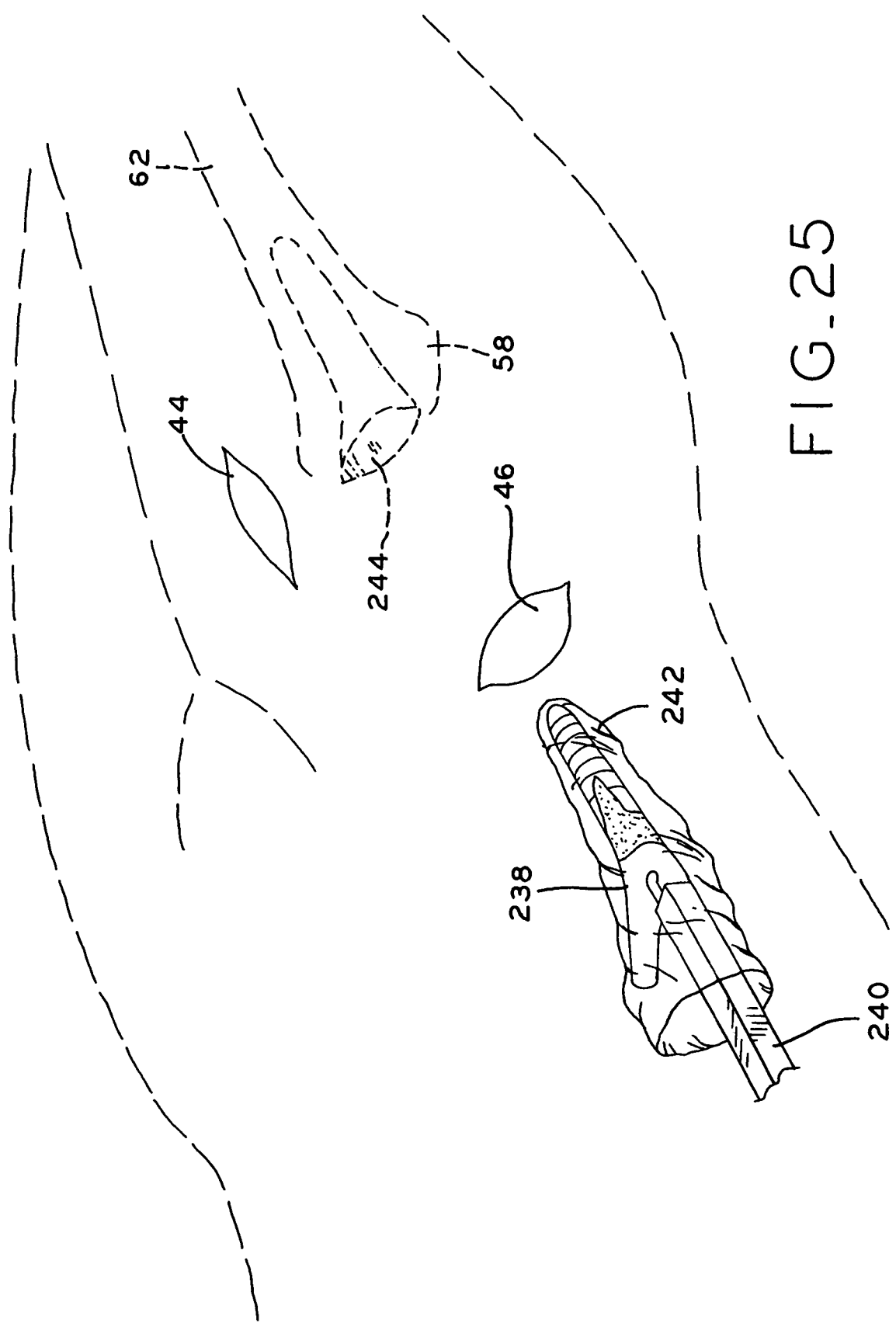

FIG_27

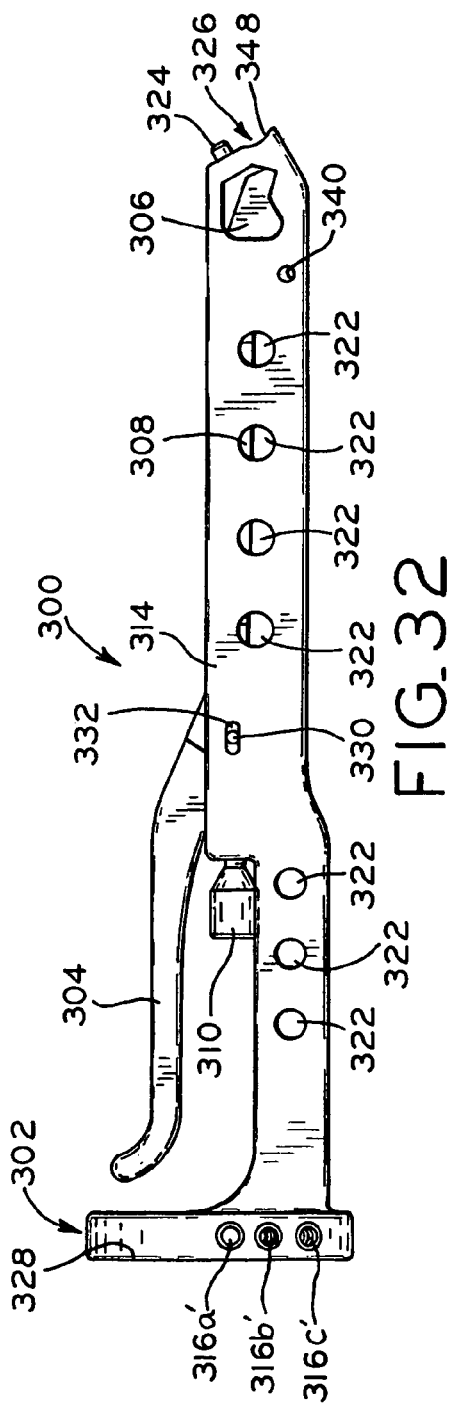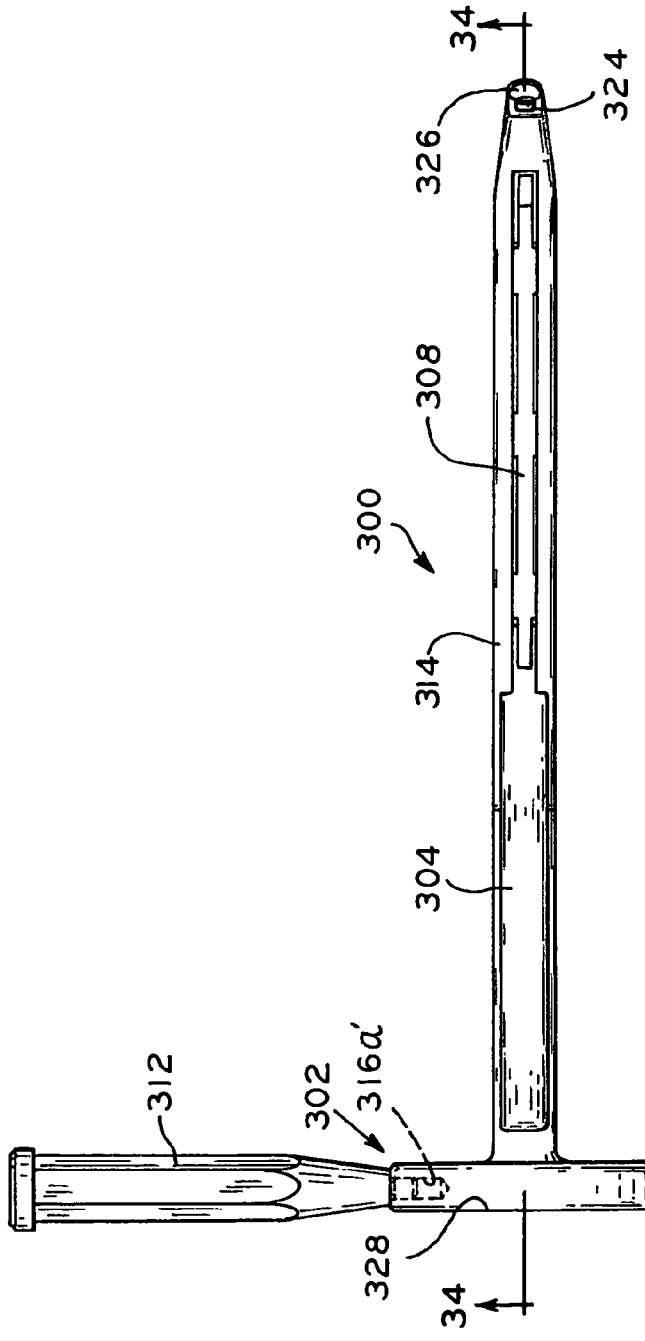

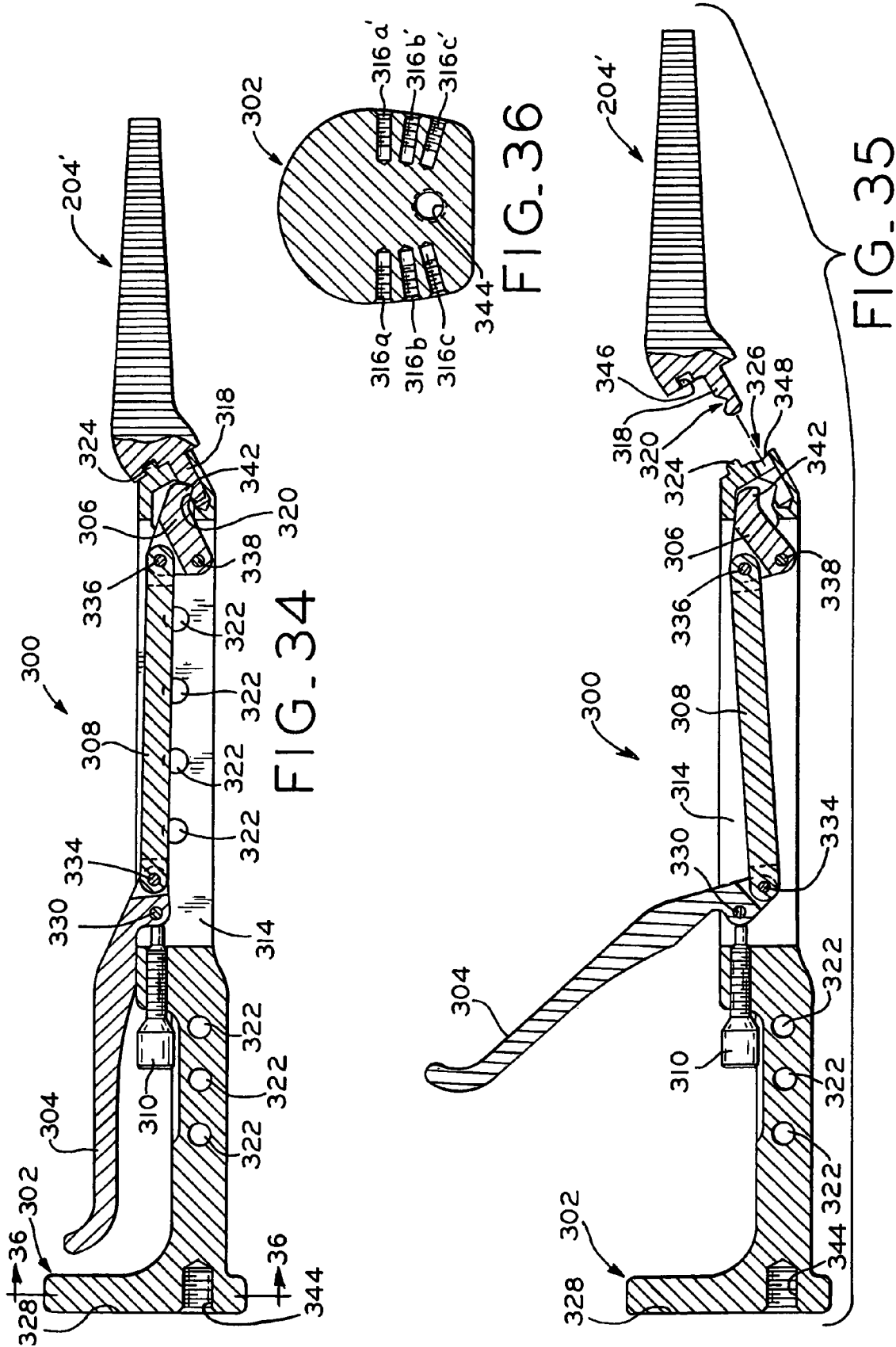

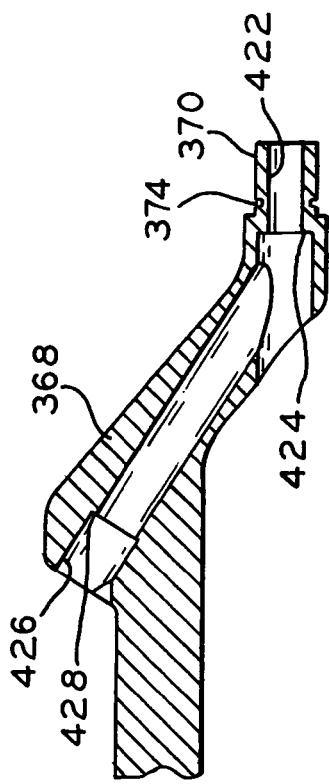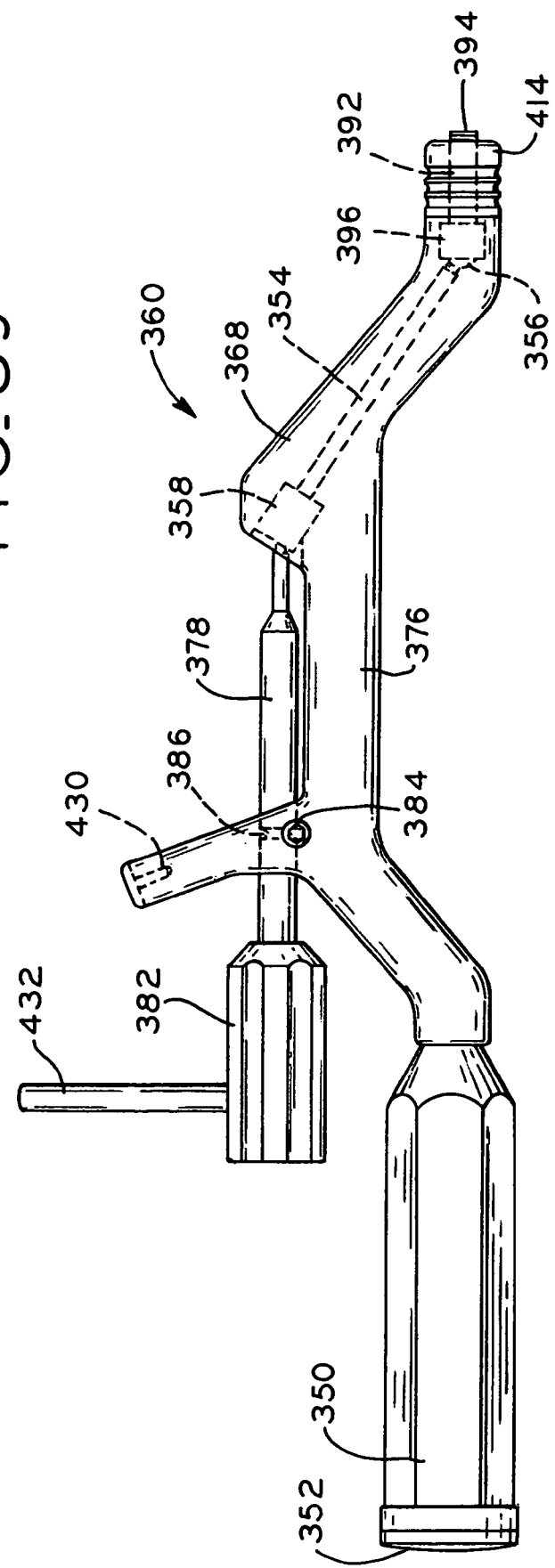

FIG_62

METHOD AND APPARATUS FOR PERFORMING A MINIMALLY INVASIVE TOTAL HIP ARTHROPLASTY

CROSS-REFERENCE TO RELATED APPLICATIONS

This application is a divisional of co-pending U.S. patent application Ser. No. 10/357,948, filed on Feb. 4, 2003 and published as U.S. Patent Publication No. U.S. 2003/0220698 A1 on Nov. 27, 2003, the disclosure of which is hereby explicitly incorporated by reference herein, which is a continuation-in-part of co-pending U.S. patent application Ser. No. 10/053,931, filed on Jan. 22, 2002 and published as U.S. Patent Publication No. U.S. 2002/0116067 A1 on Aug. 22, 2002, the disclosure of which is hereby explicitly incorporated by reference herein, which is a continuation-in-part of U.S. patent application Ser. No. 09/558,044, filed on Apr. 26, 2000 and issued as U.S. Pat. No. 6,676,706 on Jan. 13, 2004, the disclosure of which is hereby explicitly incorporated by reference herein.

BACKGROUND

1. Field of the Invention

The present invention relates to total hip arthroplasty, and, more particularly, to a method and apparatus for performing a minimally invasive total hip arthroplasty.

2. Description of the Related Art

Orthopaedic procedures for the replacement of all, or a portion of, a patient's joint have been developed over the last 30 years. Currently, the procedures used to prepare the bone and seat the implants are generally referred to as open procedures. For the purpose of this discussion, the term open procedure will refer to a procedure wherein an incision is made through the skin and underlying tissue to fully expose a large portion of the particular joint surface. In the case of a total hip arthroplasty, the typical incision required is approximately 25 centimeters (10 inches) long. After the initial incision in the skin, the internal wound may be enlarged in order to fully expose the areas to be prepared. While this approach provides surgeons with an excellent view of the bone surface, the underlying damage to the soft tissue, including the muscles, can lengthen a patient's rehabilitation time after surgery. While the implants may be well fixed at the time of surgery, it may be several weeks or perhaps months before the soft tissues violated during surgery can be fully healed.

SUMMARY

The present invention provides an improved method and apparatus for performing a minimally invasive total hip arthroplasty. A total hip arthroplasty can be performed in accordance with the teachings of the current invention utilizing two incisions with the size of each of the wounds developed on the surface being substantially constant throughout the depth of the wound. The first incision is an anterior incision approximately 3.75-5 centimeters (1.5-2 inches) in length made in line with the femoral neck and the central axis of the acetabulum. The second incision is a posterior incision approximately 2.5-3.75 centimeters (1-1.5 inches) positioned to be generally in axial alignment with the femoral shaft. In an alternative embodiment, the anterior incision begins at the intertrochanteric ridge and is extended inferiorly and medially generally on the line along which the femoral neck will be severed from the femur. In this embodiment, the anterior incision is made in line with the Langer's lines in the skin and therefore leads to less scarring. In the alternative embodiment, the posterior incision is aligned with the femoral shaft and is generally colinear with the anterior incision. In this way, the anterior incision and the posterior incision can be connected to allow for an open procedure in the event that a minimally invasive procedure is planned but an open procedure is determined to be necessary.

The femoral head is severed from the femoral shaft and removed through the anterior incision. The acetabular cup is placed in the acetabulum through the anterior incision, while the posterior incision is used to prepare the femoral shaft to receive a femoral stem. A femoral stem is inserted through the posterior incision and positioned in the femoral shaft. Procedures performed through the posterior incision may be observed through the anterior incision and vice versa.

For the purpose of the following discussion, a total hip arthroplasty is defined as a replacement of the femoral head with or without the use of a separate acetabular component. The specific designs which can be utilized in accordance with the present invention include a total hip replacement and a bipolar or monopolar endo prosthesis. The technique is suitable for cemented or cementless anchorage of the components.

The apparatus and method of the current invention advantageously allow a total hip arthroplasty to be performed in a minimally invasive way, which hastens patient recovery.

BRIEF DESCRIPTION OF THE DRAWINGS

The above-mentioned and other features and advantages of this invention, and the manner of attaining them, will become more apparent and the invention itself will be better understood by reference to the following description of an embodiment of the invention taken in conjunction with the accompanying drawings, wherein:

FIG. 1A is a side elevational view of a patient illustrating a pair of incisions made according to the current invention as well as the incision utilized in prior art procedures;

FIG. 1B is a side elevational view of a patient illustrating an alternative pair of incisions made according to the current invention as well as a line joining the incision pair along which a third incision can be made to join the incision pair and convert the procedure from a minimally invasive procedure to an open procedure;

FIG. 2B is an anterior elevational view of a hip joint illustrating the line along which the femoral neck will be severed from the femur and further illustrating the location of anterior incision 44' depicted in FIG. 1B;

FIG. 4 is an anterior elevational view of the femoral neck with an osteotomy guide of one form of the current invention operably positioned to designate a cut line thereon;

FIG. 6A is an anterior elevational view illustrating the femoral head and neck severed along the cut line indicated by the osteotomy guide;

FIG. 6B is an anterior elevational view illustrating the femoral head and neck severed along the cut line illustrated in FIG. 2B and further illustrating the line along which the femoral head is severed from the femoral neck in accordance with one embodiment of the present invention;

FIG. 7 is an anterior elevational view illustrating the removal of a portion of the femoral head and neck;

FIG. 10 is an anterior elevational view of a portion of the cup inserter illustrated in FIG. 9 and a patient lying in the supine position;

FIG. 14A is a side elevational view of an alternative embodiment of the tubular retractor;

FIG. 17A is a perspective view of an end cutter;

FIG. 17B is a perspective view of a femoral reamer;

FIG. 18 is a side elevational, partial sectional view of an end cutter inserted into a tubular retractor of the present invention;

FIG. 19A is a perspective view illustrating an inserted rasp, with the rasp handle removed, and with the cable used to affix the rasp to the rasp handle protruding from the posterior incision;

FIG. 21 is an exploded view of the rasp handle and a rasp to be connected thereto;

FIG. 21A is a partial elevational view along line 21A-21A of FIG. 21;

FIG. 23 is a perspective view of the provisional neck and mating forceps of the present invention;

FIG. 24A is a partial sectional, radial elevational view of the provisional neck;

FIGS. 24B and 24C are radial elevational views thereof;

FIG. 25 is a perspective view illustrating the insertion of a femoral stem with a protective bag through the posterior incision;

FIG. 32 is a side elevational view thereof;

FIG. 33 is a top elevational view thereof;

FIG. 34 is a sectional view illustrating a rasp secured to the rasp handle;

FIG. 35 is a sectional view illustrating release of the locking mechanism used to secure a rasp to the rasp handle;

FIG. 36 is a sectional view of the impaction surface of the rasp handle illustrated in FIGS. 31-35;

FIG. 38 is a side plan view thereof;

FIG. 39 is a partial sectional view of the distal portion of the frame of the cup inserter illustrated in FIGS. 37 and 38;

Corresponding reference characters indicate corresponding parts throughout the several views. The exemplification set out herein illustrates one preferred embodiment of the invention, in one form, and such exemplification is not to be construed as limiting the scope of the invention in any manner.

Figure 2A:
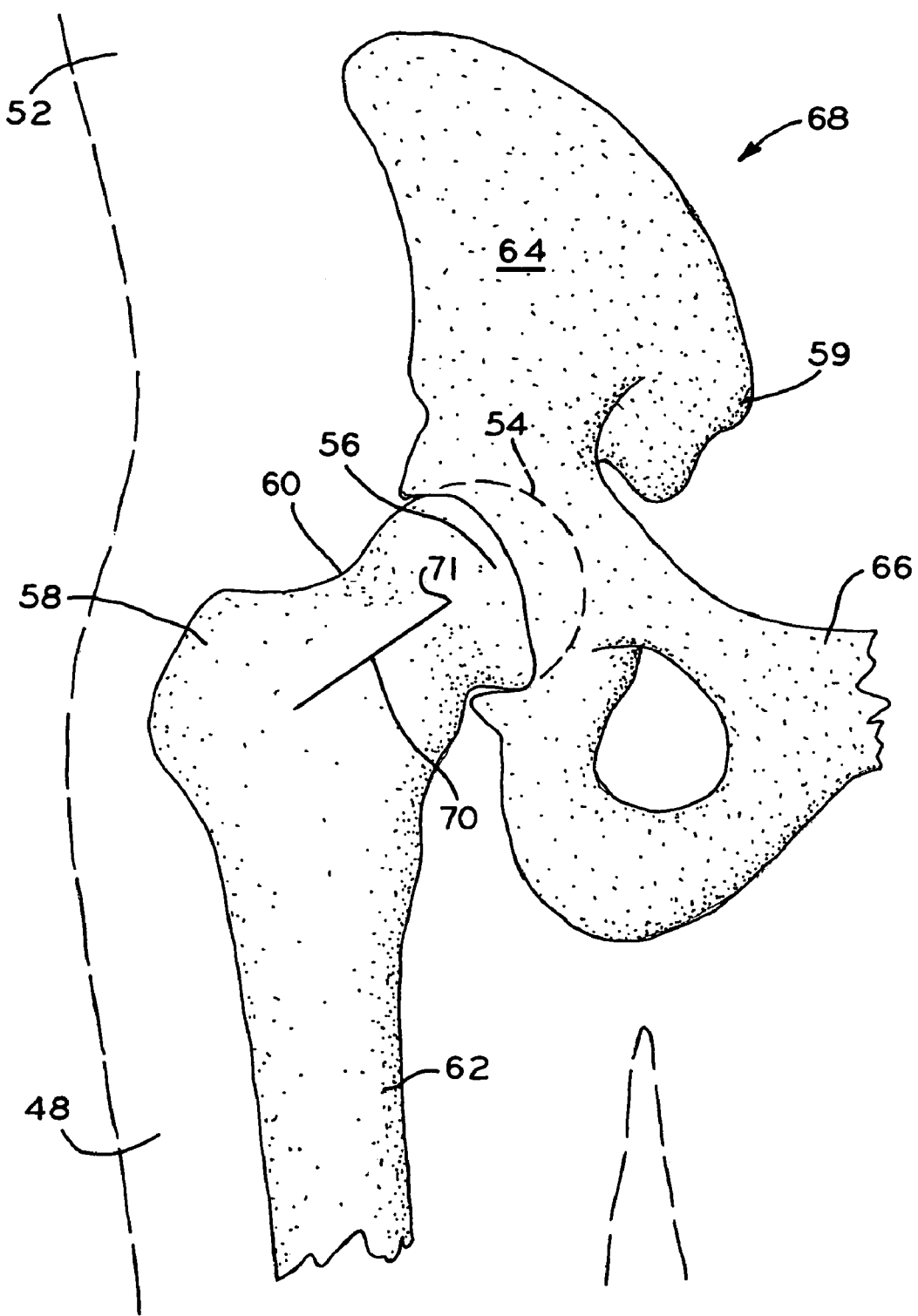
FIG. 2A is an anterior elevational view of a hip joint illustrating the femoral neck axis.

Throughout this document "proximal" and "distal" are sometimes used to refer to opposite ends of instruments described herein. When referring to the opposite ends of instruments, "proximal" and "distal" are used with reference to a user of the instrument. For example, the end of the instrument nearest the user during use thereof is described as the proximal end, while the end of the instrument farthest from the user during use is described as the distal end of the instrument.

DETAILED DESCRIPTION

A total hip arthroplasty can be performed, according to the teachings of the current invention through two incisions, each no more than 5 centimeters (2 inches) in length. An anterior incision is made either along the axis of the femoral neck or aligned with the line along which the femur will be osteotomized to remove the femoral neck, while a posterior incision is made generally in axial alignment with the femoral shaft. Referring to FIG. 1A, a partial illustration of patient 40 including torso 52, buttock 50, and leg 48 illustrates prior art incision 42 as well as exemplary anterior incision 44 and exemplary posterior incision 46 of the current invention. Prior art incision 42 is approximately 25 centimeters (10 inches) long, while anterior incision 44 and posterior incision 46 are each no more than 5 centimeters (2 inches) in length. Referring to FIG. 1B, a partial illustration of patient 40' including torso 52', buttock 50', and leg 48' is used to illustrate exemplary anterior incision 44' and exemplary posterior incision 46' of the current invention. Anterior incision 44' and posterior incision 46' are each no more than 5 centimeters (2 inches) in length. As illustrated in FIG. 1B, anterior incision 44' and posterior incision 46' are generally colinear and can be joined along line 47 to allow for a minimally invasive hip procedure to be altered to an open procedure.

According to the method of total hip arthroplasty of the current invention, patient 40 is initially placed in a supine position on an operating table. A standard operating table or a radiolucent table can be used. In one exemplary embodiment, operating table 400 illustrated in FIGS. 56-61 is utilized. Operating table 400 includes a table top which is completely radiolucent, i.e., no portion of the table top of operating table 400 is radiopaque. Operating table 400 will be described in further detail hereinbelow. A radiolucent table is preferred if the surgical team intends to use intraoperative image intensification. In one exemplary embodiment, fluoroscopic images are taken repeatedly taken throughout the procedure to confirm proper positioning of instruments, and implants. In alternative embodiments, endoscopic images can be taken. A Storz viewsite endoscopic system provides a sterile viewing screen for endoscopic images. The sterile viewing screen of a Storz viewsite endoscopic system can be positioned within the surgical field immediately adjacent to anterior incision 44 or 44'. Other known endoscopic systems may further be utilized during the total hip arthroplasty of the present invention.

Referring now to FIG. 2A, with ipsilateral leg 48 in a neutral position, two prominent bony landmarks are palpated, anterior superior iliac spine (ASIS) 59 and greater trochanter 58 of femur 62. Ilium 64 and pubis 66 of hip 68 are shown to better illustrate the relevant area of the body. In one exemplary embodiment, the approximate anterior incision starting point 71 is identified two fingerbreadths inferior and two fingerbreadths anterior to the tubercle of the greater trochanter 58. The approximate finish point for the anterior incision is identified three fingerbreadths inferior and two fingerbreadths lateral to the anterior superior iliac spine (ASIS) 59. In another exemplary embodiment, the approximate anterior incision starting point 71 is identified 3-4 centimeters inferior and 2 centimeters lateral to ASIS 59. Having identified starting point 71 3-4 centimeters inferior and 2 centimeters lateral to ASIS 59, the path of anterior incision 44 is extended obliquely from starting point 71 toward the prominence of greater trochanter 58 along the axis of femoral neck 60. With the use of a spinal needle, the appropriate starting point 71 and the path of the anterior incision can be identified by impaling the skin down to bone to confirm the central axis 70 of femoral neck 60. In one exemplary embodiment, a metal, or other radiopaque marker can be positioned over the identified path of anterior incision 44 and a fluoroscopic image taken to confirm the appropriate position of anterior incision 44. If anterior incision 44' (FIG. 1B) is utilized, then starting point 71' (FIG. 2B) can be identified by palpating intertrochanteric ridge 59 and extending the incision obliquely as illustrated in FIG. 2B. The position of intertrochanteric ridge 59 can be confirmed by impaling the skin down to the bone with, e.g., a spinal needle. The location of anterior incision 44' can further be confirmed by placing a metallic or otherwise radiopaque instrument over line 61 illustrated in FIG. 2B and taking a fluoroscopic image. After confirmation of the path of anterior incision 44 or 44', a surgical marker can be utilized to mark the location of same on the patient's skin.

Figure 2C:
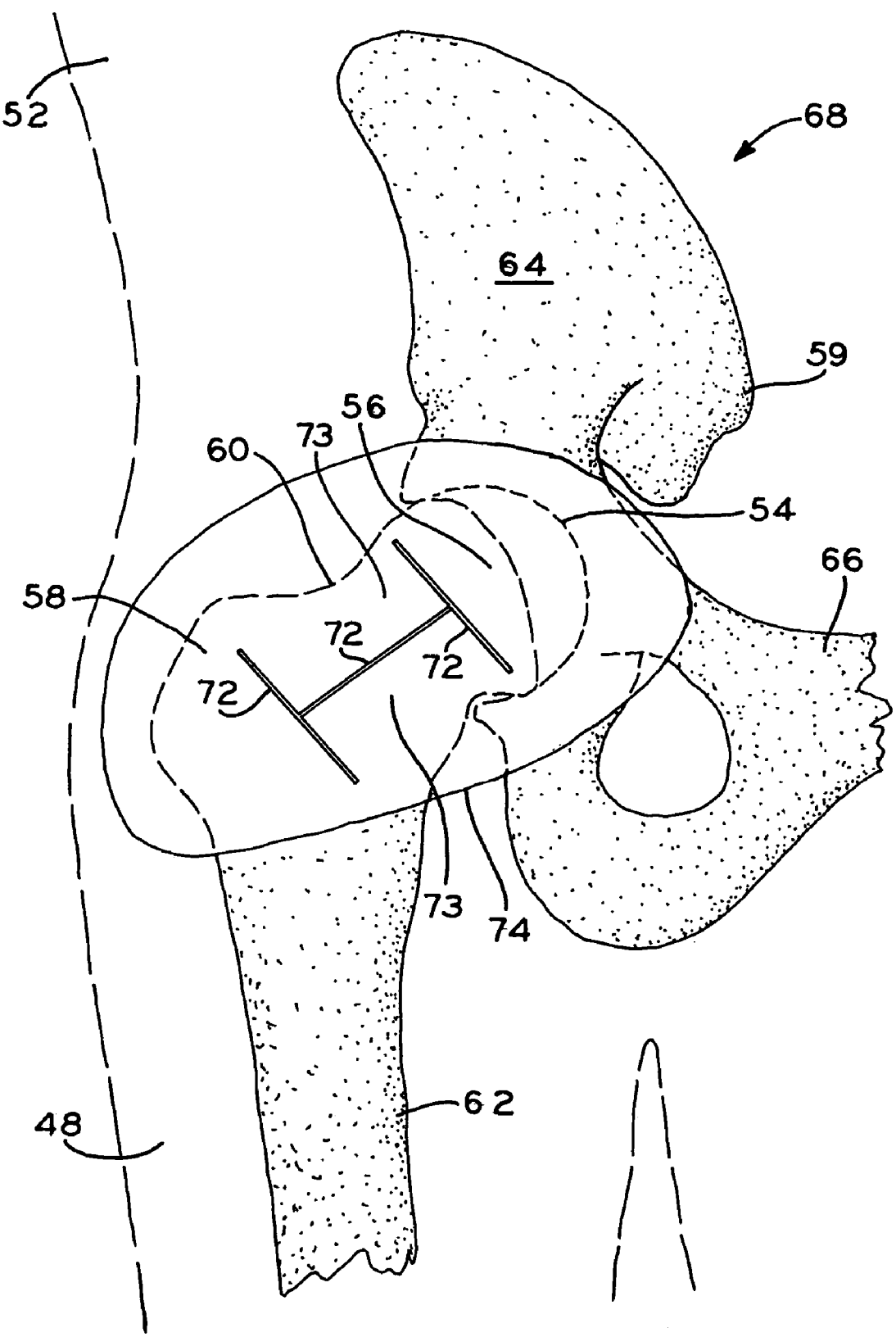
FIG. 2C is an anterior elevational view illustrating the capsule of the hip joint.

If anterior incision 44 is utilized, an oblique incision of approximately 3.75-5 centimeters (1.5-2 inches) is made from the starting site 71 toward the prominence of the greater trochanter along the axis 70 of the femoral neck 60 and the central axis of acetabulum 54 to form anterior incision 44 as illustrated, e.g., in FIG. 1A. If anterior incision 44' is utilized, an oblique incision of approximately 3.75-5.0 centimeters (1.5-2.0 inches) is made from starting site 71' and extended obliquely along line 61 illustrated in FIG. 2B. The anterior incision (44 or 44') is extended along the same plane through subcutaneous tissues, exposing the underlying fascia lata. The internervous plane between the tensor fascia lata muscle and the sartorius is identified by palpation and developed by curved scissors and blunt dissection. The sartorius can be made more prominent by externally rotating the leg to apply tension on the muscle. Deep to the tensor fascia lata and the sartorius is an internervous interval between the rectus femoris and the gluteus medius. This plane is developed by blunt dissection. A lateral retraction of the tensor fascia lata permits a visualization of the capsule 74 of the hip joint as illustrated in FIG. 2C. In this way, the hip capsule is exposed without requiring the incision of muscle. In some cases the indirect head of the rectus femorus will be taken down to expose the hip capsule, but it is generally very easy to elevate the rectus femorus from the capsule without damaging it and expose the hip capsule with no violation of muscle. After dissecting below the tensor fascia lata, the precapsular fat and lateral circumflex vessel that travels across the front of the capsule are exposed. The circumflex vessels may present as one or 2 larger arteries and veins, or multiple smaller vessels. If the circumflex vessels are relatively large, they can be ligated to prevent bleeding during reaming of the acetabulum. If they are smaller, they can be cauterized.

Figure 3:
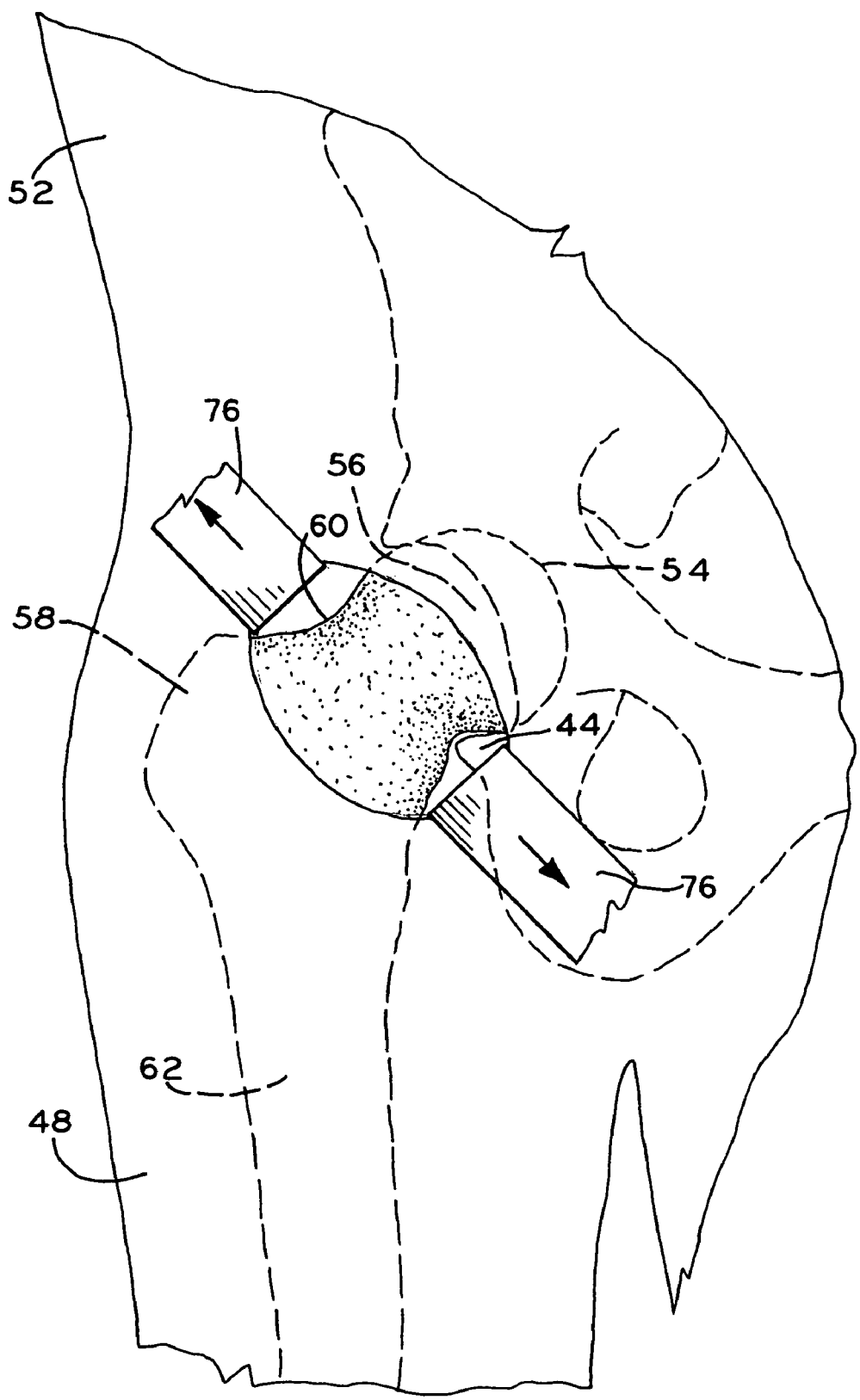
FIG. 3 is an anterior elevational view of the femoral neck exposed by incising the hip capsule.

Leg 48 is externally rotated to create tension on capsule 74. Capsule 74 is incised along the axis 70 (FIG. 2A) of femoral neck 60 from the equator of femoral head 56 to the intertrochanteric ridge of femur 62. In one exemplary embodiment, the capsular incision takes the form of an "H-shaped" window formed by incisions 72 (FIG. 2C). The H-shaped window is formed by adding supplementary perpendicular limbs around the equator of femoral head 56 and the base of femoral neck 60 to the initial incision along the axis 70 of femoral neck 60. As a form of retraction, heavy sutures can be used to provisionally attach the capsular flaps 73 to the subcutaneous tissues. In alternative embodiments, the capsular incision is formed as a T-shape, or as a linear incision. In certain embodiments, a triangular portion of the capsule can be removed. As illustrated in FIG. 3, retractors 76 are placed inside capsular flaps 73 and underneath the superior and inferior borders of femoral neck 60 to expose the entire length of femoral neck 60 from the inferior aspect of femoral head 56 to the intertrochanteric ridge. Retractors 76 can be, e.g., Cobra retractors. In one exemplary embodiment, each retractor houses a light source and can also serve to anchor an endoscope. Retractors 76 thereby provide continuous visualization and illumination of the wound. In one exemplary embodiment, JAKOSCOPE retractors having integral fiberoptic light sources are utilized in accordance with present invention.

Referring now to FIG. 4, a femoral cutting tool 86, e.g., a reciprocating saw, oscillating saw or a power burr is used to excise femoral neck 60. A custom osteotomy guide 78 can be placed through anterior incision 44 (FIG. 1A) or 44' (FIG. 1B) to guide the femoral neck cut. Alignment portion 82 of osteotomy guide 78 is aligned with the longitudinal axis of femur 62, while cut guide 84 is positioned on femoral neck 60. Handle 80 of osteotomy guide 78 facilitates positioning and repositioning of osteotomy guide 78 through anterior incision 44 or 44'. After placement of osteotomy guide 78, cut line 85 is scored as is known in the art. Osteotomy guide 78 is thereafter removed through anterior incision 44 or 44' and femoral cutting tool 86 is inserted through anterior incision 44 or 44' and utilized to cut along cut line 85 and displace portion 88 (FIGS. 6A and 6B) from femur 62. If anterior incision 44' is utilized, it will be aligned with the osteotomy utilized to displace portion 88 from femur 62. In this way, anterior incision 44' may allow for less soft tissue irritation when osteotomizing cut portion 88 from femur 62 because the oscillating saw will move in line with anterior incision 44'.

Retractors 76 are repositioned around the anterior and posterior rims of the acetabulum. A custom curved cutting tool. (i.e., the "ligamentum teres cutter") is passed behind femoral head 56 to sharply incise the ligamentum teres, thus mobilizing cut portion 88 as illustrated in FIG. 6A. Cut portion 88 includes femoral head 56 as well as a portion of femoral neck 60 (FIG. 4). Cut portion 88 is thereafter removed through anterior incision 44 with a custom femoral head bone grasper 94 (FIG. 7). If there is difficulty removing cut portion 88 in one piece, it may be in situ morselized using cutting tool 87 (FIG. 6A), e.g., a power burr. Morsels 92 may then be removed through anterior incision 44 as illustrated in FIG. 7. Morselizing of cut portion 88 can be accomplished making cuts which substantially mirror the cuts in hip capsule 74. In one exemplary embodiment, a corkscrew and hip skid removes the entire femoral neck, as in hip fracture. In an alternative embodiment, femoral head 56 is severed along cut line 63 (FIG. 6B) prior to incising the ligamentum teres. In this embodiment, the osteotomized femoral neck is removed before incising the ligamentum teres. As described above, femoral head 56 may be in situ to morselized to facilitate removal thereof as necessary. A threaded Steinman pin or a Shanz screw can be utilized to remove the osteotomized femoral neck and head. Irrigation and suction devices can be used to cool the bone and facilitate the removal of bony debris in hip capsule 74. In one exemplary embodiment, a fiberoptic endoscope is placed into the hip joint to confirm the complete removal of bony debris.

Figure 8B:
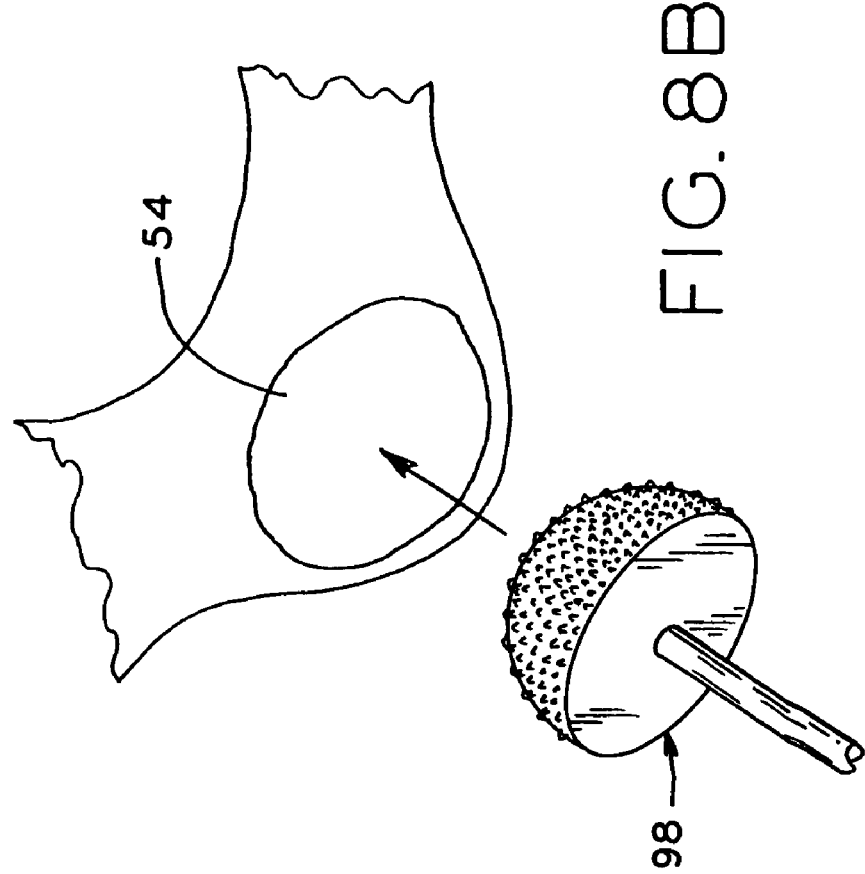
FIGS. 8A and 8B illustrate preparation of the acetabulum to receive the acetabular cup.
Figure 8A:
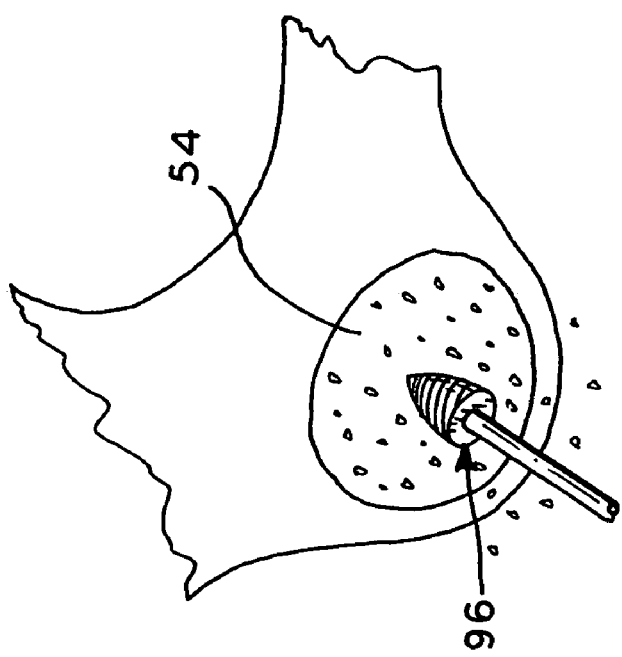

As illustrated in FIG. 8A, the fibro-fatty tissue within the cotyloid fossa of acetabulum 54 is removed with the use of, e.g., high-speed acorn-tipped cutting tool 96, Rongeur forceps, and a curette. Thereafter, the acetabular labrum can be trimmed with a scalpel. As illustrated in FIG. 8B, acetabulum 54 is then progressively reamed with standard acetabular reamer 98. In an alternative embodiment, a customized minimally invasive reamer such as the one disclosed in co-pending U.S. patent application Ser. No. 10/153,053, filed May 21, 2002, the disclosure of which is hereby explicitly incorporated by reference herein, can be utilized to progressively ream acetabulum 54. Acetabular reamers within a predetermined size range are utilized until the optimal size of the acetabulum is reached. Sizing of the acetabulum is facilitated by the use of pre-operative templates and radiographs as is known in the art. A fluoroscope, or endoscope can be used to aid in visualization during the reaming process. In certain instances, multiple fluoroscopic or endoscopic images are taken during the reaming process to confirm that when reaming is complete the reamer is bottomed out and is concentric with the acetabulum. Typically the acetabulum is under reamed by approximately 2 mm with respect to the diameter of the anticipated acetabular cup so as to create an interference fit. High speed acorn-shaped cutting tool 96, and acetabular reamer 98 enter the body through anterior incision 44 or 44'.

Figure 9A:
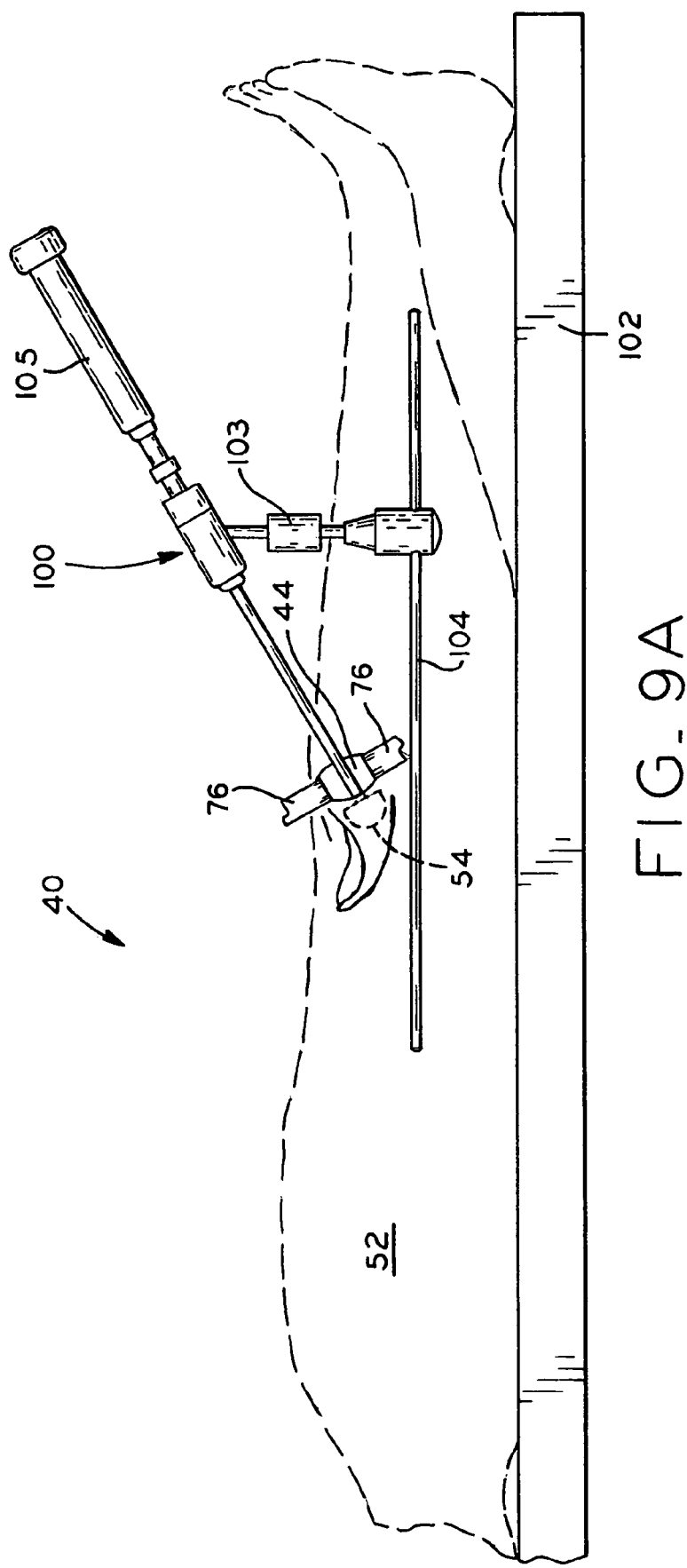
FIG. 9 is a side elevational view of an acetabular cup inserter relative to a patient lying in the supine position.

After a trial fitting, a press-fit acetabular cup of the appropriate size can be firmly seated with cup inserter 100 as illustrated in FIG. 9 and impacted into the acetabular recess as is known in the art. In alternative embodiments, acetabular cup inserters 360, 360' (FIGS. 9B, 37-55) may be utilized to seat an appropriate acetabular cup. Cup inserters 360 and 360' are further described hereinbelow. If a balloon is positioned under the hip and inflated during the total hip arthroplasty of the present invention, it can be deflated when determining proper alignment for seating of the acetabular implant. Acceptable press fit acetabular cups include the ZIMMER HGP II or TRILOGY cups. Proper positioning of the acetabular cup can be achieved with a custom anteflexion and pelvic alignment guide as illustrated in FIG. 9A. Patient 40 is placed in supine position on operating table 102. Aligning rod 104 is aligned with the mid lateral axis of torso 52 while main shaft 105 is maintained approximately 30° from operating table 102 for proper seating of the acetabular cup. To augment fixation of the cup, a flexible drill can be used to guide the placement of one or more acetabular screws. In some cases, acetabular screws will not be necessary. The insertion of the acetabular liner is, in certain embodiments, deferred until the proximal femur has been prepared for the insertion of a trial stem. As illustrated by the anterior elevational view of FIG. 10, patient 40 remains in the supine position on operating table 102 (FIG. 9) while cup inserter 100 is utilized to seat the acetabular cup. Similarly, patient 40 remains in the supine position on operating table 102 if either of cup inserters 360, 360' are utilized to seat the acetabular cup.

For preparation of the femur, the patient is repositioned with a pad, e.g., an inflatable pad placed under the ipsilateral hip. In one exemplary embodiment, an inflatable pad is placed under the hip and inflated at the beginning of the procedure. With an inflatable pad in place under the hip and inflated, the femur will drop below the acetabulum when the femoral neck is osteotomized giving better access to both the acetabulum and the femur. The operative hip is slightly flexed or extended, adducted approximately 30° to 45°, and maximally externally rotated or rotated to approximately 30° to 45°. In one exemplary embodiment, an operating table having movable leg panels is utilized. In this embodiment, the non-operative leg can be dropped below the operative leg prior to position the operative hip for preparation of the femur (e.g., extending, adducting, and rotating the operative hip). When the non-operative knee is lowered, i.e., the non-operative hip is hyperextended, the operative hip is effectively raised, which facilitates preparation of the femur as described below. Retractors 76 are repositioned around the medial and lateral aspects of femur 62. Alternatively, a self-retaining retractor with a light source attachment and an endoscope holder can be positioned in anterior incision 44 to provide constant visualization and illumination of femur 62.

Figure 11:
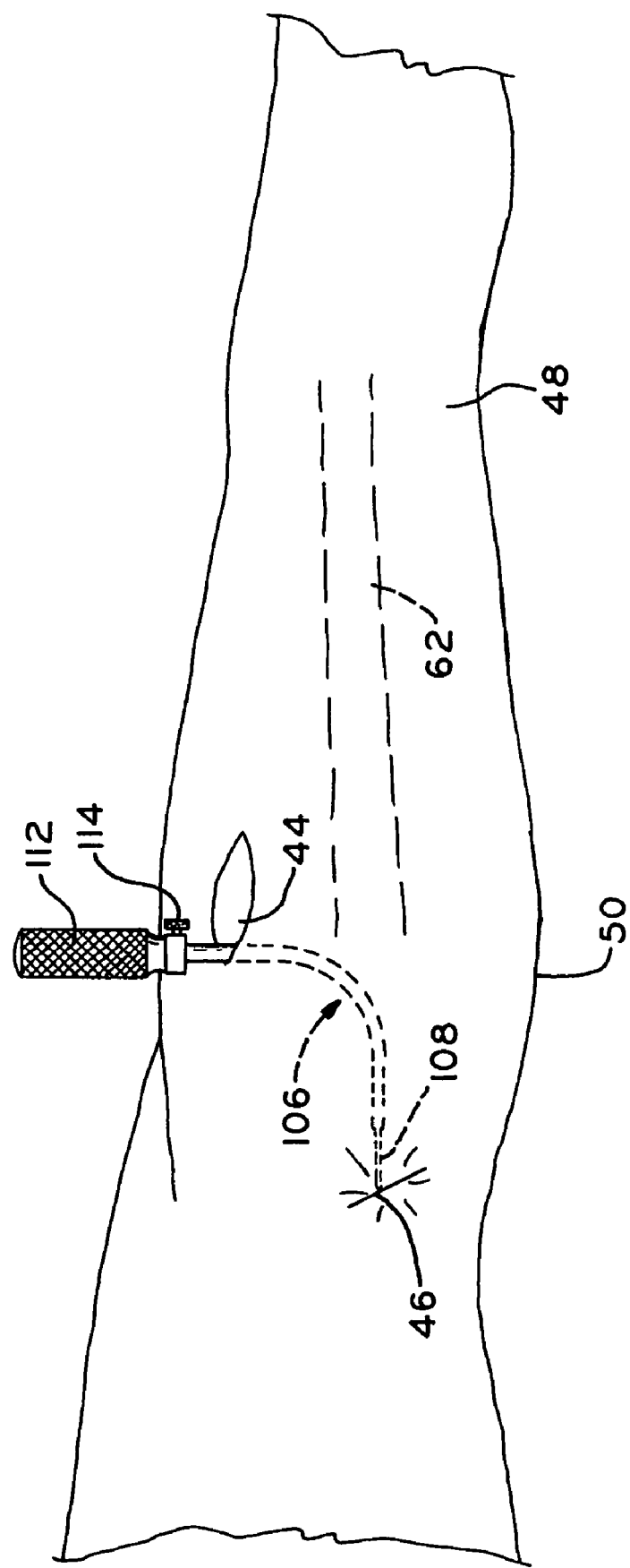
FIG. 11 is a side elevational view illustrating the use of a curved awl to locate a posterior incision.

In one embodiment, the soft tissues along the anterior surface of femur 62 just inferior to the intertrochanteric ridge are subperiosteally reflected with a scalpel or curved osteotome to expose the bone for a width of approximately 1 cm. This sharp subperiosteal elevation continues superolaterally onto the anterior margin of the greater trochanter. Then with curved Mayo scissors a pathway is developed by blunt dissection that is directed superficially to the anterior fibers of the gluteus minimus towards buttock 50 (FIG. 11). In an alternative embodiment, the osteotomized femoral neck is visualized through the anterior incision and any remaining superolateral femoral neck is removed. Curved Mayo scissors are then directed posterior to the posterior neck of the femur just superior to the insertion of the piriformis tendon. If the piriformis tendon traverses this site, it is divided with the scissors. the scissors are advanced through the posterior capsule and toward the gluteus maximus. To assist in the direction of the scissors, a line can be drawn along the front axis of the femur and along the side axis. Where the two lines intersect on the superolateral aspect of the hip is the appropriate site for the posterior as is further described herein below.

Figure 13:
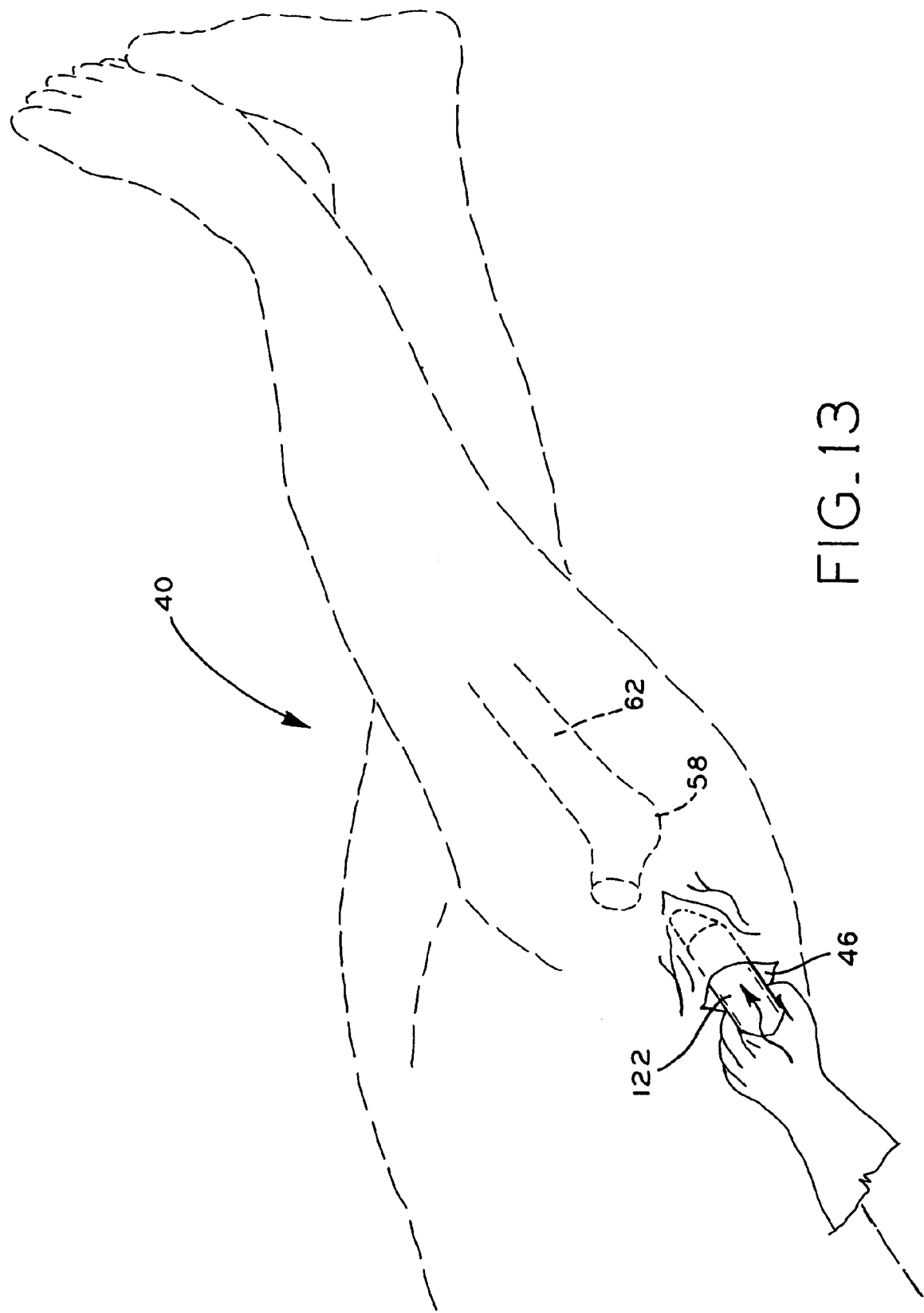
FIG. 13 is a perspective view illustrating the insertion of a posterior retractor in the posterior incision.
Figure 14:
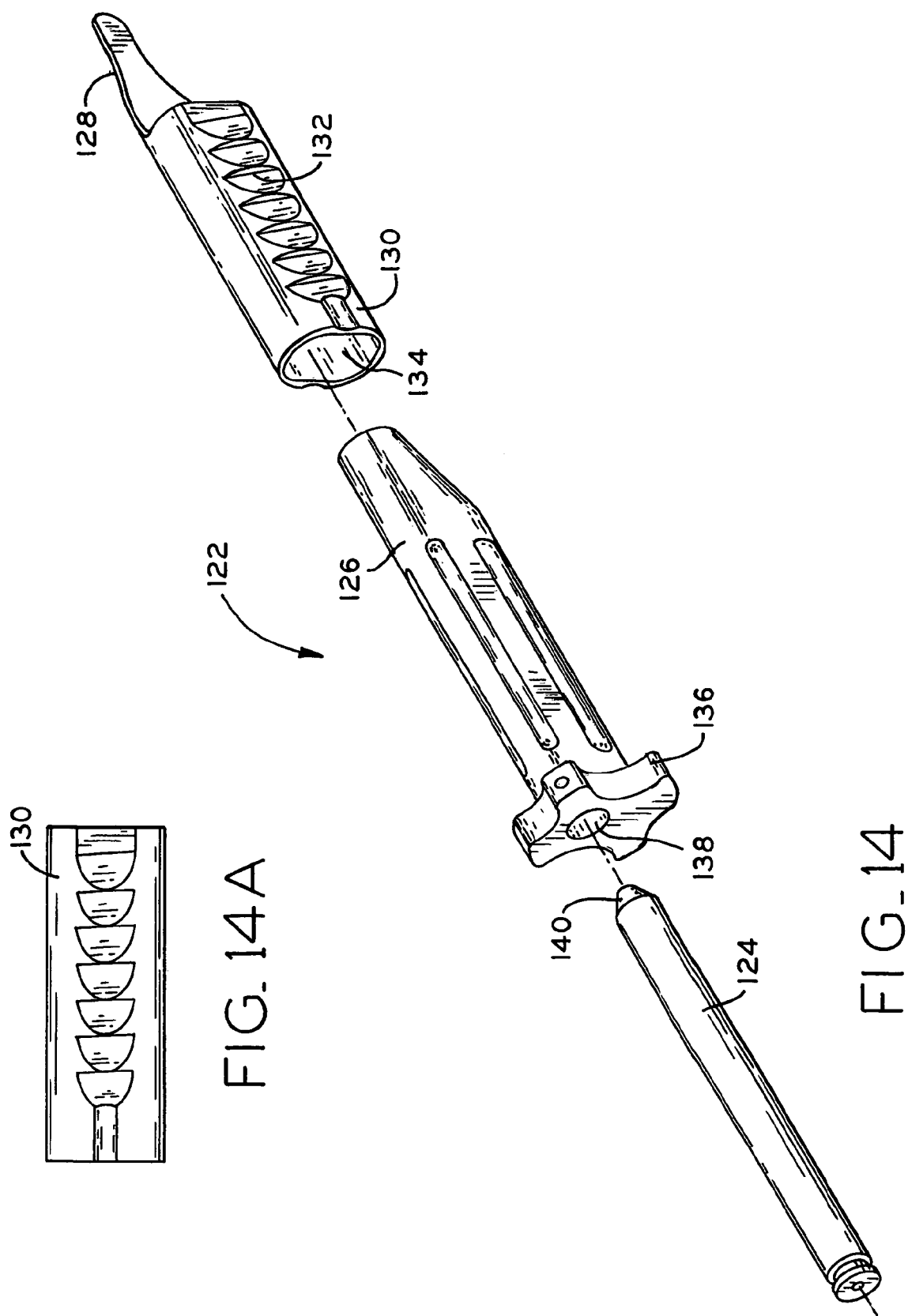
FIG. 14 is a perspective, exploded view of one embodiment of a tubular retractor in accordance with the present invention.

As illustrated in FIG. 11, awl 106 is inserted through anterior incision 44, directed through the cleft between the gluteus medius and maximus in line with the shaft of the femur and piriformis fossae region, and advanced into the soft tissues of buttock 50 until its pointed distal end 108 can be palpated on the surface of the skin. Distal end 108 of awl 106 is generally aligned with the longitudinal axis of femur 62. At the point where distal end 108 is palpated, posterior incision 46 or 46' of approximately 2-3 cm (0.8-1.2 inches) is made and extended through the subcutaneous tissues and fascia lata to expose the underlying gluteus maximus. In one exemplary embodiment, a surgical marking pen can be used to draw a line on the skin down the front of the femur and a line on the skin along the side of the femur. The intersection of these two lines will generally mark the position of the posterior incision. A tract to femur 62 is developed along the path created by awl 106. Generally, the gluteus maximus is split bluntly in line with its fibers with curved Mayo scissors. Finger dissection may be utilized to reach the posterior piriformis fossa region. In certain cases the piriformis obstructs the view of the femur. In these cases, the piriformis can be divided. In many instances, the piriformis is inferior to the femur and does not require division. Into this pathway, via posterior incision 46 or 46', custom elliptical posterior retractor 122, complete with its inner sleeves, can be threaded (FIG. 13) down to the osteotomized femoral neck. In one exemplary embodiment, elliptical posterior retractor 122 includes posterior lip 128 (FIG. 14). In this embodiment, retractor 122 is threaded down to the osteotomized femoral neck until posterior lip 128 lies beneath the posterior intertrochanteric ridge. FIG. 14A illustrates an embodiment of rasp tunnel 130 without posterior lip 128. In an alternative embodiment, each component of posterior retractor 122 (i.e., guide tube 124, reamer tunnel 126, and rasp tunnel 130) is individually inserted and removed as necessary. In an embodiment in which guide tube 124, reamer tunnel 126, and rasp tunnel 130 are individually inserted and removed into posterior incision 46 or 46', each individual tunnel may be provided with a posterior lip similar to posterior lip 128 illustrated in FIG. 14. In yet another exemplary embodiment, no posterior retractor is utilized. Rasping and reaming of the femur will now be described. The posterior capsule will be entered to facilitate rasping and reaming of the femur. Any step performed through a tubular retractor positioned in the posterior may be performed through the posterior incision without a retractor positioned therein.

Initially, under image guidance, a straight pointed awl is inserted into the posterior incision while observing its progress through the anterior incision. The awl is inserted into the osteotomized femoral neck and advanced manually down the femoral canal. Upon its removal, a ball tipped guide wire is inserted through the posterior incision into the osteotomized femoral neck down the femoral canal.

Figure 15:
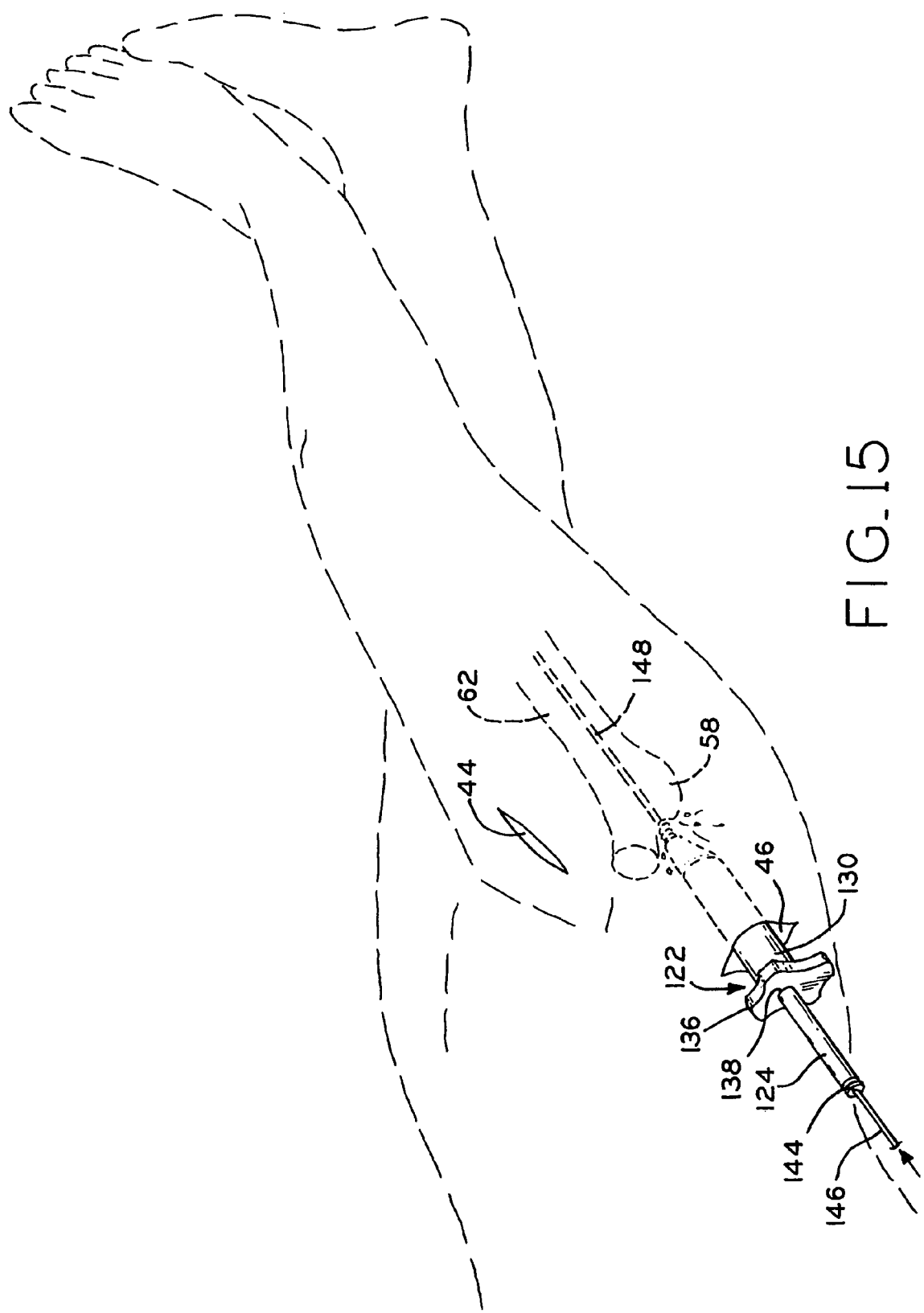
FIG. 15 is a perspective view illustrating the insertion of a guide wire into the tubular retractor.

Referring now to FIG. 15 in one exemplary embodiment, ball tipped guide wire 146 is inserted through guide tube 124 of posterior retractor 122 and advanced into femoral canal 148. While FIG. 15 illustrates guide tube 124 nested in reamer tunnel 126 and rasp tunnel 130, guide tube 124 may be directly inserted through posterior incision 46 or 46', or not used. In one exemplary embodiment, ball-tipped guide wire 146 is directly inserted through posterior incision 46 or 46' and advanced into femoral canal 148. If the cancellous bone of femur 62 is too dense to permit insertion of ball tipped guide wire 146, then a conical cannulated reamer or end mill is used to prepare the femoral metaphysis. If a nested posterior retractor configuration is utilized, guide tube 124 must be removed so that the reamer can be inserted through reamer tunnel 126 of posterior retractor 122. Similarly, if a nested configuration is not utilized, reamer tunnel 126 can be inserted into posterior incision 46 if the surgeon chooses to use it. In any event, ball tipped guide wire 146 is inserted about halfway down femoral canal 148. The following detailed description of the invention makes reference to a nested posterior retractor configuration. It will be understood by those skilled in the art that if the nested configuration is not utilized, each individual component of posterior retractor 122 can be inserted and removed through posterior incision 46 as necessary. Moreover, if no tubular posterior retractors are utilized, then the following steps can be performed by placing instruments directly through posterior incision 46 or 46'.

Figure 16:
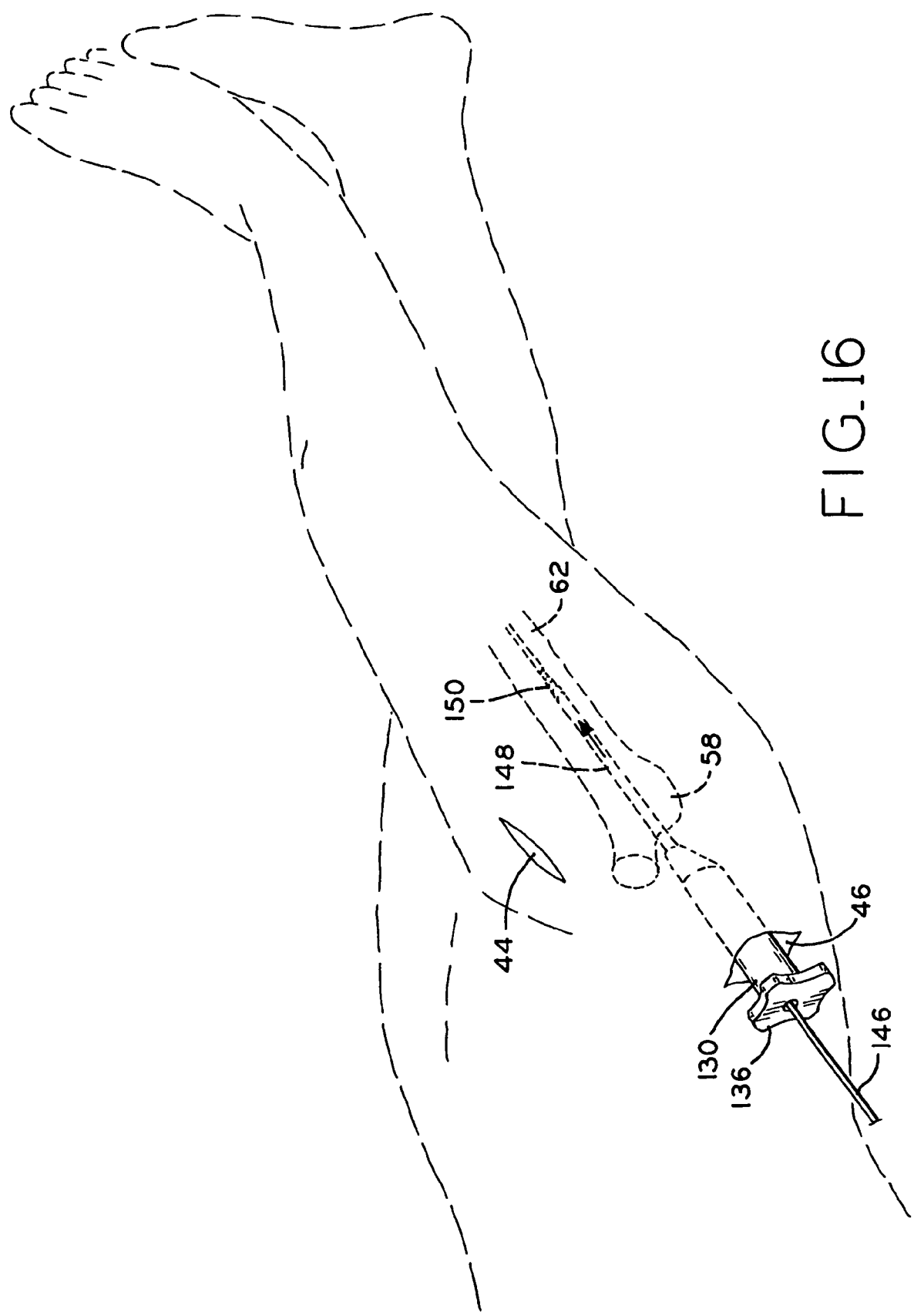
FIG. 16 is a perspective view illustrating reaming of the femoral shaft.
Figure 19:
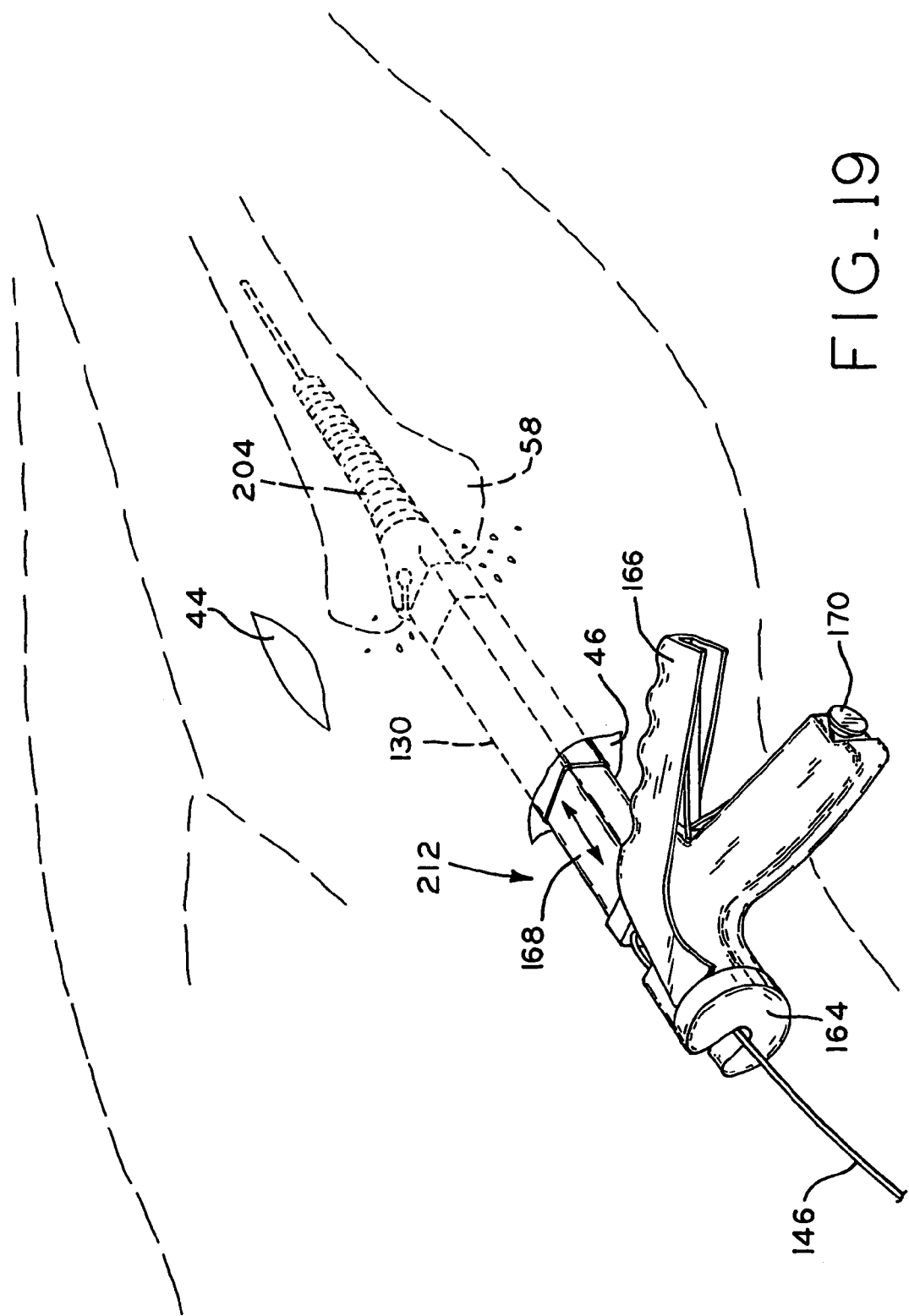
FIG. 19 is a perspective view of a rasp handle after inserting a rasp into the femoral shaft.

FIG. 16 illustrates preparation of femoral canal 148 to receive rasp 204 (FIG. 19). Guide tube 124 is removed from posterior retractor 122 and end cutter 150 (FIG. 17A) is inserted through reamer tunnel 126. FIG. 18 illustrates end cutter 150 positioned within reamer tunnel 126. End cutter 150 includes elongate aperture 160 through which guide wire 146 passes and guides end cutter 150. End cutter 150 is actuated by any of the many actuating devices known in the art. After end cutting is complete, end cutter 150 is removed through reamer tunnel 126 and reamer 151 (FIG. 17B) is inserted therethrough. Reamer 151 includes reamer guide aperture 161 through which guide wire 146 passes and guides reamer 151 as it reams femoral canal 148. Reamers of progressive increase in their outer diameter are sequentially placed over guide wire 146 and femoral canal 148 is reamed until cortical "chatter" is felt. As is known in the art, the optimal diameter of femoral canal 148 is provisionally determined by preoperative templating. Some surgeons may choose to avoid reaming of the femoral shaft and instead utilize a broach as is known in the art. A broach may be inserted in accordance with the current invention as described hereinbelow with respect to rasp insertion. In one exemplary embodiment, lateralizing reamers are utilized to prepare femoral canal 148.

In an alternative embodiment of the present invention, reaming of femoral canal 148 begins with the use of a flexible reamer. The flexible reamer is used to enlarge the femoral canal along its normal axis. In one exemplary embodiment, a cannulated flexible is utilized. In this embodiment, the flexible reamer is positioned over the inserted ball tip guide wire. After reaming with the flexible reamer, lateralizing reamer 480 is inserted through posterior incision 46 and into the femoral canal. Lateralizing reamer 480 is a blunt tipped side cutting reamer. Lateralizing reamer 480 is utilized to remove bone stock into the greater trochanter so that the implanted femoral stem will be coaxial with the shaft of femur 62 and will not be aligned in varus. Stated another way, lateralizing reamer 480 is used to side cut the femoral canal to move the top of the pathway posteriorward allow for proper implantation of the prosthetic femoral component. If a taper fit stem is utilized, then reaming is complete after using the lateralizing reamer. If a fully coated porous stem is utilized, then a straight solid reamer such as the VERSYS reamer available from Zimmer, Inc. is utilized to continue reaming the femoral canal. In all of the reaming steps discussed above, a number of reamers of increasing size can be utilized. For example, when using a flexible reamer, a first flexible reamer can be utilized to ream out the femoral canal, followed by a second flexible reamer larger in size than the first flexible reamer.

After the correct diameter of femoral canal 148 is reamed out, reamer tunnel 126 (FIG. 14) is removed from posterior retractor 122 so that rasp 204 and rasp handle 212 (FIG. 19) can be inserted over guide wire 146 to complete preparation of femur 62. Guide wire 146 is inserted into rasp guide aperture 214 and rasp handle guide aperture 202 to guide rasp 204 to prepared femur 62. Impact surface 164 is struck, as is known in the art, to place rasp 204 in femur 62. While rasp 204 is being impacted, the rotational alignment can be assessed by direct visual scrutiny of femur 62 through anterior incision 44. Furthermore, assessment of the alignment of rasp handle 212 with respect to the patella, lower leg, and foot facilitates alignment. On the normal proximal femoral metaphysis, a flattened area of anterior bone provides a highly reproducable landmark for the rotational alignment. This may not be true if the patient has experienced prior surgery or trauma.

Progressively larger rasps are inserted to achieve the optimal fit and fill in femur 62. Once the final rasp is fully seated, rasp handle 212 is removed along with guide wire 146 and posterior retractor 122, leaving distal end 208 of flexible cable 192 (FIG. 19A) attached to the proximal end of rasp 204 and proximal end 194 of flexible cable 192 protruding from posterior incision 46. The operation of rasp handle 212 will be further explained below. In an alternative embodiment, rasp handle 300 illustrated in FIGS. 31-36 is utilized. Rasp handle 300 can be utilized with a VERSYS rasp available from Zimmer, Inc. The operation of rasp handle 300 and its cooperation with a femoral rasp will be further described hereinbelow. One or more fluoroscopic images can be utilized to ensure proper orientation and position of the femoral rasps.

Figure 22:
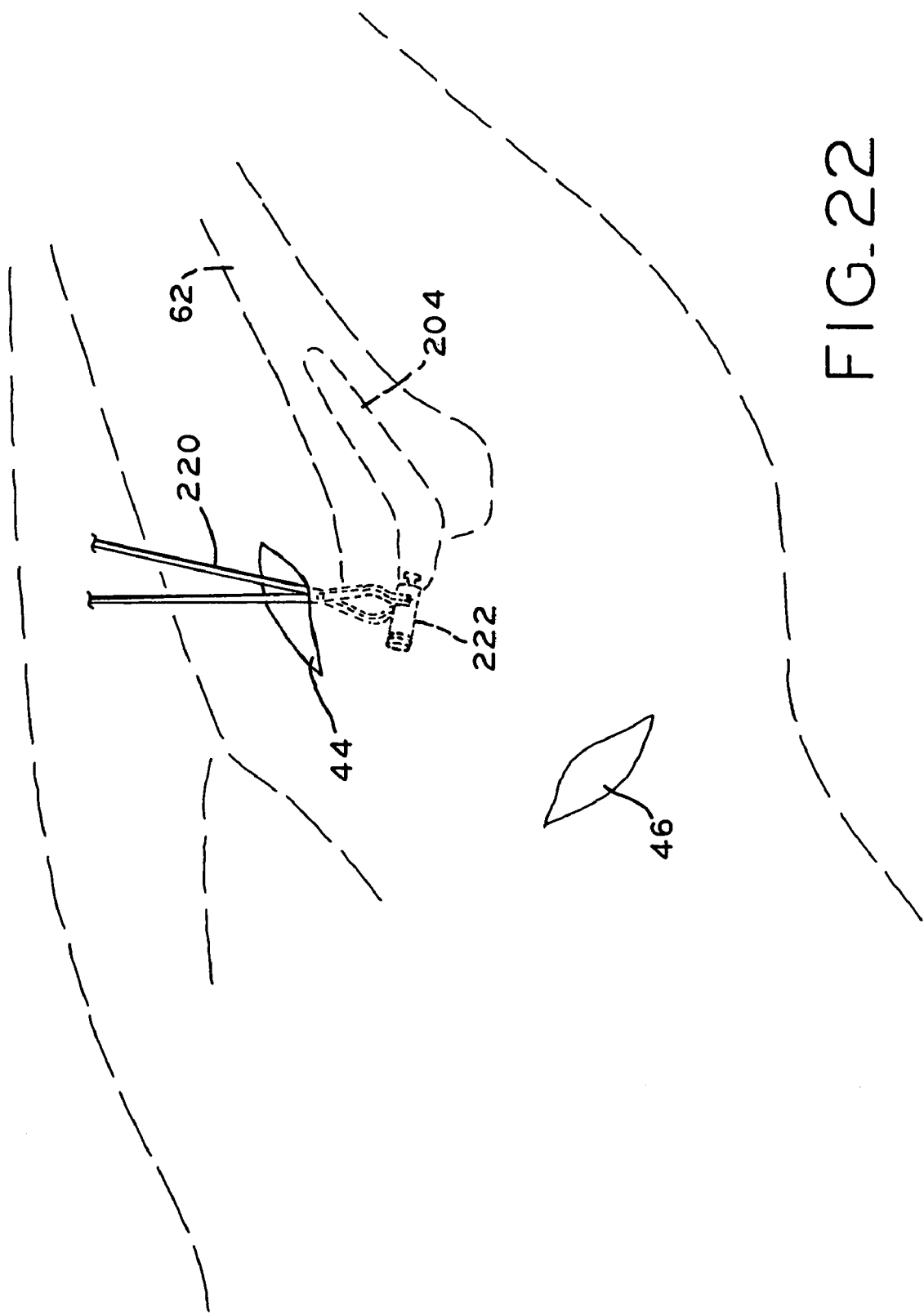
FIG. 22 is a perspective view illustrating placement of a provisional neck of the present invention.

After the final rasp is seated in femoral canal 148, a trial acetabular liner is placed through anterior incision 44 or 44' and into the seated acetabular cup with the use of a liner inserter as is known in the art. In an alternative embodiment, a trial or final acetabular liner can be seated in the seated acetabular cup prior to preparation of femur 62. Provisional neck 222 (FIGS. 23, and 24A-C) is inserted through anterior incision 44 and locked to the top end of the seated rasp, as illustrated in FIG. 22. A trial femoral head is placed on the Morse taper of provisional neck 222 through anterior incision 44. The hip joint is reduced for an assessment of stability of the hip joint and limb length. Where necessary, a second assessment is made. Once the trial reduction is satisfactorily completed, the hip is dislocated and the provisional head and provisional neck 222 are removed. Rasp handle 212 is reinserted through posterior incision 46 over the free end of flexible cable 192. Rasp handle 212 is advanced until it can be locked with the seated rasp so that impact surface 164 can be impacted and the entire tool (i.e., rasp 204 and rasp handle 212) can be removed. The trial acetabular liner is removed through anterior incision 44. In an alternative embodiment, a trial reduction can be performed utilizing the final femoral implant and a trial femoral head. In one exemplary embodiment, a trial femoral head such as the one disclosed in U.S. patent application Ser. No. 09/992,639 filed Nov. 6, 2001 and published as U.S. Publication No. U.S. 2002/0099447 A1, the disclosure of which is hereby explicitly incorporated by reference herein.

Figure 29:
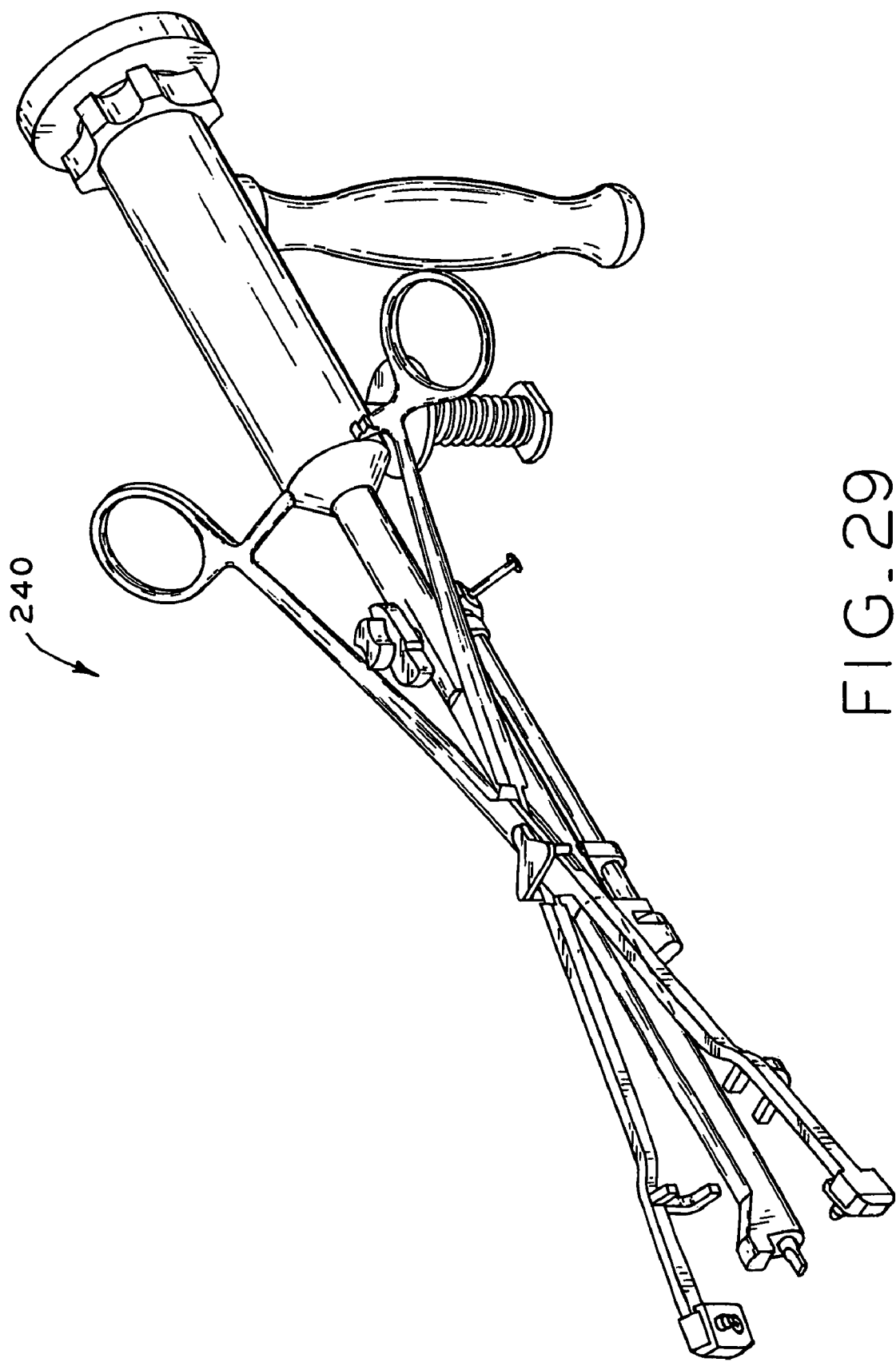
FIG. 29 is a perspective view of a femoral stem insertion tool in accordance with the teachings of the present invention.
Figure 30:
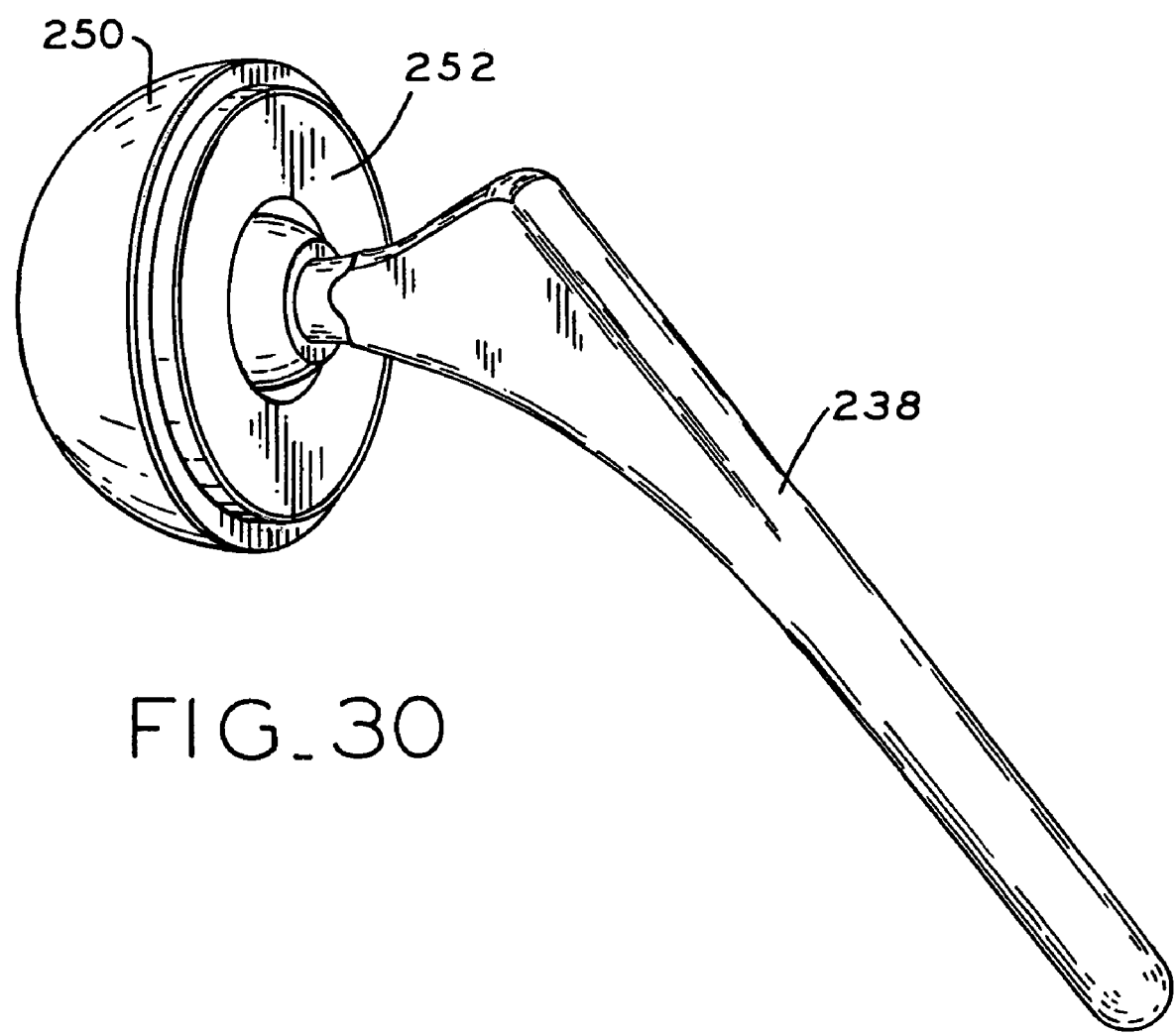
FIG. 30 is a perspective view of a hip prosthesis which can be implanted according to the method of the current invention.

Via anterior incision 44, the final acetabular liner 252 (FIG. 30) is seated into acetabular cup 250 (FIG. 30) with a liner inserter that permits its impaction in place, as is known in the art. Femoral implant 238 (FIG. 30) is anchored to femoral stem insertion tool 240 (FIG. 29) and placed through posterior incision 46 or 46'. Femoral implant 238 can be, e.g., a VERSYS fiber metal taper, a VERSYS fiber metal midcoat, or a VERSYS full coat stem available from Zimmer, Inc. As illustrated in FIG. 25, femoral implant 238 is placed in protective, disposable bag 242 prior to its introduction into posterior incision 46 or 46'. Protective, disposable bag 242 keeps femoral implant 238 clean as it is inserted through posterior incision 46. Note that FIG. 25 illustrates femoral implant 238 oriented as it will be when placed in femur 62. To insert femoral implant 238 through posterior incision 46, femoral implant 238 can be rotated 180° from this position to prevent impingement on the body. Femoral implant 238 is then rotated 180° after being completely inserted through posterior incision 46. Similar rotations of femoral implant 238 can be made when utilizing posterior incision 46'.

Figure 26:
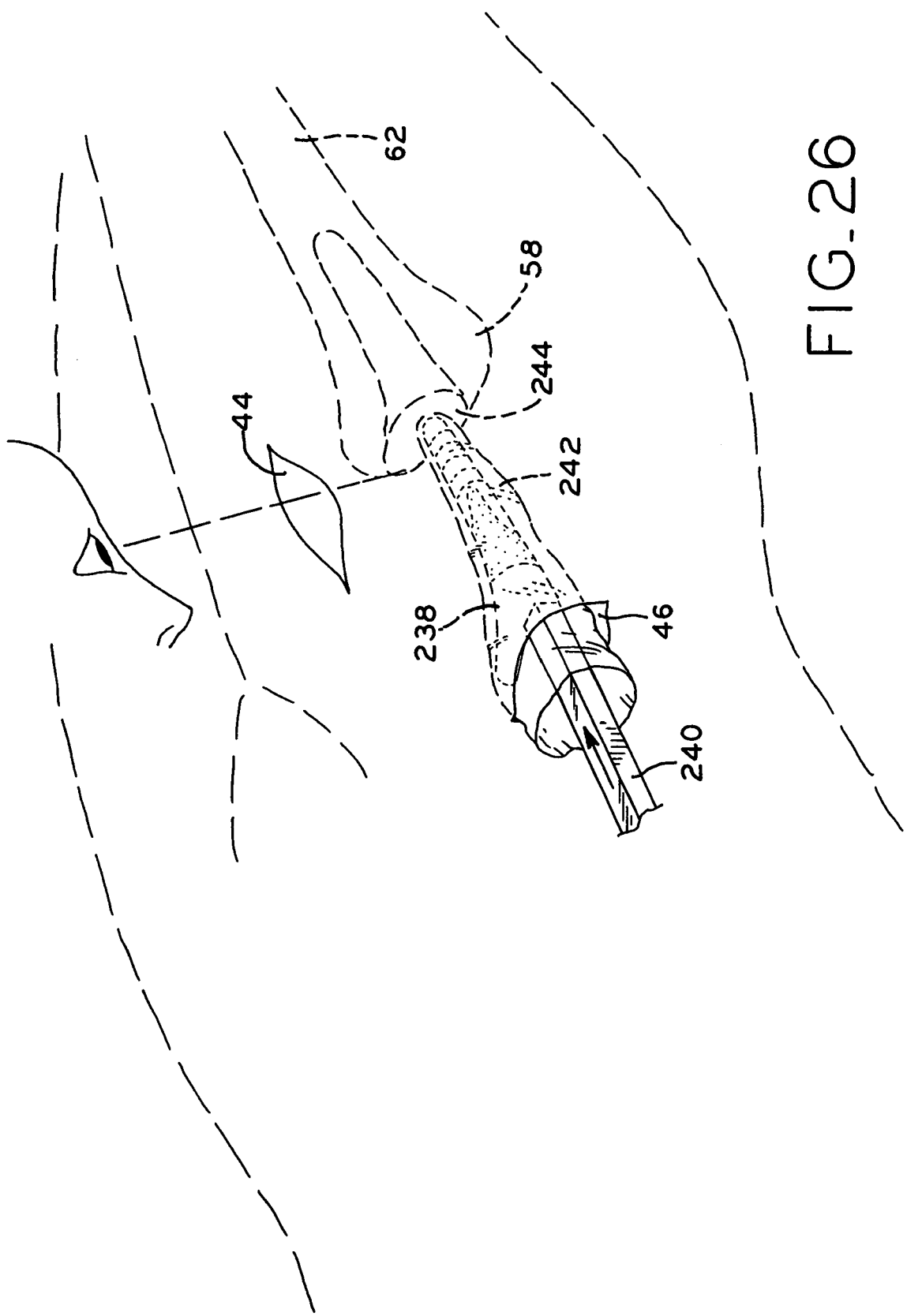
FIG. 26 is a perspective view illustrating alignment of the femoral stem while observing through the anterior incision.
Figure 27:
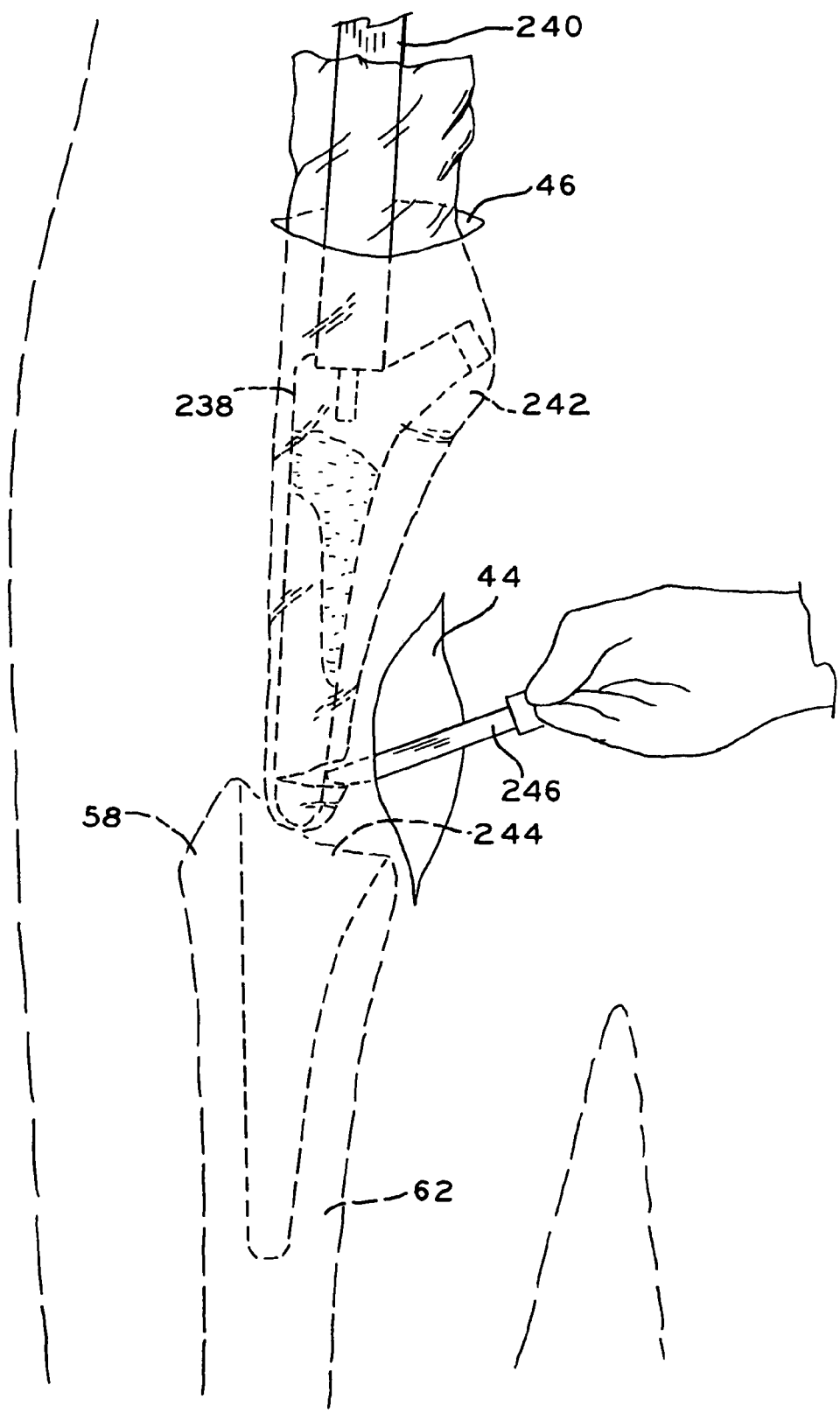
FIG. 27 illustrates an incision into the femoral stem protective bag prior to insertion of the femoral stem into the femoral shaft.
Figure 28:
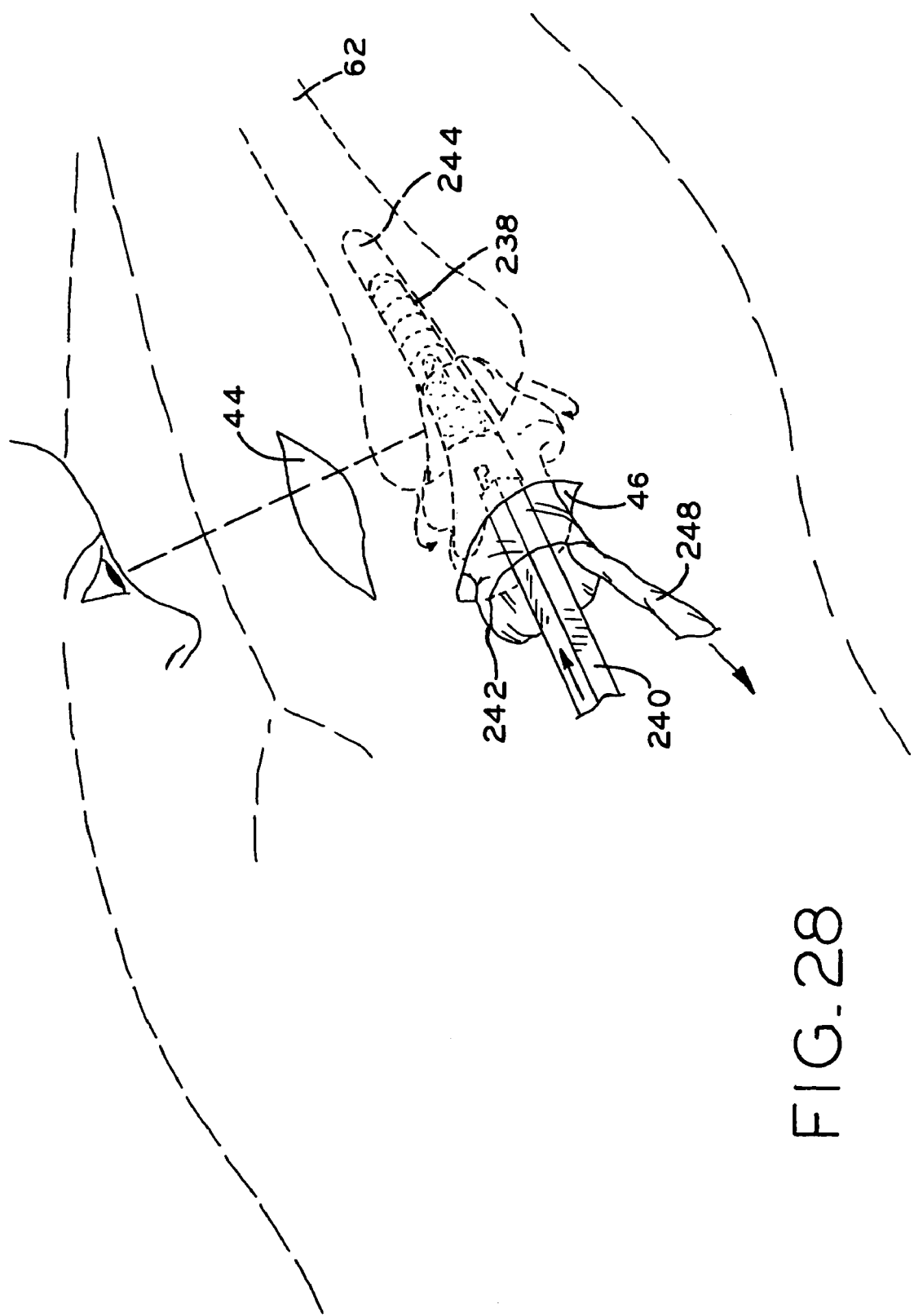
FIG. 28 is a perspective view illustrating removal of the femoral stem protective bag while inserting the femoral stem, with observation through the anterior incision.

FIG. 26 illustrates femoral stem 238 and bag 242 inserted through posterior incision 46. When the tip of femoral stem 238 approaches the osteotomized femoral neck, the distal end of bag 242 is incised as illustrated in FIG. 27. Scalpel 246 is inserted into anterior incision 44 to incise bag 242. As femoral stem 238 is driven into femoral canal 148, bag 242 is progressively removed through posterior incision 46 as illustrated in FIG. 28. After femoral stem 238 is fully seated, femoral stem insertion tool 240 (FIG. 29) is removed through posterior incision 46. Through anterior incision 44, the final femoral head is positioned on the femoral neck Morse taper using a standard holding device and secured with a standard impaction tool and mallet. The hip is then reduced and assessed for stability. While described with reference to anterior incision 44 and posterior incision 46, this method of seating femoral stem 238 is equally applicable when using anterior incision 44' and posterior incision 46'.

After appropriate antibiotic irrigation and pulsatile lavage, the hip capsule and the soft tissues are repaired with heavy sutures or staples. A suitable local anesthetic solution is injected into the closed hip joint as well as the capsular layer and the subcutaneous tissues, allowing superior postoperative pain relief. The fascial layers, subcutaneous tissues, and skin of both the anterior and posterior wounds are closed in a conventional method and dressings are applied. A suction drain may be used at the discretion of the surgeon.

Figure 5A:
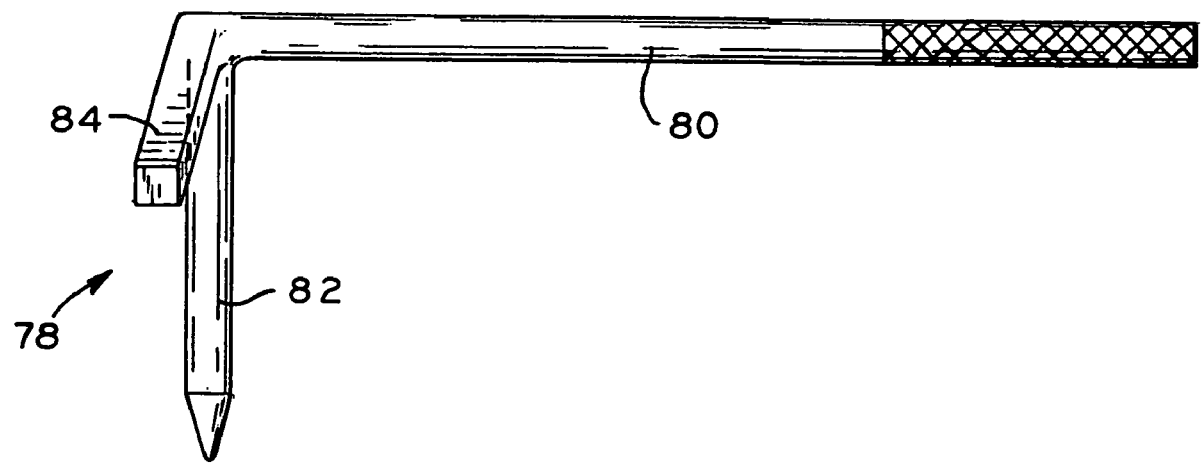
FIG. 5A is a side elevational view of an alternative embodiment of an osteotomy guide in accordance with the present invention.
Figure 5B:
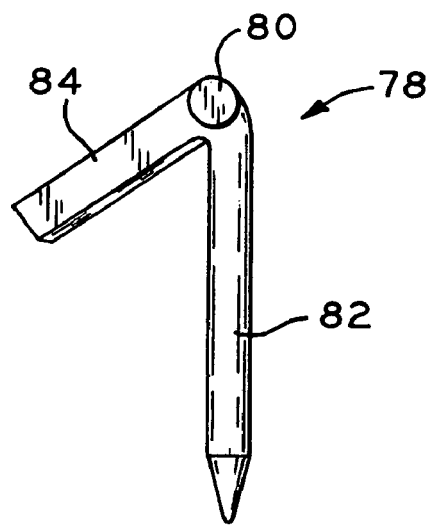
FIG. 5B is an elevational view thereof taken along the longitudinal axis of the handle.

Osteotomy guide 78, illustrated in use in FIG. 4, includes handle 80, alignment portion 82, and cut guide 84. In one exemplary embodiment, cut guide 84 and alignment portion 82 form a 60° angle. In one exemplary embodiment, alignment portion 82 includes a tapered distal end as illustrated in FIGS. 5A and 5B. Osteotomy guide 78 is inserted through anterior incision 44 and is positioned with alignment portion 82 placed on femur 62 so that alignment portion 82 generally aligns with the longitudinal axis of femur 62. Handle 80 protrudes through anterior incision 44 and may be utilized to position osteotomy guide 78. After osteotomy guide 78 is properly positioned, cut guide 84 is utilized to mark cut line 85 on femoral neck 60 as illustrated in FIG. 4. Osteotomy guide 78 can be formed to function on either side of the body. FIG. 4 illustrates an osteotomy guide designed to function on the right femur, while FIG. 5B illustrates an osteotomy guide operable to function on the left femur.

Figure 37:
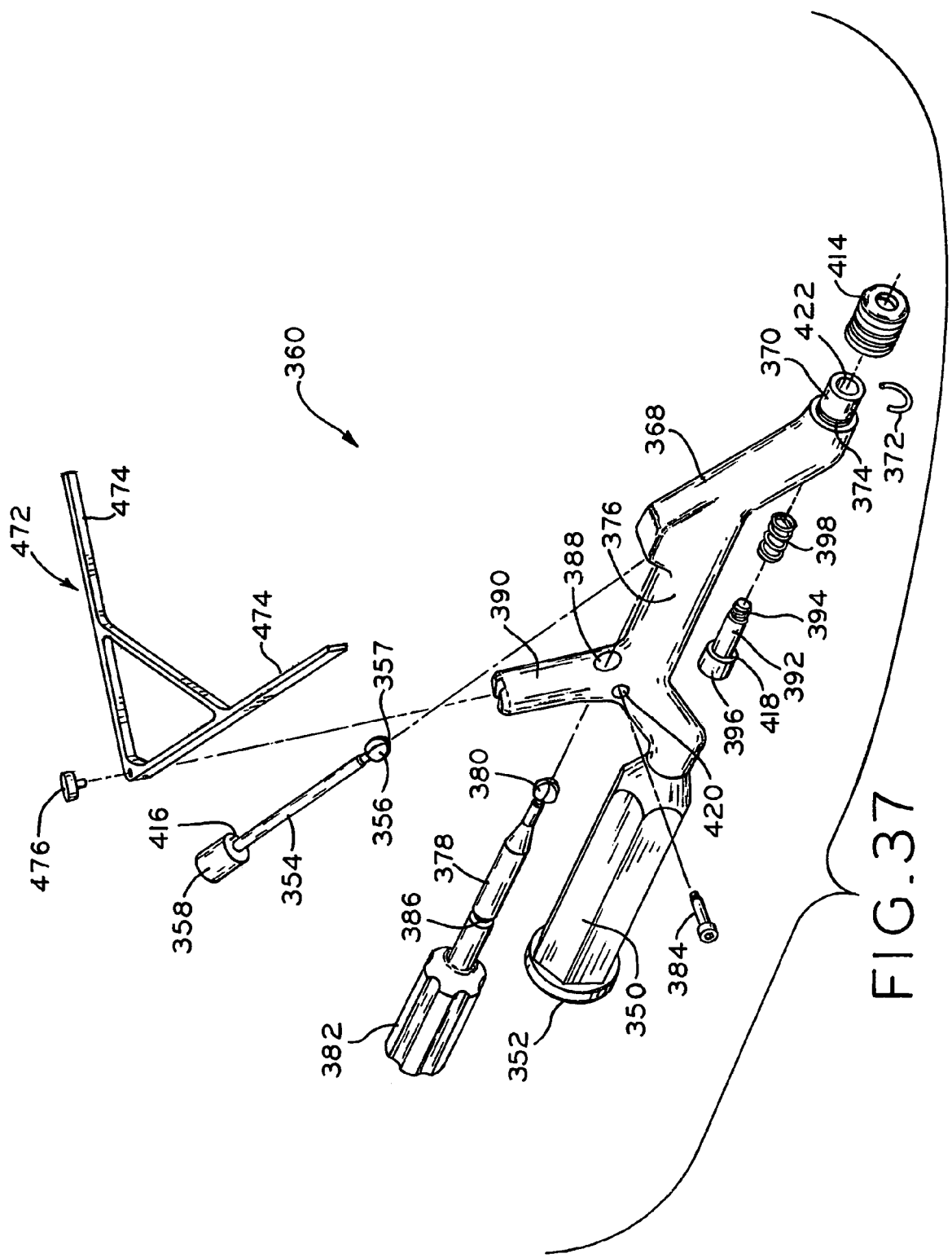
FIG. 37 is an exploded perspective view of a cup inserter of the present invention.

FIGS. 37-45 illustrate cup inserter 360 of the present invention. Cup inserter 360 is particularly advantageous when performing the minimally invasive total hip arthroplasty of the present invention due in part to the offset of offset frame leg 376 from the remainder of frame 368. This offset advantageously allows for placement of an acetabular cup in the correct anteversion and abduction without interference from soft tissue. Referring to FIG. 37, acetabular cup inserter 360 includes frame 368 having handle 350 secured to a proximal end thereof. Handle 350 includes impaction surface 352 useful in impacting an acetabular cup such as a press fit or spiked acetabular cup. Distal end 370 of frame 360 is adapted for connection of the acetabular cup thereto as will be further described hereinbelow.

Referring to FIGS. 37 and 38, drive shaft 378 of cup inserter 360 is rotated via drive shaft handle 382, or torque handle 432 if it is provided. Rotation of drive shaft 378 operates to rotate threaded distal end 394 of threaded shaft 392 to secure or release an acetabular cup to cup inserter 360 as will be further described hereinbelow. Drive shaft handle 382 may include a ratchet mechanism and may further include a clutch to limit applied torque so that the acetabular cup is not secured too tightly to cup inserter 360. As illustrated in FIG. 38, acetabular cup inserter 360 includes threaded shaft 392 having threaded distal end 394 protruding from the distal end of acetabular cup inserter 360. Threaded distal end 394 of threaded shaft 392 is threaded into a threaded central aperture of an acetabular cup to secure the acetabular cup to cup inserter 360. After seating of the acetabular cup, threaded shaft 392 is rotated to release the acetabular cup from engagement with cup inserter 360. To secure or release an acetabular cup to cup inserter 360, torque is applied to drive shaft 378 through one or both of drive shaft handle 382 and torque handle 432. As illustrated in FIGS. 37 and 38, drive shaft 378 is positioned through drive shaft aperture 388 formed in frame 368 of cup inserter 360. Drive shaft 378 includes drive shaft retaining groove 386 into which drive shaft retaining pin 384 is positioned as illustrated in FIG. 38 to prohibit axial displacement of drive shaft 378. In assembly, distal end 380 of drive shaft 378 is positioned within proximal end 358 of connecting shaft 354 as illustrated in FIG. 38. In assembly, connecting shaft 354 occupies connecting shaft aperture 426 (FIG. 39) of frame 368. As illustrated in FIG. 39, connecting shaft aperture 426 includes a counterbore forming shoulder 428. Proximal end 358 of connecting shaft 354 similarly includes shoulder 416 as illustrated in FIG. 37. In construction, shoulder 416 of connecting shaft 354 abuts shoulder 428 of connecting shaft aperture 426 to limit axial displacement of connecting shaft 354 relative to frame 368 of acetabular cup inserter 360.

As illustrated in FIG. 38, distal end 380 of drive shaft 378 is positioned within proximal end 358 of connecting shaft 354. Distal end 380 of drive shaft 378 is identical to distal end 356 of connecting shaft 354 illustrated in detail in FIGS. 42-45 and further described hereinbelow. In assembly, threaded shaft 392 is positioned within threaded shaft aperture 422 (FIG. 39) of frame 368. As illustrated in FIG. 39, threaded shaft aperture 422 includes a counterbore forming shoulder 424. Similarly, proximal end 396 of threaded shaft 392 includes shoulder 418. In construction, spring 398 (FIG. 37) is, in one exemplary embodiment, positioned about threaded shaft 392, intermediate shoulder 418 of threaded shaft 392, and shoulder 424 of threaded shaft aperture 422. As illustrated in FIG. 38, distal end 356 of connecting shaft 354 is positioned within proximal end 396 of threaded shaft 392. Distal end 380 of drive shaft 378 and proximal end 358 of connecting shaft 354 cooperate to form a universal joint. Similarly, distal end 356 of connecting shaft 354 and proximal end 396 of threaded shaft 392 cooperate to form a universal joint.

As described supra, distal end 380 of drive shaft 378 is substantially identical to distal end 356 of connecting shaft 354. Similarly, proximal end 358 of connecting shaft 354 is substantially identical to proximal end 396 of threaded shaft 392. The structure of the universal joint formed by distal end 356 of connecting shaft 354 and proximal end 396 of threaded shaft 392 will now be described in detail. The structure and function of the universal joint formed by distal end 380 of drive shaft 378 and proximal end 358 of connecting shaft 354 is identical to the universal joint formed by distal end 356 of connecting shaft 354 and proximal end 396 of threaded shaft 392 and will not be described in detail for the sake of brevity.

Figure 40:
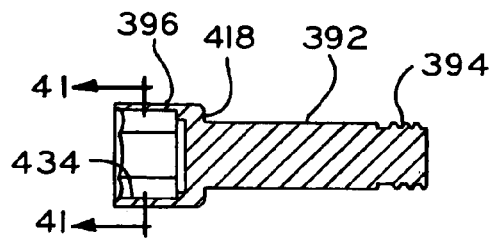
FIG. 40 is a sectional view of a threaded shaft used to engage an acetabular cup in conjunction with the cup inserter illustrated in FIGS. 37 and 38.
Figure 41:
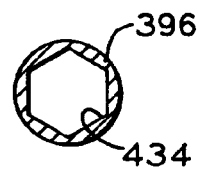
FIG. 41 is a sectional view thereof.
Figure 42:
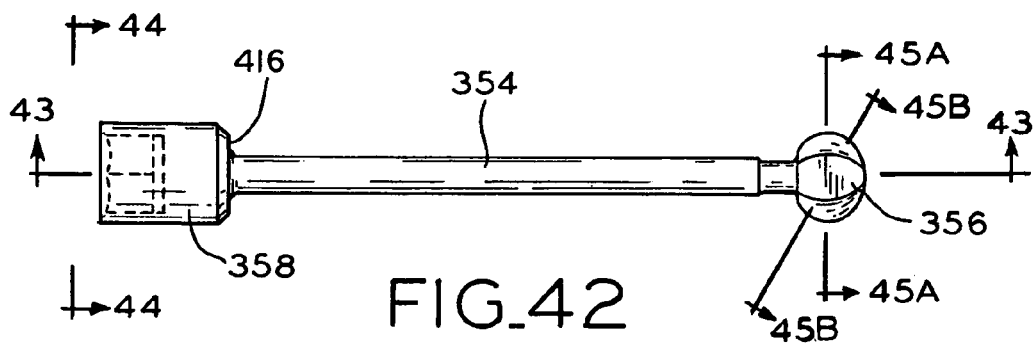
FIG. 42 is a side elevational view of a connecting shaft of the cup inserter illustrated in FIGS. 37 and 38.
Figure 43:
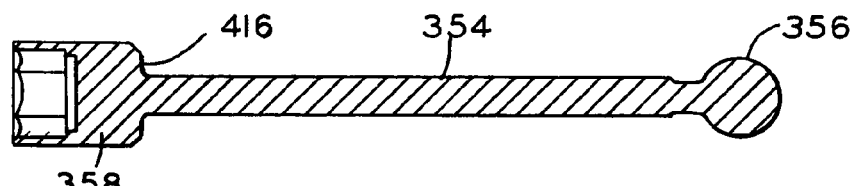
FIG. 43 is a sectional view thereof.
Figure 44:
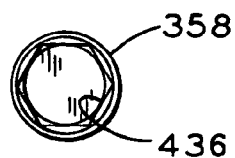
FIG. 44 is an end elevational view thereof.
Figure 45A:
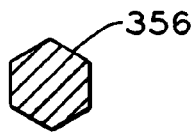
FIG. 45A is a sectional view taken along line 45A-45A of FIG. 42.

As illustrated in FIGS. 40 and 41, proximal end 396 of threaded shaft 392 includes drive aperture 434 having a hexagonal cross section as illustrated in FIG. 41. Similarly, distal end 356 of connecting shaft 354 has a hexagonal cross section as illustrated in FIG. 45A. As illustrated in FIGS. 37 and 42, distal end 356 of connecting shaft 354 comprises a six sided spheroid. Taking distal most point 357 (FIG. 37) of distal end 356 as a pole of the spheroid, an opposing, imaginary pole is positioned within connecting shaft 354. To form the six sided spheroid of distal ends 356 and 380 of connecting shaft 354 and drive shaft 378, a sphere can be machined such that a straight edged tool intersecting a first pole, e.g., distal most point 357, and positioned perpendicular to a primary axis formed by distal most point 357 and the opposing imaginary pole, can be moved from distal most point 357 toward the opposing imaginary pole while maintaining the straight cutting edge of this instrument perpendicular to the primary axis. This procedure can be repeated at six evenly spaced intervals about the periphery of the sphere to form the six sided spheroid of distal ends 356 and 380.

Figure 45B:
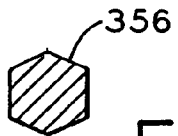
FIG. 45B is a sectional view taken along line 45B-45B of FIG. 42.

As illustrated in FIG. 38, distal end 380 of drive shaft 378 is positioned within proximal end 358 of connecting shaft 354 such that connecting shaft 354 and drive shaft 378 are not colinear. FIG. 45B illustrates a section of distal end 356 (which is identical to distal end 380) taken along a line transverse to proximal end 358 of connecting shaft 354 when connecting shaft 354 is assembled in cup inserter 360 as illustrated in FIG. 38. As illustrated in FIG. 45B, the spheroidal shape of the male aspect of the universal joints of the present invention will provide linear contact surfaces for the hexagonal sides of the female aspect of the universal joint of the present invention when the female aspect is angled relative to the male aspect. In this way, torque can be transmitted from the male aspect of a universal joint of the present invention to a female aspect in a nonlinear fashion.

The universal joints of cup inserter 360 allow for transmission of torque applied to one or both of drive shaft handle 382 and torque handle 432 through drive shaft 378, connecting shaft 354, and threaded shaft 392. Therefore, rotation of drive shaft handle 382 and/or torque handle 432 will rotate threaded distal end 394 of threaded shaft 392 to secure an acetabular cup to acetabular cup inserter 360, or to allow for detachment of an acetabular cup from acetabular cup inserter 360. When securing an acetabular cup to acetabular cup inserter 360, threaded distal end 394 of threaded shaft 392 is rotated relative to the acetabular cup to engage the acetabular cup thereto. As the acetabular cup is secured to acetabular cup inserter 360, threaded shaft 392 may be drawn distally through threaded shaft aperture 422 (FIG. 39) to allow for additional exposure of threaded distal end 394 and provide for secure engagement of an acetabular cup to acetabular cup inserter 360. When this occurs, threaded shaft 392 acts against the biasing force of spring 398. This extension aspect of threaded shaft 392 is particularly advantageous when using a relatively small acetabular cup, which requires additional threads for engagement therewith, relative to a larger acetabular cup.

As illustrated in FIGS. 37 and 39, distal end 370 of acetabular cup inserter 360 includes C-ring groove 374. In construction, C-ring groove 374 accommodates C-ring 372 (FIG. 37). With C-ring 372 positioned about C-ring groove 374, end cap 414 can be positioned about distal end 370 of acetabular cup inserter 360 and locked in place, with C-ring 372 acting to create an interference fit with end cap 414. When an acetabular cup is secured to acetabular cup inserter 360, threaded shaft 392 draws the interior of the acetabular cup into locked engagement with end cap 414, forcing the proximal end of end cap 414 into secure engagement with frame 368 of acetabular cup inserter 360. Therefore, impaction force applied to impaction surface 352 will be transmitted through frame 368 to the acetabular cup. Impaction force will not be transmitted through the universal joint linkage described hereinabove. In one exemplary embodiment, end cap 414 is made of polyethylene.

Figure 46:
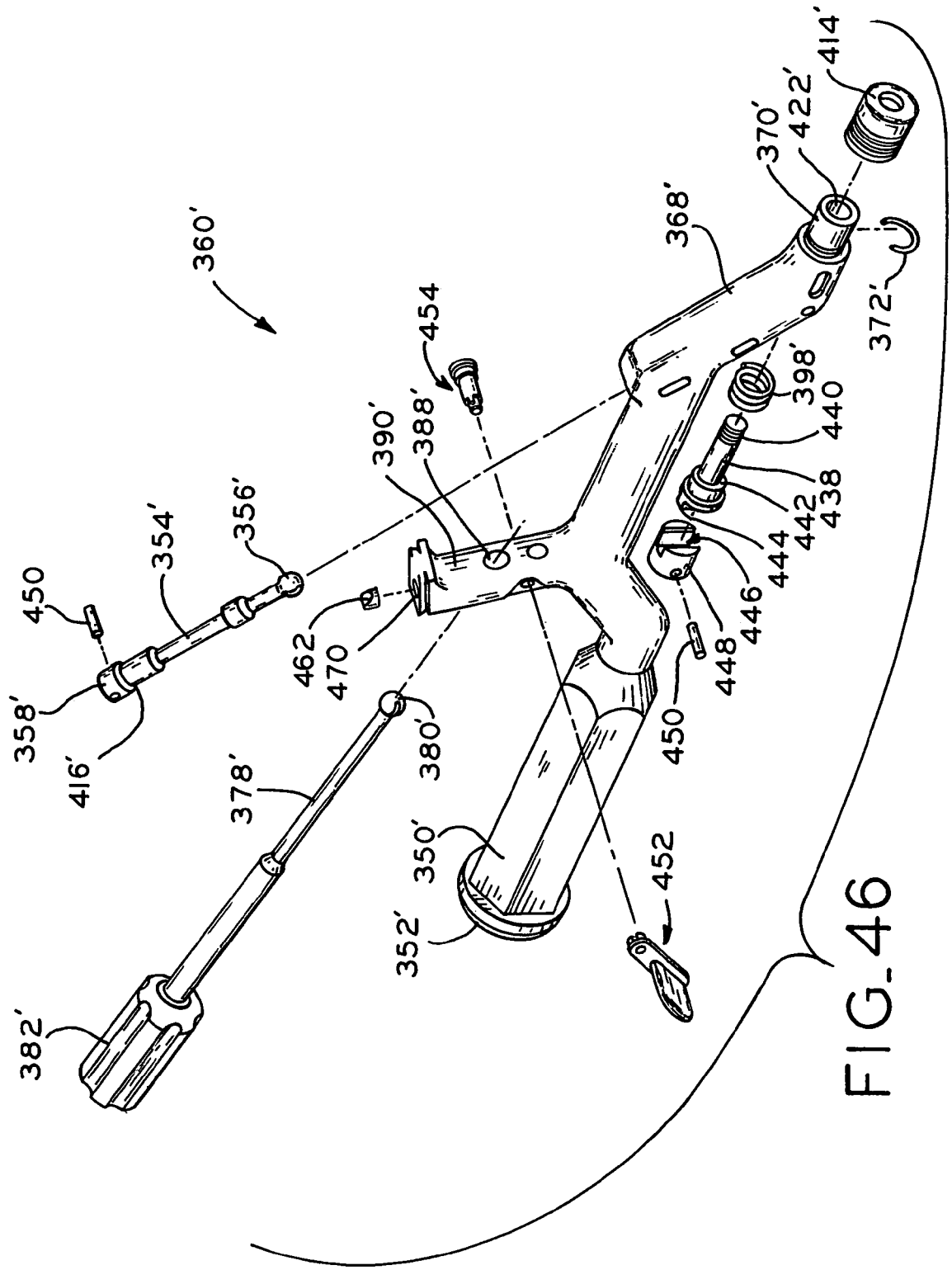
FIG. 46 is an exploded perspective view of another acetabular cup inserter in accordance with the present invention.
Figure 47:
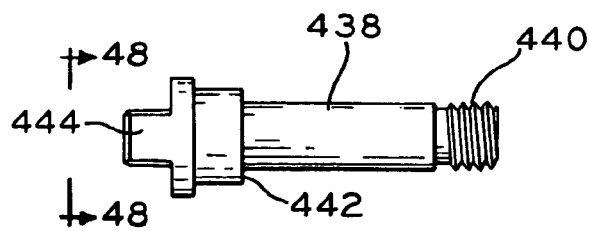
FIG. 47 is a radial elevational view of a threaded shaft used to engage an acetabular cup in conjunction with the cup inserter illustrated in FIG. 46.
Figure 48:
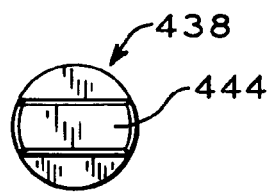
FIG. 48 is an axial elevational view thereof.
Figure 49:
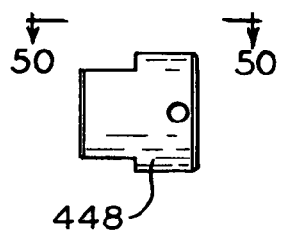
FIG. 49 is a radial elevational view of a U-joint linkage in accordance with the present invention.
Figure 50:
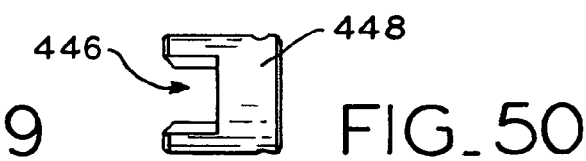
FIG. 50 is a second radial elevational view thereof, rotated 90° with respect to FIG. 49.

FIG. 46 illustrates alternative embodiment acetabular cup inserter 360'. Acetabular cup inserter 360' shares many similar components with acetabular cup inserter 360. Components of acetabular cup inserter 360' which are identical or significantly similar to corresponding components of acetabular cup inserter 360 are designated with primed reference numerals. Acetabular cup inserter 360' utilizes a universal joint linkage to transmit torque applied to drive shaft handle 382' to threaded shaft 438. The universal joints of acetabular cup inserter 360' differ from those described above with respect to acetabular cup inserter 360 in that they are pinned universal joints. Because pinned universal joints are utilized with acetabular cup inserter 360', U-joint linkage 448 is provided. U-joint linkage 448 is secured via U-joint pin 450 to distal end 356' of connecting shaft 354'. U-joint linkage 448 includes groove 446 into which tab 444 of threaded shaft 438 is positioned to allow for torque transmission to threaded shaft 438. Tab 444 and groove 446 are sized to allow for maximum extension of threaded shaft 438 from frame 368' as described hereinabove with respect to acetabular cup inserter 360. Threaded shaft 438 and U-joint linkage 448 are illustrated in detail in FIGS. 47-50.

Figure 51:
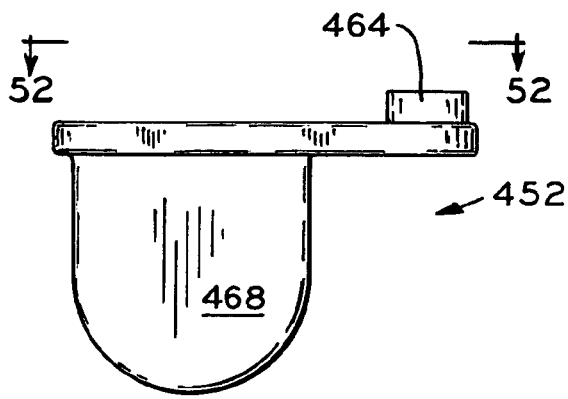
FIG. 51 is a top elevational view of a locking lever in accordance with the present invention.
Figure 52:
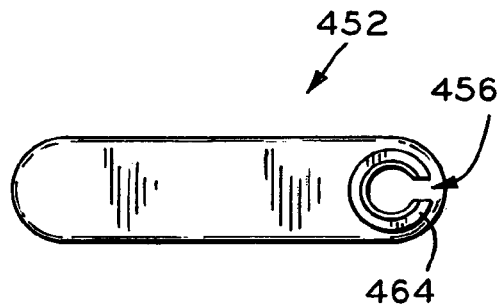
FIG. 52 is a side elevational view thereof.
Figure 53:
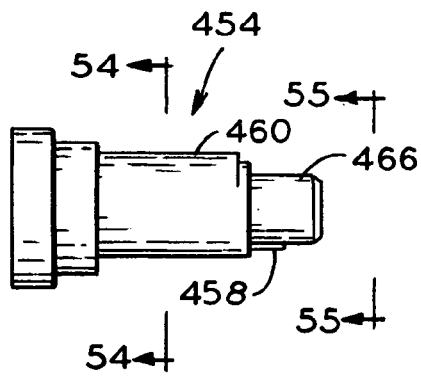
FIG. 53 is a radial elevational view of a locking shaft in accordance with the present invention.
Figure 54:
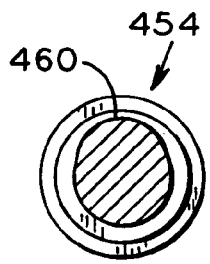
FIG. 54 is a sectional view thereof taken along line 54-54 of FIG. 53.
Figure 55:
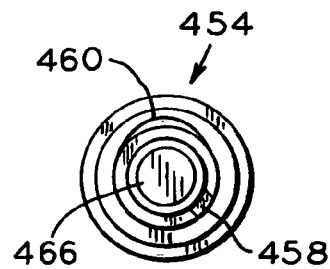
FIG. 55 is an axial elevational view of the locking shaft depicted in FIG. 53.

Acetabular cup inserter 360' includes a locking mechanism for restricting rotational movement of drive shaft 378'. Locking lever 452 and locking shaft 454 are illustrated in FIG. 46 and cooperate with lifter 462 to create an interference fit between drive shaft 378' and frame 368' to prohibit rotational movement of drive shaft 378'. Locking lever 452 and locking shaft 454 are illustrated in detail in FIGS. 51-55. As illustrated in FIG. 51, locking lever 452 includes partial cylindrical wall 464 having locking tab aperture 456 formed therein. Locking shaft 454 includes locking tab 458 formed on distal end 466 thereof. In assembly, distal end 466 of locking shaft 454 is positioned within partial cylindrical wall 464 of locking lever 452, with locking tab 458 positioned within locking tab aperture 456 to prohibit relative rotational movement of locking lever 452 and locking shaft 454. As illustrated in FIGS. 53-55, locking shaft 454 includes cam 460. In assembly, cam 460 is aligned with lifter aperture 470 (FIG. 46) of frame 368'. Lifter 462 is positioned within lifter aperture 470 atop locking shaft 454. Locking lever 452 includes tab 468 against which force can be applied to rotate locking shaft 454. Specifically, locking shaft 454 can be rotated until cam 460 does not contact lifter 462 to allow for rotation of drive shaft 378'. Similarly, locking shaft 454 may be rotated until cam 460 forces lifter 462 into frictional engagement with drive shaft 378' to prohibit rotational movement thereof. When locking lever 452 is rotated to lock drive shaft 378, lifter 462 is forced into engagement with drive shaft 378' and drive shaft 378' is forced into engagement with the interior wall of drive shaft aperture 388' to frictionally lock drive shaft 378'. The locking mechanism described with respect to acetabular cup inserter 360' may be applied to acetabular cup inserter 360 as well. This locking mechanism is advantageous because it will prohibit relative rotation between an acetabular cup secured to acetabular cup inserter 360', and acetabular cup inserter 360'.

After locking an acetabular cup to acetabular cup inserter 360', drive shaft handle 382 may be rotated to rotate the acetabular cup relative to acetabular cup inserter 360'. This feature allows for placement of the acetabular cup locking mechanism in a desirable location to allow for revision surgery. Once the desired orientation of the acetabular cup is achieved, the locking mechanism may be utilized to prohibit further relative rotation of the acetabular cup relative to acetabular cup inserter 360' as described above. While both acetabular cup inserter 360 and acetabular cup inserter 360' have been described as utilizing a pair of universal joints to transmit torque along a nonlinear path, both acetabular cup inserter 360 and 360' may utilize a flexible shaft to transmit torque from drive handle 382, 382' to threaded shaft 392, 438, respectively.

FIG. 9B illustrates use of acetabular cup inserter 360. To properly align acetabular cup inserter 360 for optimum placement of an acetabular cup, A-frame 472 is secured via set screw 476 to alignment frame post 390. With A-frame 472 secured to acetabular cup inserter 360, A-frame 472 is positioned parallel to a coronal plane, as illustrated in FIG. 9B, with one A-frame leg 474 parallel to a sagittal plane and one A-frame leg 474 perpendicular to a sagittal plane. With A-frame 472 positioned in this way, the optimum orientation of the acetabular cup is achieved. In one exemplary embodiment, proper alignment of A-frame 472, as described above, leads to an acetabular cup orientation having 20° of anteversion and 45° of abduction. In an alternative embodiment, an image guidance array can be secured to alignment frame post 390 to allow for computer assisted guidance of acetabular cup inserter 360. In alternative embodiments, cup inserters 360, 360' are utilized with a patient in an alternative position, such as, e.g., a lateral position. In these embodiments, different reference frames having different points of reference can be utilized.

Figure 12:
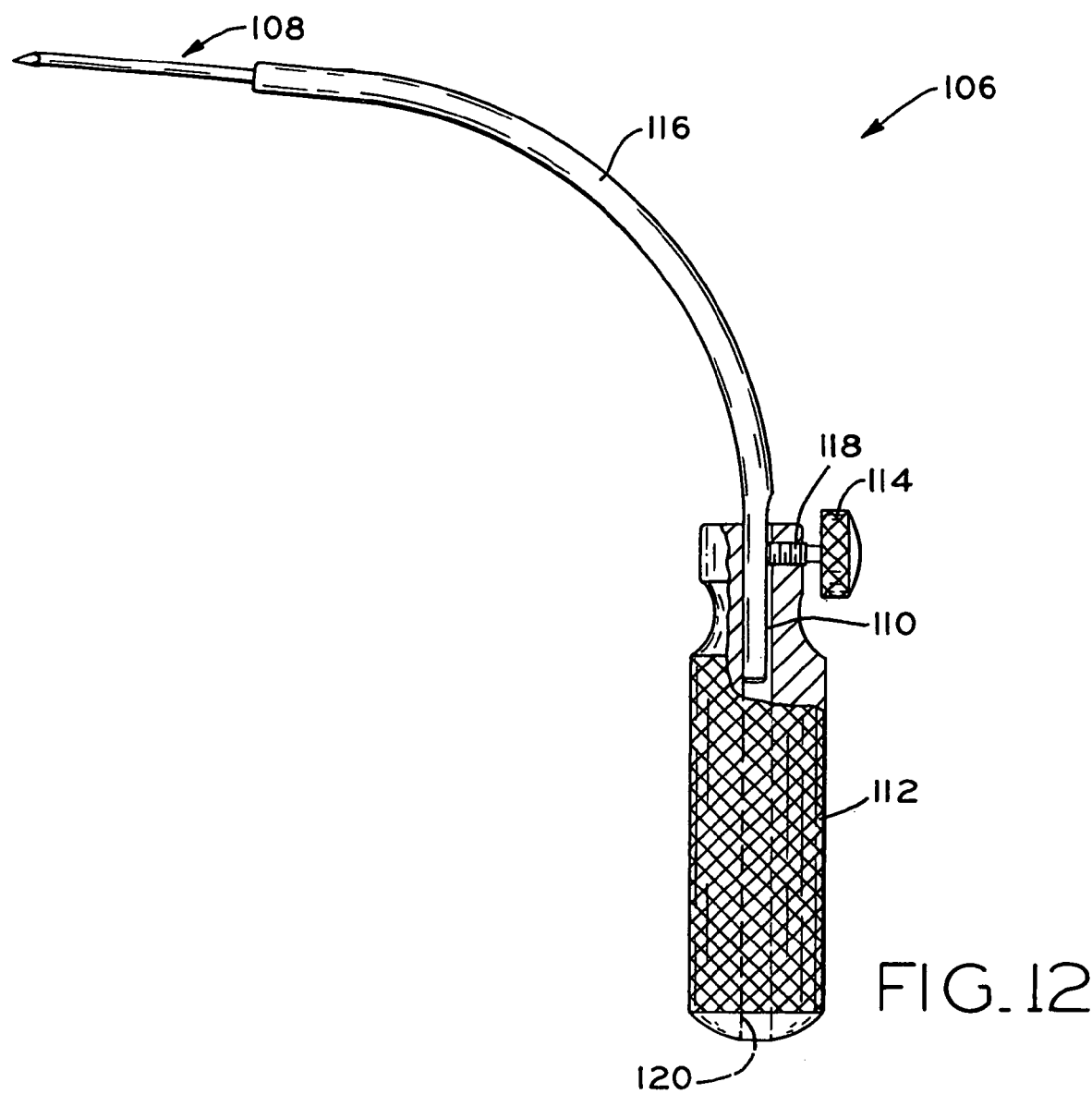
FIG. 12 is a side elevational, partial sectional view of an awl in accordance with the present invention.

As discussed supra, awl 106 (FIG. 12) is designed for insertion through anterior incision 44 or 44' to locate posterior incision 46 or 46'. Awl shaft 116 includes proximal end 110 designed for insertion into handle 112. Handle 112 includes a longitudinal channel 120 into which proximal end 110 of awl shaft 116 may be inserted. Locking screw 118 is operably positioned in handle 112 and may be actuated by locking knob 114. Locking knob 114 is utilized to place locking screw 118 in locking engagement with proximal end 110 of awl 106. In one exemplary embodiment, proximal end 110 of awl 106 includes a flat portion to engage locking screw 118 and facilitate the locking engagement of awl shaft 116 to handle 112. Awl shaft 116 further includes distal end 108. Distal end 108 is generally straight and is utilized to generally align with a longitudinal axis of femur 62 (FIG. 11). As illustrated in FIG. 12, distal end 108 of awl shaft 116 includes a tapered end to facilitate insertion of awl 106 through anterior incision 44 or 44' to locate posterior incision 46 or 46'. Additionally, distal end 108 of awl 106 may be of smaller diameter than the body of awl shaft 116 as illustrated in FIG. 12. In an alternative embodiment, awl 106 is formed in one piece and is disposable.

Referring now to FIG. 14, posterior retractor 122 comprises three nested parts. Guide tube 124 is nested in reamer tunnel 126 while reamer tunnel 126 is nested in rasp tunnel 130. When posterior retractor 122 is threaded into posterior incision 46 or 46', guide tube 124, reamer tunnel 126, and rasp tunnel 130 can be nested together to form a single unit. Rasp tunnel 130 includes exterior threads 132 to facilitate threading of posterior retractor 122 through posterior incision 46. Rasp tunnel 130 includes rasp aperture 134 through which reamer tunnel 126 may be inserted and, in one alternative embodiment, posterior lip 128 for positioning posterior retractor 122, as discussed above. Reamer tunnel 126 includes flange 136 which is operable to retain the position of reamer tunnel 126 within rasp tunnel 130. Reamer tunnel 126 includes reamer aperture 138 through which guide tube 124 may be inserted. Guide tube 124 includes a tapered distal end 140 to facilitate its insertion into reamer aperture 138. Guide tube 124 includes guide wire aperture 144 through which guide wire 146 (FIG. 15) may be inserted. Reamer aperture 138 is sized to allow insertion of end cutter 150 (FIG. 18), or femoral reamer 151 as discussed above. As illustrated in FIG. 18, guide tube 124 is removed from reamer tunnel 126 and end cutter 150 is inserted through reamer aperture 138. Longitudinal reamer aperture 138 is sized to accommodate guide cylinders 156 and to thereby provide guidance and stability to end cutter 150. After end cutting (and reaming, if desired) is complete, reamer tunnel 126 is removed from rasp tunnel 130. Rasp aperture 134 is sized to accommodate insertion of rasp 204 as well as cannular insertion member 168 of rasp handle 212. For surgeries which do not utilize reaming, the posterior retractor can comprise a rasp tunnel with a guide tube nested therein and not include a reamer tunnel as described above. As described above, posterior retractor 122 is not always utilized, and if utilized, is not always utilized in its nested configuration. In one exemplary embodiment, guide tube 124, reamer tunnel 126, and rasp tunnel 130 are each inserted into and removed from posterior incision 46 as necessary. In an alternative embodiment, the tubular retractor disclosed in U.S. patent application Ser. No. 09/992,639 filed Nov. 6, 2001 and published as U.S. Publication No. U.S. 2002/0099447 A1, the disclosure of which is hereby explicitly incorporated by reference herein, is utilized.

Referring now to FIG. 21, rasp handle 212 includes cannular insertion member 168, impact surface 164, grip 166, elongate guide aperture 202, elongate aperture 200, and engagement channel 190. Rasp 204 includes an aperture 216 sized to receive and retain retainer 210 on distal end 208 of flexible cable 192. Retainer 210 is placed in aperture 216 and flexible cable 192 follows cable channel 217 to exit rasp 204. Proximal end 194 of flexible cable 192 is inserted through elongate aperture 200 of cannular insertion member 168 and distal rasp engagement guide 206 is piloted to guide channel 215 of rasp 204. After exiting the proximal end of elongate aperture 200, proximal end 194 of flexible cable 192 may be received in engagement channel 190. Engagement channel 190 is sized to accommodate and retain retainer 196. After retainer 196 is operably positioned in engagement channel 190, grip 166 may be actuated to tension flexible cable 192.

Figure 20A:
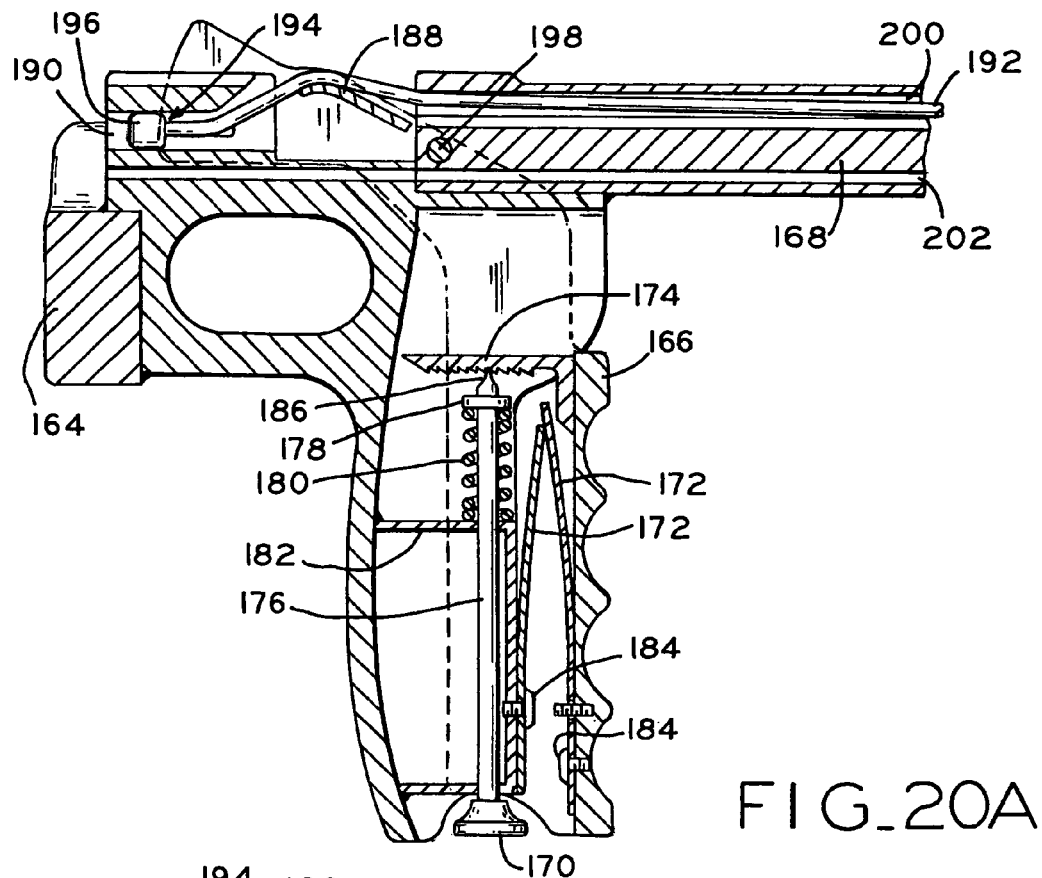
FIGS. 20A and 20B are partial sectional views of the rasp handle.
Figure 20B:
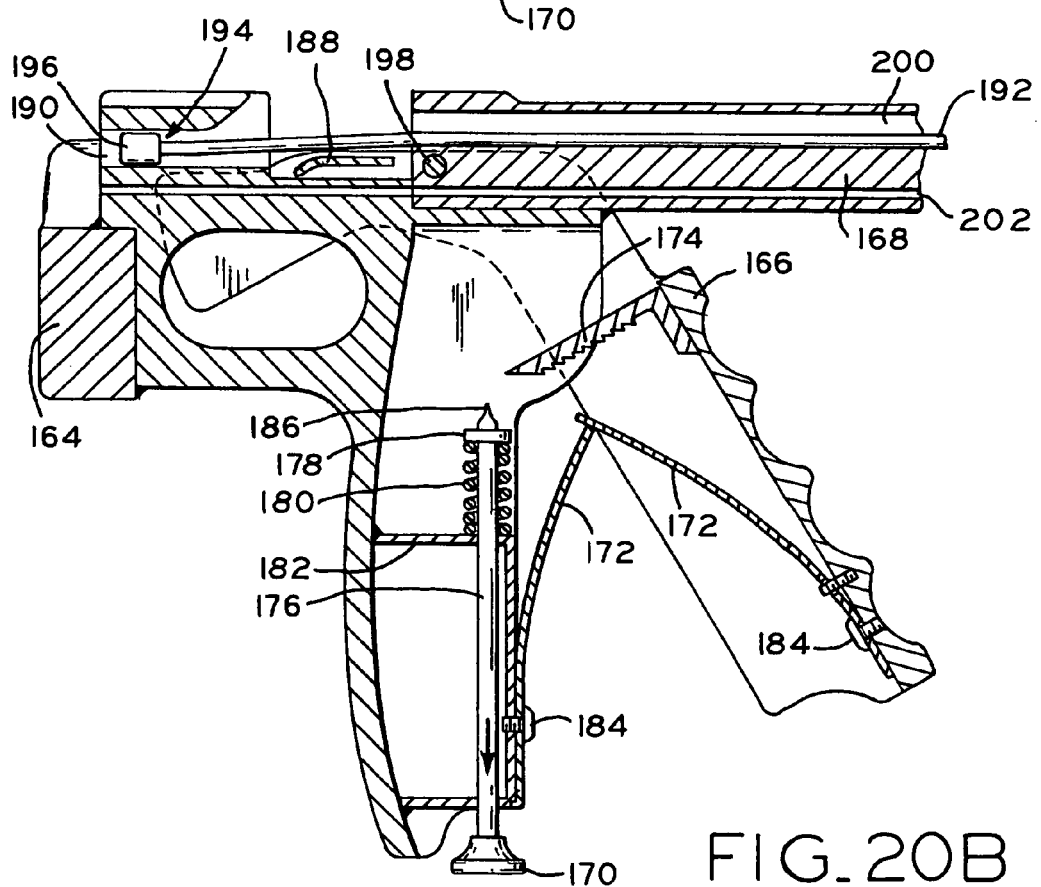

Referring now to FIG. 20B, retainer 196 is operably positioned in engagement channel 190. Attaching means 184, such as, e.g., rivets, belts, etc. are utilized to affix biasing elements 172 to grip 166 and internal handle surface 182. Grip 166 is outwardly biased by handle biasing elements 172 and pivots about pivot point 198. Grip 166 includes tensioning member 188 and ratchet 174. Ratchet 174 is designed for engagement with tapered end 186 of pawl 176. Pawl 176 includes pawl flange 178. Spring 180 engages internal handle surface 82 and pawl flange 178 to bias pawl 176 toward cannular insertion member 168. Actuation of grip 166 against the biasing force of biasing elements 172 rotates grip 166 about pivot point 198, causes ratchet 174 to come into operative engagement with tapered end 186 of pawl 176, and causes tensioning member 188 to contact flexible cable 192. FIG. 20A illustrates grip 166 retained by pawl 176 in the closed position. As illustrated, tensioning member 188 contacts and tensions flexible cable 192, thus locking rasp 204 to rasp handle 212. Lock disengagement knob 170 can be pulled against the biasing force of spring 180 to unlock grip 166.

FIGS. 31-36 illustrate an alternative embodiment rasp handle in accordance with the present invention. As illustrated in FIGS. 31-35, rasp handle 300 includes proximal end 302 including impaction surface 328 (see, e.g., FIGS. 32-35). Proximal end 302 further includes a plurality of guide handle apertures 316 into which anteversion handle 312 (FIGS. 31 and 33) can be secured. When using rasp handle 300 to seat a rasp in femur 62, anteversion handle 312 can be utilized to set the anteversion of the femoral implant. As illustrated in FIG. 36, proximal end 302 of rasp handle 300 includes three anteversion handle apertures on each side thereof. Specifically, anteversion holes 316a', 316b', and 316c' are left anteversion holes, while anteversion holes 316a, 316b, and 316c are right anteversion holes. That is, anteversion holes 316a', 316b', and 316c' are utilized to set femoral implant anteversion when performing a total hip arthroplasty on the left hip, while anteversion holes 316a, 316b, and 316c are utilized to set anteversion of the femoral implant when performing a total hip arthroplasty of the right hip. Anteversion holes 316a and 316a' are set at 0° of anteversion. Anteversion holes 316a and 316a' are utilized when no anteversion of the femoral implant is sought. In such an embodiment, anteversion handle 312 is connected to the appropriate anteversion aperture 316a or 316a' and vertically positioned (with the patient lying in a supine position) to prepare femur 62 to receive a femoral implant in 0° of anteversion. Anteversion apertures 316b and 316b' form an angle of 7½ degrees with anteversion apertures 316a and 316a', respectively. These apertures can be utilized to set 7½ degrees of anteversion for the femoral implant. Similarly, anteversion apertures 316c and 316c' form an angle of 15° with anteversion apertures 316a and 316a' and can be used to set anteversion of 15° for the femoral implant. For the purposes of this document, when referring to the angle formed by a pair of anteversion apertures, the longitudinal axis of each aperture forms a line comprising a leg of the referenced angle. If a surgeon wants to achieve 7½ or 15 degrees of anteversion, the surgeon can insert anteversion handle 312 into the appropriate anteversion aperture and orient anteversion handle 312 vertically to achieve the desired anteversion. Proximal end 302 of rasp handle 300 further includes slap hammer aperture 344 for connection of a slap hammer to rasp handle 300. Slap hammer aperture 344 is provided in the event that a surgeon does not favor rasp removal by means of impacting the undersurface of proximal end 302, i.e., the surface opposite impaction surface 328.

Figure 31:
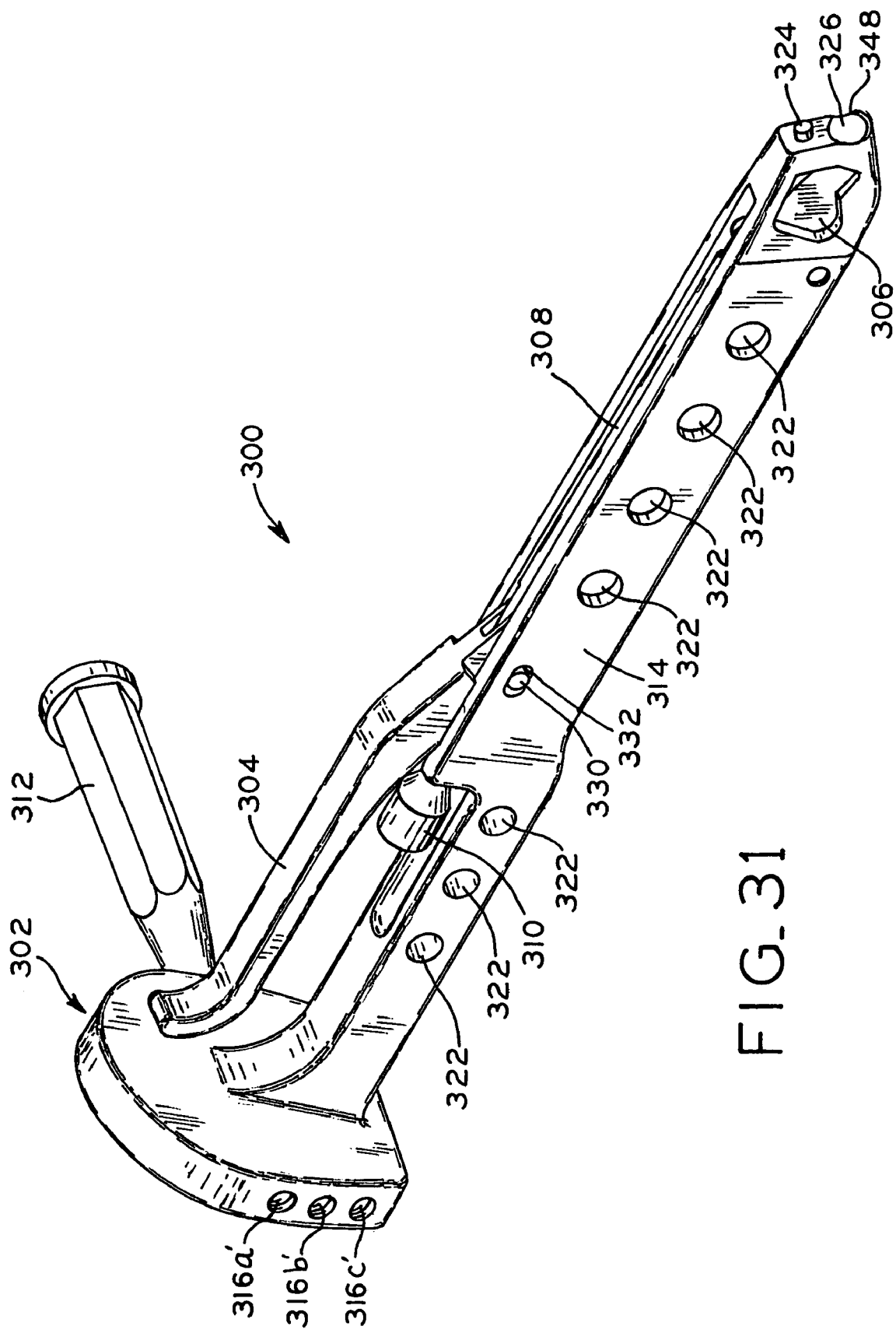
FIG. 31 is a perspective view of an alternative embodiment rasp handle in accordance with the present invention.

As illustrated in FIGS. 31, 32, and 34, rasp handle 300 includes frame 314 having transverse apertures 322 formed therein. Transverse apertures add to the cleanability of rasp handle 300 and provide for weight reduction over an embodiment absent transverse apertures 322.

To secure rasp 204' (FIG. 35) to rasp handle 300, handle lever 304 is rotated away from frame 314 to the position illustrated in FIG. 35. Rotation of handle lever 304 to this position effects proximal movement of second handle lever pin 334 which, consequently, moves linkage arm 308 and linkage arm pin 336 proximally. Locking jaw 306 is pivotally secured to frame 314 via locking jaw pin 338 so that movement of handle lever 304 causes rotation of locking jaw 306 about locking jaw pin 338 and positions locking jaw 306 as illustrated in FIG. 35. As illustrated in FIGS. 31 and 32, handle lever 304 is pivotally connected to frame 314 via first handle lever pin 330. First handle lever pin 330 is positioned in channel 332 formed in frame 314. Placement of first handle lever pin 330 in channel 332 allows for proximal/distal translation of handle lever 304. As illustrated in FIGS. 34 and 35, handle lever 304 is pivotally connected to linkage arm 308 via second handle lever pin 334. Linkage arm 308 is pivotally connected via linkage arm pin 336 to locking jaw 306 and locking jaw 306 is pivotally connected to frame 314 via locking jaw pin 338. As illustrated in FIG. 32, frame 314 includes locking jaw pin aperture 340 into which locking jaw pin 338 is positioned.

To secure rasp 204' to rasp handle 300, post 318 of rasp 204' is inserted into rasp handle docking aperture 326 and docking boss 324 of rasp handle 300 is positioned in rasp handle docking aperture 346 of rasp 204'. Handle lever 304 is then rotated from the position illustrated in FIG. 35 to the position illustrated in FIG. 34. Rotation of handle lever 304 to the position illustrated in FIG. 34 causes movement of second handle lever pin 334 from the position illustrated in FIG. 35 to the position illustrated in FIG. 34 and consequently causes distal movement of linkage arm 308, and linkage arm pin 336 which causes rotation of locking jaw 306 into the position illustrated in FIG. 34, with locking tooth 342 of locking jaw 306 postioned within V-notch 320 of post 318 of rasp 204'. If insufficient clamping force is exerted on V-notch 320 of post 318 by locking jaw 306, then handle lever 304 can be moved into the open position illustrated in FIG. 35 and adjustment screw 310 can be utilized to displace first handle lever pin 330 distally so that actuation of handle lever 304 into the closed position will cause greater distal displacement of linkage arm 308 and linkage arm pin 336, and, consequently, cause greater rotation of locking jaw 306 to exert additional clamping force on post 318 of rasp 204'.

After the final rasp is fully seated in femur 62 as described hereinabove, handle lever 304 can be rotated into the open position illustrated in FIG. 35 to allow for disengagement of rasp handle 300 from rasp 204' so that a trial reduction can be performed with a trial femoral neck and head secured to rasp 204'. After completion of a trial reduction, rasp handle 300 is reinserted into the body and docked with rasp 204 to allow for removal thereof. To redock rasp handle 300, tactile feedback is utilized to identify post 318 of rasp 204'. After it is located, post 318 is positioned within rasp handle docking aperture 326 which is facilitated by the fact that rasp handle docking aperture 326 includes a female taper whereby the distal most portion of rasp handle docking aperture 326 is larger than the proximalmost portion thereof. With post 318 positioned within rasp handle docking aperture 326, rotation of rasp handle 300 can be utilized to position docking boss 324 in rasp docking aperture 346. Handle lever 304 is then rotated from the open position illustrated in FIG. 35 to the closed position illustrated in FIG. 34 to secure rasp 204' to rasp handle 300. In the event that the proximal end of rasp 204' does not abut the distal end of rasp handle 300, the cooperating ramped surfaces of locking tooth 342 and V-notch 320 will work to draw rasp handle 300 closer to rasp 204 until they are positioned in abutting relationship. As illustrated in FIGS. 31, 32, and 35, rasp handle docking aperture 326 includes radiused profile 348 which allows for escape of soft tissues from between rasp handle 300 and rasp 204' when rasp handle 300 is secured to rasp 204'. With rasp handle 300 secured to rasp 204', rasp 204' can be removed from femur 62 to allow for seating of the final femoral implant. In an alternative embodiment, an image guidance array can be utilized in lieu of or in addition to anteversion handle 312 to position rasp 204 in the appropriate orientation in the femur. The rasp handles of the present invention are advantageously formed with a low profile insertion member heading a cross sectional area no greater than the rasps to which they are attached.

Referring now to FIG. 23, provisional neck 222 can be locked to rasp 204 utilizing forceps 220. Forceps 220 include blade ends 230, 232. Blade ends 230, 232 are sized for insertion into provisional head apertures 234, 236, respectively (FIGS. 24B and 24C). As illustrated in FIG. 24A, provisional neck 222 includes locking cylinder 224 and spring 228. Spring 228 upwardly biases locking cylinder 224. Upon insertion into apertures 234, 236, blade ends 230, 232 can contact tapered portion 226 of locking cylinder 224. Actuation of blade ends 230, 232 against tapered portion 226 causes locking piston 224 to move in a direction opposite to the biasing force of spring 228. Provisional neck 222 is clamped to forceps 220 and slid in a radial direction into provisional neck engagement area 218 (FIGS. 21 and 21A) on rasp 204. After provisional neck 222 is fully slid onto rasp 204, forceps 220 may be released, thereby allowing locking piston 224 to return to its locked position under the biasing force of spring 228. Rasp 204 includes circular cut outs 217 which can be engaged by locking cylinder 224 to lock provisional neck 222 in place.

Channels 225 (FIG. 24A) on provisional neck 222 accommodate protrusions 219 (FIG. 21) on rasp 204. Provisional neck 222 is slid onto rasp 204 with protrusions 219 occupying channels 225 of provisional neck 222. Stop 223 of provisional neck 222 abuts protrusions 219 when provisional neck 222 is completely slid onto rasp 204. When stop 223 abuts protrusions 219, locking cylinder 224 may be locked (i.e., forcep blades 230, 232 released) so that locking cylinder 224 engages circular cut outs 217, locking provisional neck 222 to rasp 204.

Figure 56:
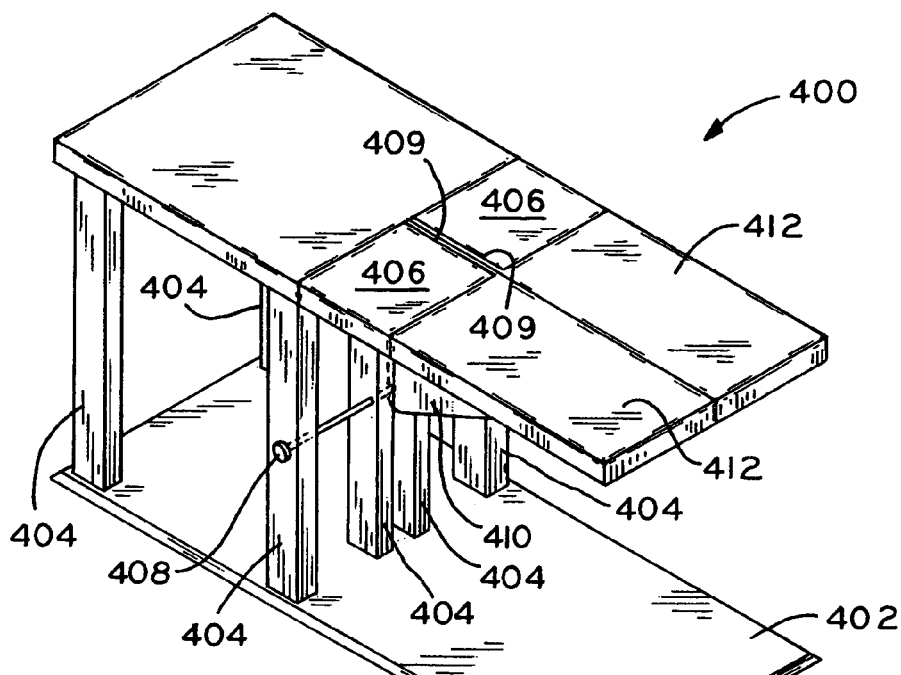
FIG. 56 is a perspective view of an operating table in accordance with the present invention.
Figure 57:
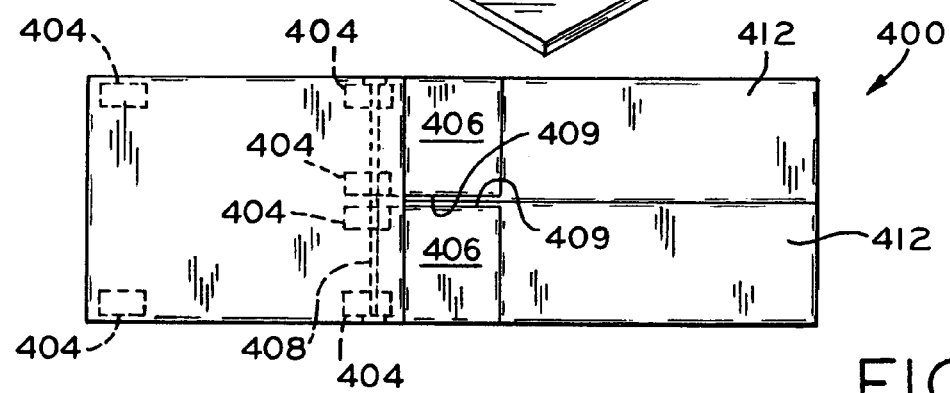
FIG. 57 is a top elevational view thereof.
Figure 58:
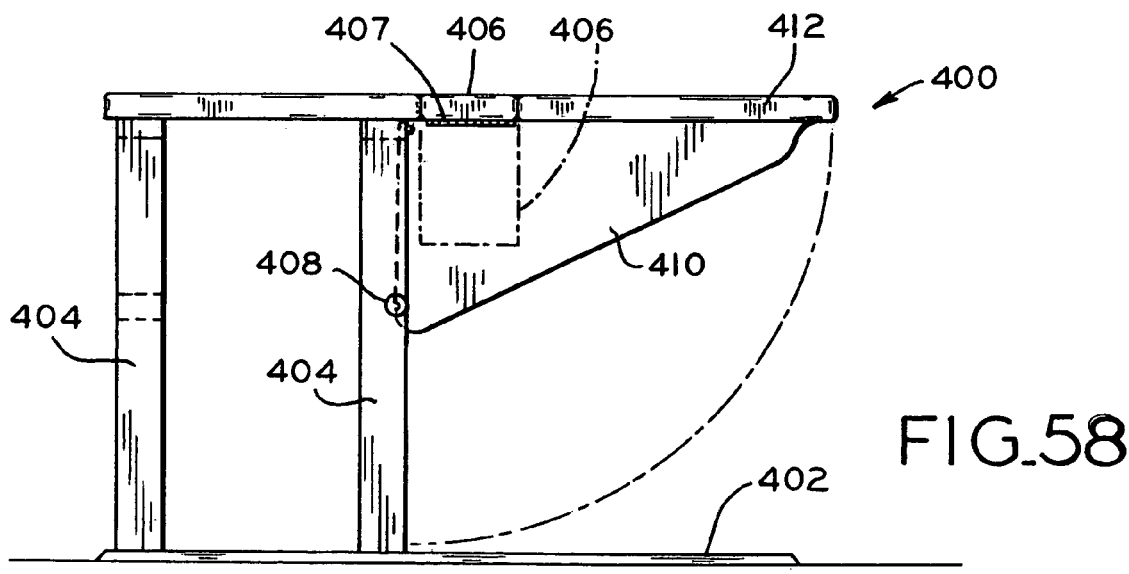
FIG. 58 is a side elevational view thereof.
Figure 61:
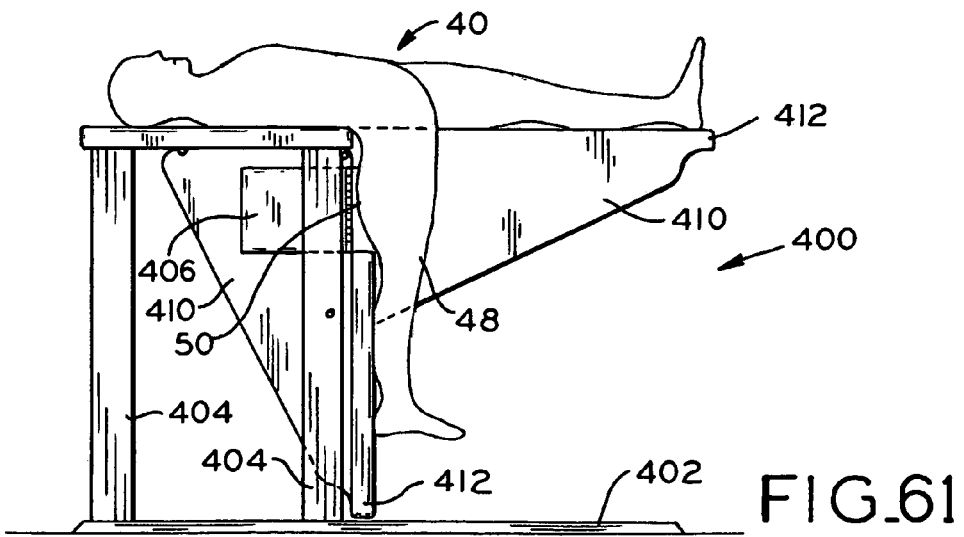
FIG. 61 is a side elevational view illustrating rotation of a leg panel of the operating table of the present invention to allow for hyperextension of the patient's hip.

FIGS. 56-61 illustrate operating table 400 in accordance with the present invention. As illustrated in FIGS. 56-58, operating table 400 is secured to base 402 via supports 404. Operating table 400 includes a pair of leg panels 412 on top of which a patient's legs can be positioned. Each leg panel 412 includes a buttocks door 406. Each buttocks door 406 includes a hinge 407 as illustrated in FIG. 58. Hinge 407 hingedly connects medial side 409 of each buttocks door 406 to a leg panel 412 so that each buttocks door 406 can be rotated between the closed position illustrated in FIG. 59 to support a patient's buttocks, to the open position illustrated in FIG. 60, allowing a patient's buttocks to protrude through the top of operating table 400. Each leg panel 412 is hingedly connected to operating table 400 and, therefore, is rotatable from the supine position illustrated in FIGS. 56, and 58-60 and the hyperextended position illustrated in FIG. 61. In the exemplary embodiment illustrated in FIGS. 56-61, each leg panel 412 includes a support 410 useful in maintaining the leg panel in one of the supine and hyperextended positions as illustrated in FIG. 61. In further embodiments of operating table 400, leg panels 412 will be mechanically or hydraulically actuatable between a supine and hyperextended position and include the ability to achieve nearly infinite degrees of hyperextension from about 0° of hyperextension, i.e., supine, to about 120° of hyperextension.

Figure 59:
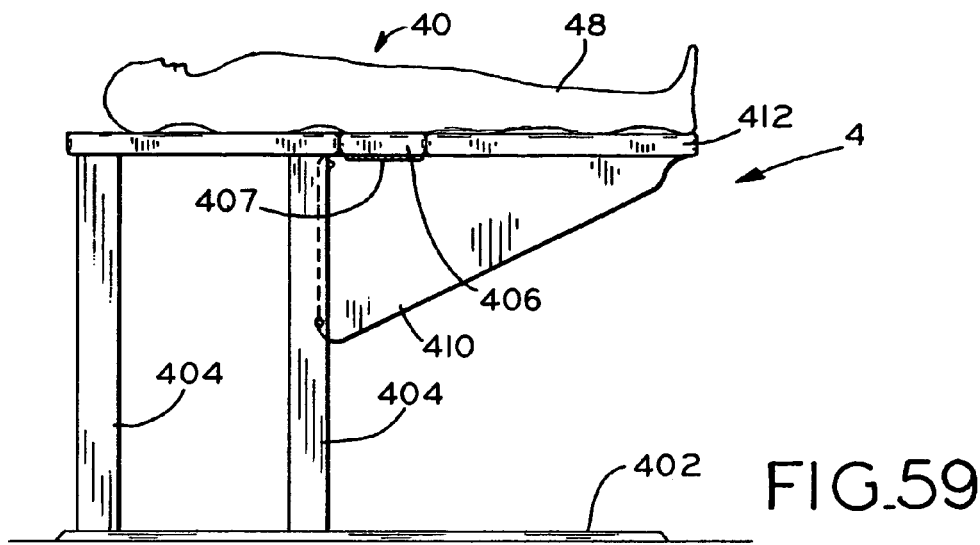
FIG. 59 is a side elevational view thereof illustrating a patient positioned atop the operating table of the present invention.
Figure 60:
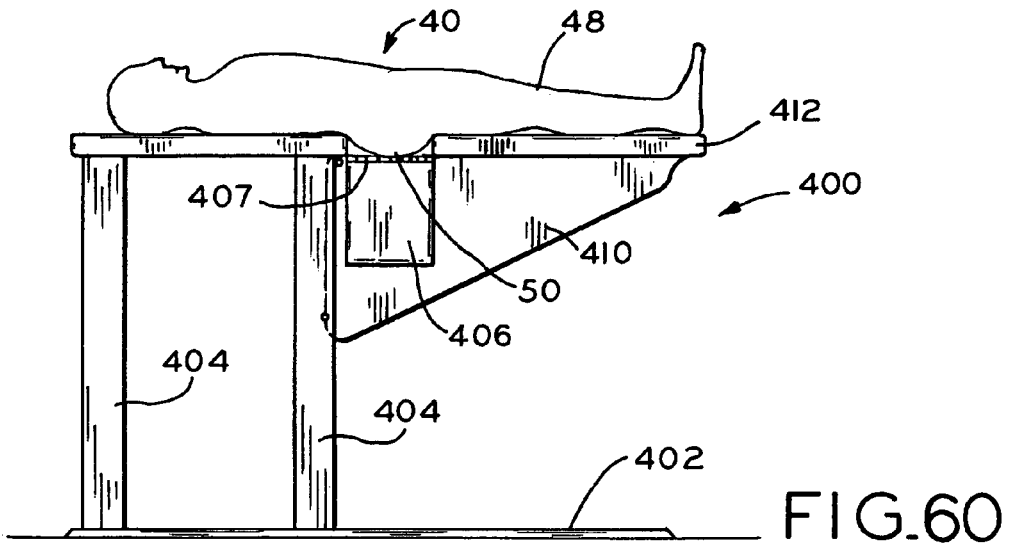
FIG. 60 is a side elevational view of the operating table of the present invention illustrating use of a buttocks door to allow for extension of the patient's buttocks through the table top.

FIG. 59 illustrates patient 40 including operative leg 48. As illustrated in FIG. 59, patient 40 is placed in supine position atop operating table 400 with operative leg 48 positioned atop one of leg panels 412. The non-operative leg is similarly placed atop the remaining leg panel 412. With the patient positioned as illustrated in FIG. 59, buttocks door 406 can be rotated into the open position illustrated in FIG. 60 to allow buttocks 50 to protrude through the top of operating table 400. As illustrated in FIG. 61, leg panel 412 positioned underneath operative leg 48 can be rotated to position operative leg 48 in approximately 90° of hyperextension. Buttocks door 406 advantageously allows the operative leg of a larger patient to be placed in a greater degree of hyperextension than would be allowable without buttocks door 406.

The top surface of operating table 400 is completely radiolucent to allow for intraoperative image intensification. Furthermore, operating table 400 is constructed to be of minimal width to carry an average size patient thereon to allow for maximum ease of use of a C-arm image intensification system. In one exemplary embodiment, a system of operating tables 400 is provided, each with increasing width to accommodate patients of varying size while providing a table of minimum width to support the relevant patient. The relatively narrow width of operating table 400 is advantageous in that the operating surgeon will stand adjacent operative leg 48 while the C-arm image intensification system will be positioned adjacent the opposite side of operating table 400. The relatively narrow width of operating table 400 will therefore allow for optimum placement of the C-arm image intensification system with respect to operative leg 48. It is important to note that support 410 associated with each leg panel 412 will be sized to accommodate passage of a C-arm thereabout and will be formed of radiotransparent material. Operating table 400 is useful when hyperextending the non-operative leg as described hereinabove. Furthermore, operating table 400 is useful in performing the one incision minimally invasive total hip arthroplasty described hereinbelow because the non-operative leg can be hyperextended as described hereinabove.

The present invention provides for a single incision minimally invasive total hip arthroplasty. The total hip arthroplasty of this form of the present invention is prepared utilizing one of anterior incisions 44 and 44'. In the total hip arthroplasty of this form of the present invention, the acetabulum is prepared and the acetabular component is seated as is discussed above with respect to the two incision minimally invasive total hip arthroplasty. In this form of the present invention, the operative leg is hyperextended at least about 70° and the femur is prepared and the femoral implant is seated through the anterior incision. In one exemplary embodiment of the one incision minimally invasive total hip arthroplasty of the present invention, the leg is hyperextended about 75° to 90°.

Figure 62:
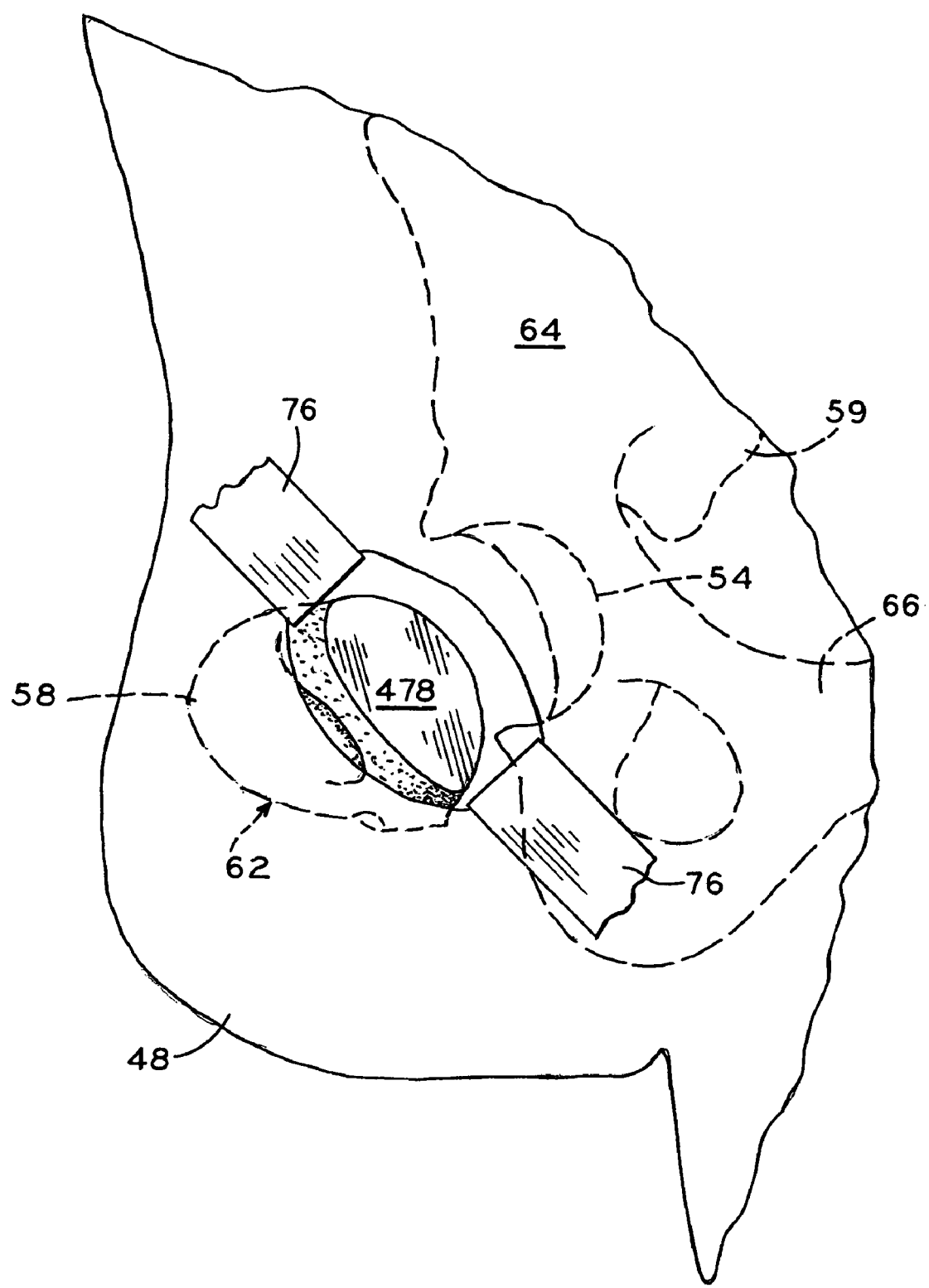
FIG. 62 is an anterior elevational view of the osteotomized femoral neck viewed through an anterior incision made in accordance with the present invention, with the operative leg placed in hyperextension.
Figure 63:
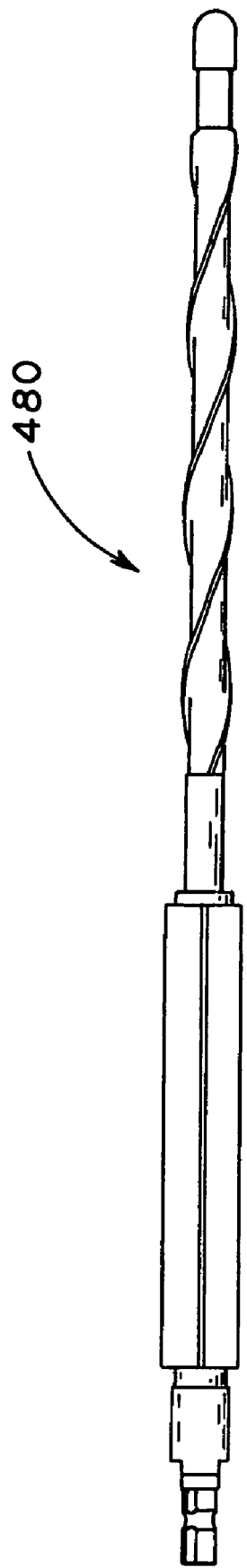
FIG. 63 is radial elevational view of a lateralizing reamer of the present invention.

FIG. 61 illustrates patient 40 with operative leg 48 hyperextended to about 90° of hyperextension. Use of operating table 400 of the present invention to allow for this hyperextension of operative leg 48 is described hereinabove. After operative leg 48 is positioned as illustrated in FIG. 61, retractors are inserted into the anterior incision and positioned around the upper femur to allow for visualization of the bone. Advantageously, as operative leg 48 is hyperextended, the proximal femur is positioned closer to the anterior incision to allow for visualization of the osteotomized femoral neck through the anterior incision. This arrangement is clearly depicted in the supine elevational view of FIG. 62 in which osteotomized femoral neck 478 is clearly visible through the anterior incision. After positioning operative leg 48 as illustrated in FIGS. 61 and 62, preparation of the femur begins. The technique used for preparing femur 62 (FIG. 62) will depend in large part on patient physiology. Specifically, the technique described above with respect to the two incision minimally invasive total hip arthroplasty can be used to prepare femur 62 is patient physiology allows for hyperextension to about 90° to allow for maximum access to osteotomized femoral neck 478. If patient physiology allows for hyperextension to only about 75° to 80°, then an alternative technique may be utilized to prepare femur 62 to receive the femoral implant. Specifically, in this latter case where hyperextension of only about 75° to 80° is possible, curved instruments may be utilized to prepare femur 62 to receive a curved femoral implant.

If the operative hip cannot be hyperextended to about 90° then, generally speaking, direct access to osteotomized femoral neck 478 (FIG. 62) cannot be achieved. With this in mind, straight instruments for preparing femur 62 to receive a femoral implant will generally not be applicable because such instruments typically require insertion directly into osteotomized femoral neck 478 coaxial with the principal portion of the femoral shaft. In this situation, curved preparation tools can be utilized because such tools can be inserted into the osteotomized femoral neck along the axis of the posterior femoral bow.

Preparation of the femur in a case in which about 90° of hyperextension cannot be achieved can begin by inserting a curved awl into osteotomized femoral neck 478. The curved awl will follow the posterior bow of the femur and begin preparation of the intramedullary canal of femur 62 to receive a femoral implant. In one exemplary embodiment, a curved rasp is utilized to begin preparation of the femoral canal. If reaming is desired, a flexible reamer can be inserted into the intramedullary canal of the femur to ream the same. The flexible reamer will generally glance off the posterior cortical wall of femur 62 and effect reaming of the intramedullary canal. A guide wire may or may not be utilized with the flexible reamer. After inserting the awl and reaming as necessary, a curved femoral rasp is used to complete preparation of the femur to receive, e.g., a curved prosthetic femoral component. The curved femoral rasp can be utilized to effect a trial reduction as described hereinabove with respect to the two incision minimally invasive total hip arthroplasty. To perform a trial reduction, operating table 400 will be returned to the position illustrated in FIG. 60 to return patient 40 to the supine position. Patient leg 48 again will be hyperextended as illustrated in FIGS. 61 and 62 to allow for removal of the final femoral rasp and seating of the femoral implant.

While the method of the current invention has been described with reference to particular hip prostheses, this is not meant to be limiting in any way and it will be understood that the method of the current invention could be used with many prosthetics, including, e.g., a cementless prosthesis, a hybrid prosthesis having a cemented stem and a cementless acetabular cup, a cemented prosthesis having both a cemented stem and a cemented acetabular cup, or an Endo prosthesis for replacing only the femoral head. In a procedure in which a cemented femoral stem is utilized, the bone cement will generally be inserted through the anterior incision and a bagged stem will be inserted through the posterior incision. If the single anterior incision is utilized, a cemented stem could be inserted without requiring use of the protective bag described above.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An acetabular cup inserter, comprising:
   a frame having a proximal frame end, a distal frame end, and an offset leg extending between and offset from said proximal frame end and said distal frame end, said proximal frame end having a handle and an impaction surface, said distal frame end adapted for connection of an acetabular cup thereto, said distal frame end defining a shoulder and a projection, said projection having an opening extending therethrough;
   a threaded shaft associated with said frame and configured to threadingly engage the acetabular cup, said threaded shaft extending from said distal frame end and through said opening in said projection;
   a cap having a cap opening extending therethrough, said cap seated against said shoulder of said distal frame end with said projection of said distal frame end extending into said cap opening and said threaded shaft extending through said cap opening;
   a drive linkage rotationally connected to said threaded shaft, whereby rotation of said drive linkage results in corresponding rotation of said threaded shaft, wherein said threaded shaft is biased in a direction away from said distal frame end and toward the proximal frame end and into engagement with said drive linkage; and
   a locking lever and a locking shaft, said locking lever engaged with said locking shaft, said locking shaft having a cam, said locking shaft positioned proximate said drive linkage, whereby rotation of said locking lever causes said cam to selectively inhibit rotation of said drive linkage.

2. The acetabular cup inserter of claim 1, wherein said drive linkage includes a universal joint, said universal joint comprising:
   a male aspect, said male aspect comprising a multiply sided spheroid; and
   a female aspect having an internal aperture with a polygonal cross section, said male aspect positioned within said internal aperture.

3. The acetabular cup inserter of claim 2, wherein said male aspect comprises a six sided spheroid and wherein said internal aperture of said female aspect has a hexagonal cross section, and wherein said male aspect is rotationally fixed to said female aspect.

4. The acetabular cup inserter of claim 1, further comprising an alignment frame secured to said frame.

5. The acetabular cup inserter of claim 1, wherein said offset frame leg is offset from said impaction surface.

6. An acetabular cup inserter, comprising:
   a frame having a proximal frame end, a distal frame end, and an offset leg extending between and offset from said proximal frame end and said distal frame end, said proximal frame end having a handle and an impaction surface, and said distal frame end adapted for connection of an acetabular cup thereto;
   a threaded shaft associated with said frame and extending from said distal frame end, said threaded shaft configured to threadingly engage the acetabular cup;
   a drive linkage rotationally connected to said threaded shaft, whereby rotation of said drive linkage results in corresponding rotation of said threaded shaft, wherein said threaded shaft is biased in a direction away from said distal frame end and toward said proximal frame end and into engagement with said drive linkage, and wherein the acetabular cup threadingly secured to said threaded shaft is biased toward said distal frame end; and
   a locking lever and a locking shaft, said locking lever engaged with said locking shaft, said locking shaft having a cam, said locking shaft positioned proximate said drive linkage, whereby rotation of said locking lever causes said cam to selectively inhibit rotation of said drive linkage.

7. The acetabular cup inserter of claim 6, wherein said drive linkage includes a universal joint, said universal joint comprising:
   a male aspect, said male aspect comprising a multiply sided spheroid; and
   a female aspect having an internal aperture with a polygonal cross section, said male aspect positioned within said internal aperture.

8. The acetabular cup inserter of claim 6, further comprising a cap positioned proximate a distal end of said frame, said cap having an opening extending therethrough, said threaded shaft extending through said opening in said cap, wherein the acetabular cup is biased in the direction of said cap and contacts said cap when threadingly engaged with said threaded shaft.

9. The acetabular cup inserter of claim 6, further comprising an alignment frame secured to said frame.

10. The acetabular cup inserter of claim 6, wherein said offset frame leg is offset from said threaded shaft.

11. The acetabular cup inserter of claim 6, wherein said offset frame leg is offset from said impaction surface.

12. The acetabular cup inserter of claim 1, further comprising a spring, said spring biasing said threaded shaft in a direction away from said distal frame end and into engagement with said drive linkage.

13. The acetabular cup inserter of claim 6, further comprising a spring, said spring biasing said threaded shaft in a direction away from said distal frame end and into engagement with said drive linkage.

* * * * *